(12) United States Patent
Sticklen

(10) Patent No.: US 8,350,123 B2
(45) Date of Patent: *Jan. 8, 2013

(54) TRANSGENIC COVER PLANTS CONTAINING HEMICELLULASE AND CELLULASE WHICH DEGRADE LIGNIN AND CELLULOSE TO FERMENTABLE SUGARS

(75) Inventor: Masomeh B. Sticklen, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/276,662

(22) Filed: Oct. 19, 2011

(65) Prior Publication Data

US 2012/0090231 A1 Apr. 19, 2012

Related U.S. Application Data

(63) Continuation of application No. 11/999,197, filed on Dec. 4, 2007, now Pat. No. 8,093,456, which is a continuation-in-part of application No. 11/399,675, filed on Apr. 6, 2006, now Pat. No. 7,371,926, which is a continuation of application No. 09/981,900, filed on Oct. 18, 2001, now Pat. No. 7,049,485.

(60) Provisional application No. 60/242,408, filed on Oct. 20, 2000.

(51) Int. Cl.
*C12N 15/82* (2006.01)
*C12N 15/00* (2006.01)
*C12N 15/09* (2006.01)
*C12N 15/52* (2006.01)

(52) U.S. Cl. ..... 800/284; 800/288; 800/278; 435/320.1; 435/468; 536/23.1; 536/23.2; 536/23.7; 536/23.74

(58) Field of Classification Search .................. None
See application file for complete search history.

(56) References Cited

U.S. PATENT DOCUMENTS

| | | |
|---|---|---|
| 3,990,944 A | 11/1976 | Gauss et al. |
| 3,990,945 A | 11/1976 | Huff et al. |
| 5,296,462 A | 3/1994 | Thomashow |
| 5,356,816 A | 10/1994 | Thomashow |
| 5,539,095 A | 7/1996 | Sticklen et al. |
| 5,641,876 A | 6/1997 | McElroy et al. |
| 5,736,369 A | 4/1998 | Bowen et al. |
| 5,767,368 A | 6/1998 | Zhong et al. |
| 5,773,702 A | 6/1998 | Penner et al. |
| 5,871,730 A | 2/1999 | Brzezinski et al. |
| 5,981,835 A | 11/1999 | Austin-Phillips et al. |
| 6,013,860 A | 1/2000 | Himmel et al. |
| 6,100,456 A | 8/2000 | Sticklen et al. |
| 6,103,956 A | 8/2000 | Srienc et al. |
| 6,818,803 B1 | 11/2004 | Austin-Phillips et al. |

FOREIGN PATENT DOCUMENTS

WO WO98/11235 3/1998

OTHER PUBLICATIONS

Austin et al., Euphytica 85: 381-393 (1995).
Yadav et al., Appl. Environ. Microbiol. 61: 2560-2565 (1995).
Yadav et al., Appl. Environ. Microbiol. 61: 677-680 (1995).
de Boer et al., Gene 60: 93-102 (1987).
Zhang et al., Theor. Appl. Genet. 92: 752-761 (1996).
Zhong et al., Plant Physiol. 110: 1097-1107 (1996).
Zhong et al., Planta, 187: 483-489 (1992).
Lee et al., EMBO J. 7: 1241-1248 (1988).
Miki et al., Theor. Appl. Genet. 80: 449-458 (1990).
Marshall et al., Theor. Appl. Genet. 83: 435-442 (1992).
Van Damme et al., Plant Mol. Biol. 24: 825-830 (1994).
Abe et al., J. Biol. Chem. 262: 16793-16797 (1987).
Linthorst et al., Plant Mol. Biol. 21: 985-992 (1993).
Beachy et al., Ann. Rev. Phytopathol. 28: 451-74 (1990).
Tavladoraki et al., Nature 366: 469 (1993).
Yamaguchi-Shinozaki et al., Plant Cell 6: 251-264 (1994).
Allen et al., The Plant Cell 5: 603-613 (1993).
Allen et al., The Plant Cell 8: 899-913 (1996).
Mlynarova et al., The Plant Cell 8: 1589-1599 (1996).
Thornburg et al., Proc. Natl. Acad. Sci. USA 84: 744-748 (1987).
Thompson et al., EMBO J. 6: 2519-2523 (1987).
Zhong et al., Plant Science 116: 73-84 (1996).
McElroy et al., Mol. Gen. Genet. 231: 150-160 (1991).
Loza-Tavera et al., Plant Physiol. 93: 541-548 (1990).
Cao et al., Plant Cell Reports 11: 586-591 (1992).
Zhong et al., Planta 187: 490-497 (1992).
Dale et al., Bioresource Technol. 56: 111-116 (1996).
de la Rosa et al., Appl. Biochem. Biotechnol. 45/46: 483-497 (1994).
Tien et al., Meth. Enzymol. 161: 238-249 (1988).
Bradford, Anal. Biochem. 72:248-254 (1976).
Reddy et al., FEMS Microbiol. Rev. 13: 137-152 (1994).

*Primary Examiner* — Brent T Page
(74) *Attorney, Agent, or Firm* — Dickinson Wright PLLC

(57) ABSTRACT

The present invention provides transgenic cover crop plants which after harvest degrade the hemicellulose and cellulose therein to fermentable sugars which can further be fermented to ethanol or other products. In particular, the transgenic plants comprise cellulase, hemicellulase and optionally ligninase genes from microbes operably linked to a DNA encoding a signal peptide which targets the fusion polypeptide produced therefrom to an organelle of the plant, in particular, the chloroplasts. When the transgenic plants are harvested, the plants are ground to release the hemicellulase and cellulase which then degrade the hemicellulose and cellulose of the transgenic plants to produce the fermentable sugars.

20 Claims, 10 Drawing Sheets

(2 of 10 Drawing Sheet(s) Filed in Color)

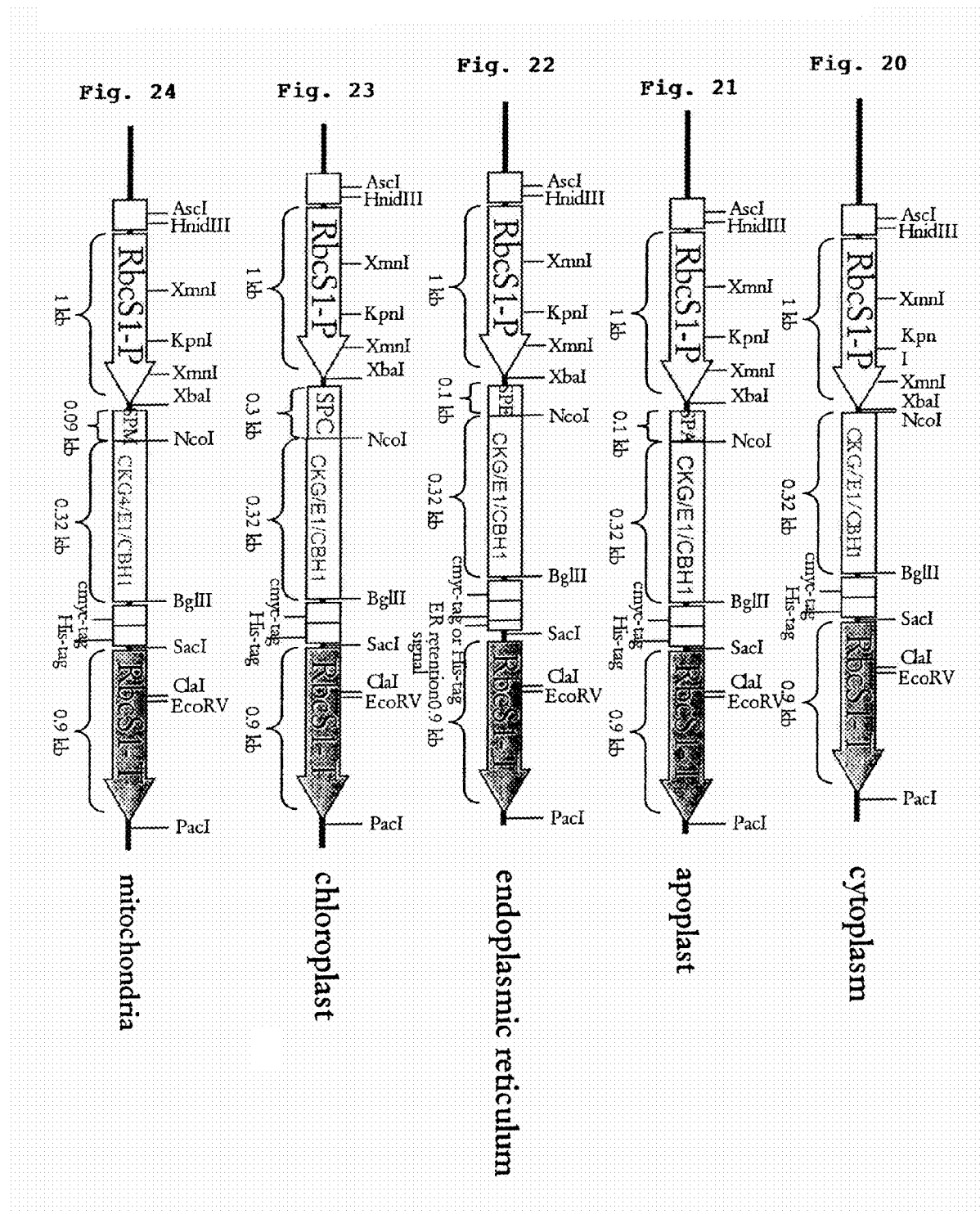

SEQUENCE LISTING

<160> NUMBER OF SEQ ID NOS: 22

<210> SEQ ID NO 1
<211> LENGTH: 1110
<212> TYPE: DNA
<213> ORGANISM: Oryza sativa

<400> SEQUENCE: 1

```
gggtcggaga tgccaccacg gccacaaccc acgagcccgg cgcgacacca ccgcgcgcgt      60
tgagccagcc acaaacgccc gcggataggc gcgccgcacg cggccaatcc taccacatcc     120
ccggcctccg cggctcgagc gccgtgccat ccgatccgct gagttttggc tatttatacg     180
taccgcggga gcctgtgtgc agagagtgca tctcaagaag tactcgagca aagaaggaga     240
gagcttggtg agctgcagag atggccccct ccgtgatggc gtcgtcggcc accaccgtcg     300 ctccttcca gggctcaagt ccaccgccgg catgccgtcg cccgccgtcc gaactccagc      360
ttcggcaacg tcagcatggc ggcaggatca ggtgcatgca ggtaattacc tactgatcca     420
acacacattc ttcttcttct tcttcttctt aaccaacatt aaccaacaac tcaattatcg     480
tttattcatt gaggtgtggc cgattgaggg catcaagaag ttcgagaccc tctcctacct     540
gccaccgctc accgtggagg acctcctgaa gcagatcgag tacctagctc cgttccaagt     600
ggtgccctgc ctcgagttca gcaaggtcgg atttgtctac cgtgagaacc acaagtcccc     660
tggatactac gacggcaggt actggaccat gtggaagctg cccatgttcg ggtgcaccga     720
cgccacccag gtcgtcaagg agctcgagga ggccaagaag gcgtaccctg atgcattcgt     780
ccgtatcatc ggcttcgaca acgttaggca ggtgcagctc atcagcttca tcgcctacaa     840
cccgggctgc gaggagtctg gtggcaacta agccgtcatc gtcatatata gcctcgttta     900
```

-continued

| | |
|---|---|
| attgttcatc tctgattcga tgatgtctcc caccttgttt cgtgtgttcc cagtttgttt | 960 |
| catcgtcttt tgattttacc ggccgtgctc tgcttttgtt ttttcttttc acctgattct | 1020 |
| ctctctgact tgatgtaaga gtggtatctg ctacgactat atgttgtttg ggtgaggcat | 1080 |
| atgtgaatga aatctatgaa agctccggct | 1110 |

<210> SEQ ID NO 2
<211> LENGTH: 38
<212> TYPE: PRT
<213> ORGANISM: Oryza sativa

<400> SEQUENCE: 2

Met Ala Pro Ser Val Met Ala Ser Ser Ala Thr Thr Val Ala Pro Phe
1               5                   10                  15

Gln Gly Ser Ser Pro Pro Pro Ala Cys Arg Arg Pro Pro Ser Glu Leu
            20                  25                  30

Gln Leu Arg Gln Arg Gln
        35

<210> SEQ ID NO 3
<211> LENGTH: 6
<212> TYPE: PRT
<213> ORGANISM: Artificial Sequence
<220> FEATURE:
<223> OTHER INFORMATION: Signal peptide targets the peroxisomes of
      plants

<400> SEQUENCE: 3

Arg Ala Val Ala Arg Leu
1               5

<210> SEQ ID NO 4
<211> LENGTH: 3004
<212> TYPE: DNA
<213> ORGANISM: Acidothermus cellulolyticus
<220> FEATURE:
<221> NAME/KEY: CDS
<222> LOCATION: (824)..(2512)
<223> OTHER INFORMATION: E I beta-1,4-endoglucanase precursor

<400> SEQUENCE: 4

| | |
|---|---|
| ggatccacgt tgtacaaggt cacctgtccg tcgttctggt agagcggcgg gatggtcacc | 60 |
| cgcacgatct ctcctttgtt gatgtcgacg gtcacgtggt tacggtttgc ctcggccgcg | 120 |
| attttcgcgc tcgggcttgc tccggctgtc gggttcggtt tggcgtggtg tgcggagcac | 180 |
| gccgaggcga tcccaatgag ggcaagggca agagcggagc cgatggcacg tcgggtggcc | 240 |
| gatgggtac gccgatgggg cgtggcgtcc ccgccgcgga cagaaccgga tgcggaatag | 300 |
| gtcacggtgc gacatgttgc cgtaccgcgg accggatga caagggtggg tgcgcgggtc | 360 |
| gcctgtgagc tgccggctgg cgtctggatc atgggaacga tcccaccatt ccccgcaatc | 420 |
| gacgcgatcg ggagcagggc ggcgcgagcc ggaccgtgtg gtcgagccgg acgattcgcc | 480 |
| catacggtgc tgcaatgccc agcgccatgt tgtcaatccg ccaaatgcag caatgcacac | 540 |
| atggacaggg attgtgactc tgagtaatga ttggattgcc ttcttgccgc ctacgcgtta | 600 |
| cgcagagtag cgactgtat gcggtaggtt ggcgctccag ccgtgggctg gacatgcctg | 660 |
| ctgcgaactc ttgacacgtc tggttgaacg cgcaatactc caacaccga tgggatcgtt | 720 |
| cccataagtt tccgtctcac aacagaatcg gtgcgccctc atgatcaacg tgaaaggagt | 780 |
| acggggagga acagacgggg gagaaaccaa cgggggattg gcg gtg ccg cgc gca | 835 |
|                                                                   Val Pro Arg Ala | |
|                                                                   1 | |

```
ttg cgg cga gtg cct ggc tcg cgg gtg atg ctg cgg gtc ggc gtc gtc         883
Leu Arg Arg Val Pro Gly Ser Arg Val Met Leu Arg Val Gly Val Val
 5              10                  15                  20 gtc gcg gtg ctg gca ttg gtt gcc gca ctc gcc aac cta gcc gtg ccg         931
Val Ala Val Leu Ala Leu Val Ala Ala Leu Ala Asn Leu Ala Val Pro
                25                  30                  35 cgg ccg gct cgc gcc gcg ggc ggc tat tgg cac acg agc ggc cgg             979
Arg Pro Ala Arg Ala Ala Gly Gly Gly Tyr Trp His Thr Ser Gly Arg
            40                  45                  50 gag atc ctg gac gcg aac aac gtg ccg gta cgg atc gcc ggc atc aac        1027
Glu Ile Leu Asp Ala Asn Asn Val Pro Val Arg Ile Ala Gly Ile Asn
        55                  60                  65 tgg ttt ggg ttc gaa acc tgc aat tac gtc gtg cac ggt ctc tgg tca        1075
Trp Phe Gly Phe Glu Thr Cys Asn Tyr Val Val His Gly Leu Trp Ser
 70                  75                  80 cgc gac tac cgc agc atg ctc gac cag ata aag tcg ctc ggc tac aac        1123
Arg Asp Tyr Arg Ser Met Leu Asp Gln Ile Lys Ser Leu Gly Tyr Asn
85                  90                  95                 100 aca atc cgg ctg ccg tac tct gac gac att ctc aag ccg ggc acc atg        1171
Thr Ile Arg Leu Pro Tyr Ser Asp Asp Ile Leu Lys Pro Gly Thr Met
                105                 110                 115 ccg aac agc atc aat ttt tac cag atg aat cag gac ctg cag ggt ctg        1219
Pro Asn Ser Ile Asn Phe Tyr Gln Met Asn Gln Asp Leu Gln Gly Leu
            120                 125                 130 acg tcc ttg cag gtc atg gac aaa atc gtc gcg tac gcc ggt cag atc        1267
Thr Ser Leu Gln Val Met Asp Lys Ile Val Ala Tyr Ala Gly Gln Ile
        135                 140                 145 ggc ctg cgc atc att ctt gac cgc cac cga ccg gat tgc agc ggg cag        1315
Gly Leu Arg Ile Ile Leu Asp Arg His Arg Pro Asp Cys Ser Gly Gln
    150                 155                 160 tcg gcg ctg tgg tac acg agc agc gtc tcg gag gct acg tgg att tcc        1363
Ser Ala Leu Trp Tyr Thr Ser Ser Val Ser Glu Ala Thr Trp Ile Ser
165                 170                 175                 180 gac ctg caa gcg ctg gcg cag cgc tac aag gga aac ccg acg gtc gtc        1411
Asp Leu Gln Ala Leu Ala Gln Arg Tyr Lys Gly Asn Pro Thr Val Val
                185                 190                 195 ggc ttt gac ttg cac aac gag ccg cat gac ccg gcc tgc tgg ggc tgc        1459
Gly Phe Asp Leu His Asn Glu Pro His Asp Pro Ala Cys Trp Gly Cys
            200                 205                 210 ggc gat ccg agc atc gac tgg cga ttg gcc gcc gag cgg gcc gga aac        1507
Gly Asp Pro Ser Ile Asp Trp Arg Leu Ala Ala Glu Arg Ala Gly Asn
        215                 220                 225 gcc gtg ctc tcg gtg aat ccg aac ctg ctc att ttc gtc gaa ggt gtg        1555
Ala Val Leu Ser Val Asn Pro Asn Leu Leu Ile Phe Val Glu Gly Val
    230                 235                 240 cag agc tac aac gga gac tcc tac tgg tgg ggc ggc aac ctg caa gga        1603
Gln Ser Tyr Asn Gly Asp Ser Tyr Trp Trp Gly Gly Asn Leu Gln Gly
245                 250                 255                 260 gcc ggc cag tac ccg gtc gtg ctg aac gtg ccg aac cgc ctg gtg tac        1651
Ala Gly Gln Tyr Pro Val Val Leu Asn Val Pro Asn Arg Leu Val Tyr
                265                 270                 275 tcg gcg cac gac tac gcg acg agc gtc tac ccg cag acg tgg ttc agc        1699
Ser Ala His Asp Tyr Ala Thr Ser Val Tyr Pro Gln Thr Trp Phe Ser
            280                 285                 290 gat ccg acc ttc ccc aac aac atg ccc ggc atc tgg aac aag aac tgg        1747
Asp Pro Thr Phe Pro Asn Asn Met Pro Gly Ile Trp Asn Lys Asn Trp
        295                 300                 305 gga tac ctc ttc aat cag aac att gca ccg gta tgg ctg ggc gaa ttc        1795
Gly Tyr Leu Phe Asn Gln Asn Ile Ala Pro Val Trp Leu Gly Glu Phe
    310                 315                 320
```

```
ggt acg aca ctg caa tcc acg acc gac cag acg tgg ctg aag acg ctc    1843
Gly Thr Thr Leu Gln Ser Thr Thr Asp Gln Thr Trp Leu Lys Thr Leu
325                 330                 335                 340 gtc cag tac cta cgg ccg acc gcg caa tac ggt gcg gac agc ttc cag    1891
Val Gln Tyr Leu Arg Pro Thr Ala Gln Tyr Gly Ala Asp Ser Phe Gln
            345                 350                 355 tgg acc ttc tgg tcc tgg aac ccc gat tcc ggc gac aca gga gga att    1939
Trp Thr Phe Trp Ser Trp Asn Pro Asp Ser Gly Asp Thr Gly Gly Ile
        360                 365                 370 ctc aag gat gac tgg cag acg gtc gac aca gta aaa gac ggc tat ctc    1987
Leu Lys Asp Asp Trp Gln Thr Val Asp Thr Val Lys Asp Gly Tyr Leu
    375                 380                 385 gcg ccg atc aag tcg tcg att ttc gat cct gtc ggc gcg tct gca tcg    2035
Ala Pro Ile Lys Ser Ser Ile Phe Asp Pro Val Gly Ala Ser Ala Ser
390                 395                 400 cct agc agt caa ccg tcc ccg tcg gtg tcg ccg tct ccg tcg ccg agc    2083
Pro Ser Ser Gln Pro Ser Pro Ser Val Ser Pro Ser Pro Ser Pro Ser
405                 410                 415                 420 ccg tcg gcg agt cgg acg ccg acg cct act ccg acg ccg aca gcc agc    2131
Pro Ser Ala Ser Arg Thr Pro Thr Pro Thr Pro Thr Pro Thr Ala Ser
            425                 430                 435 ccg acg cca acg ctg acc cct act gct acg ccc acg ccc acg gca agc    2179
Pro Thr Pro Thr Leu Thr Pro Thr Ala Thr Pro Thr Pro Thr Ala Ser
        440                 445                 450 ccg acg ccg tca ccg acg gca gcc tcc gga gcc cgc tgc acc gcg agt    2227
Pro Thr Pro Ser Pro Thr Ala Ala Ser Gly Ala Arg Cys Thr Ala Ser
    455                 460                 465 tac cag gtc aac agc gat tgg ggc aat ggc ttc acg gta acg gtg gcc    2275
Tyr Gln Val Asn Ser Asp Trp Gly Asn Gly Phe Thr Val Thr Val Ala
470                 475                 480 gtg aca aat tcc gga tcc gtc gcg acc aag aca tgg acg gtc agt tgg    2323
Val Thr Asn Ser Gly Ser Val Ala Thr Lys Thr Trp Thr Val Ser Trp
485                 490                 495                 500 aca ttc ggc gga aat cag acg att acc aat tcg tgg aat gca gcg gtc    2371
Thr Phe Gly Gly Asn Gln Thr Ile Thr Asn Ser Trp Asn Ala Ala Val
            505                 510                 515 acg cag aac ggt cag tcg gta acg gct cgg aat atg agt tat aac aac    2419
Thr Gln Asn Gly Gln Ser Val Thr Ala Arg Asn Met Ser Tyr Asn Asn
        520                 525                 530 gtg att cag cct ggt cag aac acc acg ttc gga ttc cag gcg agc tat    2467
Val Ile Gln Pro Gly Gln Asn Thr Thr Phe Gly Phe Gln Ala Ser Tyr
    535                 540                 545 acc gga agc aac gcg gca ccg aca gtc gcc tgc gca gca agt taa       2512
Thr Gly Ser Asn Ala Ala Pro Thr Val Ala Cys Ala Ala Ser
550                 555                 560 tacgtcgggg agccgacggg agggtccgga ccgtcggttc cccggcttcc acctatggag  2572
cgaacccaac aatccggacg gaactgcagg taccagagag gaacgacacg aatgcccgcc  2632
atctcaaaac ggctgcgagc cggcgtcctc gccgggcggt gagcatcgc agcctccatc   2692 gtgccgctgg cgatgcagca tcctgccatc gccgcgacgc acgtcgacaa tccctatgcg  2752
ggagcgacct tcttcgtcaa cccgtactgg gcgcaagaag tacagagcga acggcgaacc  2812
agaccaatgc cactctcgca gcgaaaatgc gcgtcgtttc cacatattcg acggccgtct  2872
ggatggaccg catcgctgcg atcaacggcg tcaacggcgg accggcttg acgacatatc  2932 tggacgccgc cctctcccag cagcagggaa ccaccccctga agtcattgag attgtcatct  2992
acgatctgcc gg                                                      3004
```

```
<210> SEQ ID NO 5
<211> LENGTH: 562
<212> TYPE: PRT
<213> ORGANISM: Acidothermus cellulolyticus

<400> SEQUENCE: 5
```

| | | | | | | | | | | | | | | | |
|---|---|---|---|---|---|---|---|---|---|---|---|---|---|---|---|
| Val | Pro | Arg | Ala | Leu | Arg | Arg | Val | Pro | Gly | Ser | Arg | Val | Met | Leu | Arg |
| 1 | | | | 5 | | | | | 10 | | | | | 15 | |
| Val | Gly | Val | Val | Val | Ala | Val | Leu | Ala | Leu | Val | Ala | Ala | Leu | Ala | Asn |
| | | | 20 | | | | | 25 | | | | | 30 | | |
| Leu | Ala | Val | Pro | Arg | Pro | Ala | Arg | Ala | Ala | Gly | Gly | Gly | Tyr | Trp | His |
| | | 35 | | | | | 40 | | | | | 45 | | | |
| Thr | Ser | Gly | Arg | Glu | Ile | Leu | Asp | Ala | Asn | Asn | Val | Pro | Val | Arg | Ile |
| | 50 | | | | | 55 | | | | | 60 | | | | |
| Ala | Gly | Ile | Asn | Trp | Phe | Gly | Phe | Glu | Thr | Cys | Asn | Tyr | Val | Val | His |
| 65 | | | | | 70 | | | | | 75 | | | | | 80 |
| Gly | Leu | Trp | Ser | Arg | Asp | Tyr | Arg | Ser | Met | Leu | Asp | Gln | Ile | Lys | Ser |
| | | | | 85 | | | | | 90 | | | | | 95 | |
| Leu | Gly | Tyr | Asn | Thr | Ile | Arg | Leu | Pro | Tyr | Ser | Asp | Asp | Ile | Leu | Lys |
| | | | 100 | | | | | 105 | | | | | 110 | | |
| Pro | Gly | Thr | Met | Pro | Asn | Ser | Ile | Asn | Phe | Tyr | Gln | Met | Asn | Gln | Asp |
| | | | 115 | | | | | 120 | | | | | 125 | | |
| Leu | Gln | Gly | Leu | Thr | Ser | Leu | Gln | Val | Met | Asp | Lys | Ile | Val | Ala | Tyr |
| | 130 | | | | | 135 | | | | | 140 | | | | |
| Ala | Gly | Gln | Ile | Gly | Leu | Arg | Ile | Ile | Leu | Asp | Arg | His | Arg | Pro | Asp |
| 145 | | | | | 150 | | | | | 155 | | | | | 160 |
| Cys | Ser | Gly | Gln | Ser | Ala | Leu | Trp | Tyr | Thr | Ser | Ser | Val | Ser | Glu | Ala |
| | | | | 165 | | | | | 170 | | | | | 175 | |
| Thr | Trp | Ile | Ser | Asp | Leu | Gln | Ala | Leu | Ala | Gln | Arg | Tyr | Lys | Gly | Asn |
| | | | 180 | | | | | 185 | | | | | 190 | | |
| Pro | Thr | Val | Val | Gly | Phe | Asp | Leu | His | Asn | Glu | Pro | His | Asp | Pro | Ala |
| | | 195 | | | | | 200 | | | | | 205 | | | |
| Cys | Trp | Gly | Cys | Gly | Asp | Pro | Ser | Ile | Asp | Trp | Arg | Leu | Ala | Ala | Glu |
| | 210 | | | | | 215 | | | | | 220 | | | | |
| Arg | Ala | Gly | Asn | Ala | Val | Leu | Ser | Val | Asn | Pro | Asn | Leu | Leu | Ile | Phe |
| 225 | | | | | 230 | | | | | 235 | | | | | 240 |
| Val | Glu | Gly | Val | Gln | Ser | Tyr | Asn | Gly | Asp | Ser | Tyr | Trp | Trp | Gly | Gly |
| | | | | 245 | | | | | 250 | | | | | 255 | |
| Asn | Leu | Gln | Gly | Ala | Gly | Gln | Tyr | Pro | Val | Val | Leu | Asn | Val | Pro | Asn |
| | | | 260 | | | | | 265 | | | | | 270 | | |
| Arg | Leu | Val | Tyr | Ser | Ala | His | Asp | Tyr | Ala | Thr | Ser | Val | Tyr | Pro | Gln |
| | | 275 | | | | | 280 | | | | | 285 | | | |
| Thr | Trp | Phe | Ser | Asp | Pro | Thr | Phe | Pro | Asn | Asn | Met | Pro | Gly | Ile | Trp |
| | 290 | | | | | 295 | | | | | 300 | | | | |
| Asn | Lys | Asn | Trp | Gly | Tyr | Leu | Phe | Asn | Gln | Asn | Ile | Ala | Pro | Val | Trp |
| 305 | | | | | 310 | | | | | 315 | | | | | 320 |
| Leu | Gly | Glu | Phe | Gly | Thr | Thr | Leu | Gln | Ser | Thr | Thr | Asp | Gln | Thr | Trp |
| | | | | 325 | | | | | 330 | | | | | 335 | |
| Leu | Lys | Thr | Leu | Val | Gln | Tyr | Leu | Arg | Pro | Thr | Ala | Gln | Tyr | Gly | Ala |
| | | | 340 | | | | | 345 | | | | | 350 | | |
| Asp | Ser | Phe | Gln | Trp | Thr | Phe | Trp | Ser | Trp | Asn | Pro | Asp | Ser | Gly | Asp |
| | | 355 | | | | | 360 | | | | | 365 | | | |
| Thr | Gly | Gly | Ile | Leu | Lys | Asp | Asp | Trp | Gln | Thr | Val | Asp | Thr | Val | Lys |
| | 370 | | | | | 375 | | | | | 380 | | | | |
| Asp | Gly | Tyr | Leu | Ala | Pro | Ile | Lys | Ser | Ser | Ile | Phe | Asp | Pro | Val | Gly |

```
                385                 390                 395                 400
Ala Ser Ala Ser Pro Ser Ser Gln Pro Ser Pro Ser Val Ser Pro Ser
                    405                 410                 415
Pro Ser Pro Ser Pro Ser Ala Ser Arg Thr Pro Thr Pro Thr Pro Thr
                420                 425                 430
Pro Thr Ala Ser Pro Thr Pro Thr Leu Thr Pro Thr Ala Thr Pro Thr
            435                 440                 445
Pro Thr Ala Ser Pro Thr Pro Ser Pro Thr Ala Ala Ser Gly Ala Arg
        450                 455                 460
Cys Thr Ala Ser Tyr Gln Val Asn Ser Asp Trp Gly Asn Gly Phe Thr
465                 470                 475                 480
Val Thr Val Ala Val Thr Asn Ser Gly Ser Val Ala Thr Lys Thr Trp
                485                 490                 495
Thr Val Ser Trp Thr Phe Gly Gly Asn Gln Thr Ile Thr Asn Ser Trp
                500                 505                 510
Asn Ala Ala Val Thr Gln Asn Gly Gln Ser Val Thr Ala Arg Asn Met
            515                 520                 525
Ser Tyr Asn Asn Val Ile Gln Pro Gly Gln Asn Thr Thr Phe Gly Phe
        530                 535                 540
Gln Ala Ser Tyr Thr Gly Ser Asn Ala Ala Pro Thr Val Ala Cys Ala
545                 550                 555                 560
Ala Ser

<210> SEQ ID NO 6
<211> LENGTH: 1467
<212> TYPE: DNA
<213> ORGANISM: Actinomyces naeslundii
<220> FEATURE:
<221> NAME/KEY: CDS
<222> LOCATION: (1)..(1467)
<223> OTHER INFORMATION: beta-glucosidase
<220> FEATURE:
<221> NAME/KEY: misc_feature
<222> LOCATION: (339)..(339)
<223> OTHER INFORMATION: nucleotide is uncertain
<220> FEATURE:
<221> NAME/KEY: misc_feature
<222> LOCATION: (443)..(443)
<223> OTHER INFORMATION: nucleotide is uncertain
<220> FEATURE:
<221> NAME/KEY: misc_feature
<222> LOCATION: (947)..(947)
<223> OTHER INFORMATION: nucleotide is uncertain

<400> SEQUENCE: 6 atg acc gcc acg tcc act act tct aag agc aat ccg aac ttc ccc gac      48
Met Thr Ala Thr Ser Thr Thr Ser Lys Ser Asn Pro Asn Phe Pro Asp
1               5                   10                  15 ggc ttc ctg tgg ggc ggg gcc acc gcc gcc aac cag atc gag ggc gct      96
Gly Phe Leu Trp Gly Gly Ala Thr Ala Ala Asn Gln Ile Glu Gly Ala
            20                  25                  30 tac aac gag gac ggc aag ggc ctg tcc gtc cag gac gtc atg cct cgg     144
Tyr Asn Glu Asp Gly Lys Gly Leu Ser Val Gln Asp Val Met Pro Arg
        35                  40                  45 ggc atc atg gcc cac ccc acc cag gct ccc aca ccg gat aac ctt caa     192
Gly Ile Met Ala His Pro Thr Gln Ala Pro Thr Pro Asp Asn Leu Gln
    50                  55                  60 gct cga ggc gat cga cct tct acc acc gct tac gcc gag gac atc tcc     240
Ala Arg Gly Asp Arg Pro Ser Thr Thr Ala Tyr Ala Glu Asp Ile Ser
65                  70                  75                  80 ctg ttc gcg gag atg ggt ttc aag gtc ttc cgc ttc tcc atc gcc tgg     288
Leu Phe Ala Glu Met Gly Phe Lys Val Phe Arg Phe Ser Ile Ala Trp
```

```
                       85                    90                       95
agc cgc atc ttc ccg ctc ggc gac gag acc gag ccc aat gag gaa gga                336
Ser Arg Ile Phe Pro Leu Gly Asp Glu Thr Glu Pro Asn Glu Glu Gly
                100                     105                     110 ctn gcc ttc tac gac cgg gtc ctc gac gag ctc gag aag cac ggg atc                384
Xaa Ala Phe Tyr Asp Arg Val Leu Asp Glu Leu Glu Lys His Gly Ile
            115                     120                     125 gag cca ctg gtc acc atc agc cac tac gag acc ccg ctg cac ctg gcg                432
Glu Pro Leu Val Thr Ile Ser His Tyr Glu Thr Pro Leu His Leu Ala
        130                     135                     140 cgc acc tac gnc ggc tgg acc gac cgc cgc ctc atc ggc ttc ttc gag                480
Arg Thr Tyr Xaa Gly Trp Thr Asp Arg Arg Leu Ile Gly Phe Phe Glu
145                     150                     155                     160 cgc tac gcc cgc acc ctg ttc gag cgc tat ggc aag cgg gtc aag tac                528
Arg Tyr Ala Arg Thr Leu Phe Glu Arg Tyr Gly Lys Arg Val Lys Tyr
                165                     170                     175 tgg ctc acc ttc aac gag atc aac tcc gtc ctc cat gag ccc ttc cta                576
Trp Leu Thr Phe Asn Glu Ile Asn Ser Val Leu His Glu Pro Phe Leu
            180                     185                     190 tct ggg ggc gtc gcc acg ccc aag gac agg ccc ccc gag cag gac ctc                624
Ser Gly Gly Val Ala Thr Pro Lys Asp Arg Pro Pro Glu Gln Asp Leu
        195                     200                     205 tac cag gcc atc caa aac gag ctc gtc gcc tcc gcg gcc gcg acc agg                672
Tyr Gln Ala Ile Gln Asn Glu Leu Val Ala Ser Ala Ala Ala Thr Arg
    210                     215                     220 atc gcc cat gag acc aac ccc gac atc cag gtc ggc tgc atg atc ctg                720
Ile Ala His Glu Thr Asn Pro Asp Ile Gln Val Gly Cys Met Ile Leu
225                     230                     235                     240 gcc gat ccc acc tac ccg ctc acc cct gat ccc cgg gac gtg tgg gcg                768
Ala Asp Pro Thr Tyr Pro Leu Thr Pro Asp Pro Arg Asp Val Trp Ala
                245                     250                     255 gcc aag cag gca gag cgc gcc aac tac gcc ttc gga gac ctc cac gta                816
Ala Lys Gln Ala Glu Arg Ala Asn Tyr Ala Phe Gly Asp Leu His Val
            260                     265                     270 cgt ggt gag tac ccc gga tac ctg cgg cgg acc ctg cgg gac aag ggc                864
Arg Gly Glu Tyr Pro Gly Tyr Leu Arg Arg Thr Leu Arg Asp Lys Gly
        275                     280                     285 atc gag ctg gag atc acc gag gag gac cgc gtg ctg ctg cgg gag cac                912
Ile Glu Leu Glu Ile Thr Glu Glu Asp Arg Val Leu Leu Arg Glu His
    290                     295                     300 acc gtc gac ttc gtc tcc ttc tcc tac tac atg tnc gtg tgc gag acc                960
Thr Val Asp Phe Val Ser Phe Ser Tyr Tyr Met Xaa Val Cys Glu Thr
305                     310                     315                     320 gtc acc cag tcg gcc gag gcc ggc cgg ggc aac ctc atg ggc ggc gtc               1008
Val Thr Gln Ser Ala Glu Ala Gly Arg Gly Asn Leu Met Gly Gly Val
                325                     330                     335 ccc aat ccc acc ctc gag gcc tcc gag tgg gga tgg cag atc gac ccg               1056
Pro Asn Pro Thr Leu Glu Ala Ser Glu Trp Gly Trp Gln Ile Asp Pro
            340                     345                     350 gcg ggc ctg cgc acc atc ctg aac gac tac tgg gac cgc tgg ggc aag               1104
Ala Gly Leu Arg Thr Ile Leu Asn Asp Tyr Trp Asp Arg Trp Gly Lys
        355                     360                     365 cct ctg ttc atc gtc gag aac ggc ctg gga gcc aag gac gtc ctc gtt               1152
Pro Leu Phe Ile Val Glu Asn Gly Leu Gly Ala Lys Asp Val Leu Val
    370                     375                     380 gac gga ccc aac ggt ccc acg gtc gag gac gac tac cgc atc gcc tac               1200
Asp Gly Pro Asn Gly Pro Thr Val Glu Asp Asp Tyr Arg Ile Ala Tyr
385                     390                     395                     400 atg aac gac cac ctg gtc cag gtc gcc gag gcc att gcc gac ggc gtc               1248
Met Asn Asp His Leu Val Gln Val Ala Glu Ala Ile Ala Asp Gly Val
```

```
                405                 410                 415
gag gtc ctg ggc tac acc tcc tgg ggc tgc atc gac ctg gtc tcg gcc       1296
Glu Val Leu Gly Tyr Thr Ser Trp Gly Cys Ile Asp Leu Val Ser Ala
        420                 425                 430 tcc acc gcc cag atg tcc aag cgc tac ggg ttc atc tac gtg gac cgt       1344
Ser Thr Ala Gln Met Ser Lys Arg Tyr Gly Phe Ile Tyr Val Asp Arg
        435                 440                 445 gac gac ggc ggc aac ggc acc ctg gcc cgc tac cgc aag aag tcc ttc       1392
Asp Asp Gly Gly Asn Gly Thr Leu Ala Arg Tyr Arg Lys Lys Ser Phe
    450                 455                 460 ggc tgg tac cgc gac gtc atc gcc tcc aac ggt gcc tcc ctc gtg cct       1440
Gly Trp Tyr Arg Asp Val Ile Ala Ser Asn Gly Ala Ser Leu Val Pro
465                 470                 475                 480 ccg gtg cag gaa ccg ccg cgg ggg tag                                   1467
Pro Val Gln Glu Pro Pro Arg Gly
                485
```

<210> SEQ ID NO 7
<211> LENGTH: 488
<212> TYPE: PRT
<213> ORGANISM: Actinomyces naeslundii
<220> FEATURE:
<221> NAME/KEY: misc_feature
<222> LOCATION: (113)..(113)
<223> OTHER INFORMATION: The 'Xaa' at location 113 stands for Leu.
<220> FEATURE:
<221> NAME/KEY: misc_feature
<222> LOCATION: (148)..(148)
<223> OTHER INFORMATION: The 'Xaa' at location 148 stands for Asp, Gly,
      Ala, or Val.
<220> FEATURE:
<221> NAME/KEY: misc_feature
<222> LOCATION: (316)..(316)
<223> OTHER INFORMATION: The 'Xaa' at location 316 stands for Tyr, Cys,
      Ser, or Phe.

<400> SEQUENCE: 7

```
Met Thr Ala Thr Ser Thr Thr Ser Lys Ser Asn Pro Asn Phe Pro Asp
1               5                   10                  15

Gly Phe Leu Trp Gly Gly Ala Thr Ala Ala Asn Gln Ile Glu Gly Ala
            20                  25                  30

Tyr Asn Glu Asp Gly Lys Gly Leu Ser Val Gln Asp Val Met Pro Arg
        35                  40                  45

Gly Ile Met Ala His Pro Thr Gln Ala Pro Thr Pro Asp Asn Leu Gln
    50                  55                  60

Ala Arg Gly Asp Arg Pro Ser Thr Thr Ala Tyr Ala Glu Asp Ile Ser
65                  70                  75                  80

Leu Phe Ala Glu Met Gly Phe Lys Val Phe Arg Phe Ser Ile Ala Trp
                85                  90                  95

Ser Arg Ile Phe Pro Leu Gly Asp Glu Thr Glu Pro Asn Glu Glu Gly
            100                 105                 110

Xaa Ala Phe Tyr Asp Arg Val Leu Asp Glu Leu Glu Lys His Gly Ile
        115                 120                 125

Glu Pro Leu Val Thr Ile Ser His Tyr Glu Thr Pro Leu His Leu Ala
    130                 135                 140

Arg Thr Tyr Xaa Gly Trp Thr Asp Arg Arg Leu Ile Gly Phe Phe Glu
145                 150                 155                 160

Arg Tyr Ala Arg Thr Leu Phe Glu Arg Tyr Gly Lys Arg Val Lys Tyr
                165                 170                 175

Trp Leu Thr Phe Asn Glu Ile Asn Ser Val Leu His Glu Pro Phe Leu
            180                 185                 190
```

```
Ser Gly Gly Val Ala Thr Pro Lys Asp Arg Pro Pro Glu Gln Asp Leu
        195                 200                 205

Tyr Gln Ala Ile Gln Asn Glu Leu Val Ala Ser Ala Ala Thr Arg
    210                 215                 220

Ile Ala His Glu Thr Asn Pro Asp Ile Gln Val Gly Cys Met Ile Leu
225                 230                 235                 240

Ala Asp Pro Thr Tyr Pro Leu Thr Pro Asp Pro Arg Asp Val Trp Ala
                245                 250                 255

Ala Lys Gln Ala Glu Arg Ala Asn Tyr Ala Phe Gly Asp Leu His Val
            260                 265                 270

Arg Gly Glu Tyr Pro Gly Tyr Leu Arg Arg Thr Leu Arg Asp Lys Gly
        275                 280                 285

Ile Glu Leu Glu Ile Thr Glu Glu Asp Arg Val Leu Leu Arg Glu His
290                 295                 300

Thr Val Asp Phe Val Ser Phe Ser Tyr Tyr Met Xaa Val Cys Glu Thr
305                 310                 315                 320

Val Thr Gln Ser Ala Glu Ala Gly Arg Gly Asn Leu Met Gly Gly Val
                325                 330                 335

Pro Asn Pro Thr Leu Glu Ala Ser Glu Trp Gly Trp Gln Ile Asp Pro
            340                 345                 350

Ala Gly Leu Arg Thr Ile Leu Asn Asp Tyr Trp Asp Arg Trp Gly Lys
        355                 360                 365

Pro Leu Phe Ile Val Glu Asn Gly Leu Gly Ala Lys Asp Val Leu Val
370                 375                 380

Asp Gly Pro Asn Gly Pro Thr Val Glu Asp Tyr Arg Ile Ala Tyr
385                 390                 395                 400

Met Asn Asp His Leu Val Gln Val Ala Glu Ala Ile Ala Asp Gly Val
                405                 410                 415

Glu Val Leu Gly Tyr Thr Ser Trp Gly Cys Ile Asp Leu Val Ser Ala
            420                 425                 430

Ser Thr Ala Gln Met Ser Lys Arg Tyr Gly Phe Ile Tyr Val Asp Arg
        435                 440                 445

Asp Asp Gly Gly Asn Gly Thr Leu Ala Arg Tyr Arg Lys Lys Ser Phe
450                 455                 460

Gly Trp Tyr Arg Asp Val Ile Ala Ser Asn Gly Ala Ser Leu Val Pro
465                 470                 475                 480

Pro Val Gln Glu Pro Pro Arg Gly
                485

<210> SEQ ID NO 8
<211> LENGTH: 3072
<212> TYPE: DNA
<213> ORGANISM: Streptococcus salivarius
<220> FEATURE:
<221> NAME/KEY: CDS
<222> LOCATION: (392)..(2860)
<223> OTHER INFORMATION: 1,6-alpha-glucanhydrolase

<400> SEQUENCE: 8
aactgaggcc gttgctccag tagcgacaac agaaataggt ccatcaactg ctactgttgc    60
gacagatact gcaacaacag cgacagcttc tacaatcttt tcacaagctg tgccagcaga   120
aagtgctagc tcagaaacgc ttgtagccag tgaagcacta gctcctgagt cagctgctgt   180
ggaaaccatc acatcatcat ctgataatgc tactgaagca ggacgccatt caactgctca   240
agtaacacca gttacagaag tgacagagca aaacttgaat ggtgatgcct acttgacaga   300
tccagaaaca acaaaagcag cttatagcaa gacagatggt gatattaatt attccgttgt   360
```

```
tgtgtctaat ccaacagcag aaactaagac g atg act gtc aac ttg aca ctt        412
                                   Met Thr Val Asn Leu Thr Leu
                                    1               5 caa cat gct tca gaa att atc ggt caa gat aac gtt gac ctt acg cta       460
Gln His Ala Ser Glu Ile Ile Gly Gln Asp Asn Val Asp Leu Thr Leu
         10              15                  20 gcg gca gga gct tca gcc aag gtt tca aac ttg aca gta gcg tca gag       508
Ala Ala Gly Ala Ser Ala Lys Val Ser Asn Leu Thr Val Ala Ser Glu
 25              30                  35 tgg ttg aca aac aat aca ggt tac ttg gtg aca atc agt gtc aac gat       556
Trp Leu Thr Asn Asn Thr Gly Tyr Leu Val Thr Ile Ser Val Asn Asp
40              45                  50                  55 aaa tca ggc aat gtc ttg tca agc aag cgc gct ggc ttg tct gtt gaa       604
Lys Ser Gly Asn Val Leu Ser Ser Lys Arg Ala Gly Leu Ser Val Glu
                60                  65                  70 gat gat tgg aca gtt ttc cca cgt tac ggt atc gta gca ggt tca cca       652
Asp Asp Trp Thr Val Phe Pro Arg Tyr Gly Ile Val Ala Gly Ser Pro
             75                  80                  85 act gat caa aac agt att ctt gtt aaa aat ctt gaa gcc tac cgt aaa       700
Thr Asp Gln Asn Ser Ile Leu Val Lys Asn Leu Glu Ala Tyr Arg Lys
         90                  95                 100 gag ctt gag ctc atg aag tct atg aat atc aac tca tat ttc ttc tat       748
Glu Leu Glu Leu Met Lys Ser Met Asn Ile Asn Ser Tyr Phe Phe Tyr
    105                 110                 115 gat gct tat aat gaa gct aca gat cct ttc cca gaa ggt gtc gat agc       796
Asp Ala Tyr Asn Glu Ala Thr Asp Pro Phe Pro Glu Gly Val Asp Ser
120                 125                 130                 135 ttt gtt caa aaa tgg aat acc tgg agt cac act cag gtt gac act aag       844
Phe Val Gln Lys Trp Asn Thr Trp Ser His Thr Gln Val Asp Thr Lys
                140                 145                 150 gct gtt aaa gaa ttg gtt gat caa gtt cat aag tca ggt gct gtt gcc       892
Ala Val Lys Glu Leu Val Asp Gln Val His Lys Ser Gly Ala Val Ala
            155                 160                 165 atg ctt tat aac atg att tca gca gat tca aat cca aag aat ccg gcc       940
Met Leu Tyr Asn Met Ile Ser Ala Asp Ser Asn Pro Lys Asn Pro Ala
        170                 175                 180 ctt cca ctt gct gct ttg gct tat aac ttc tac gat agc ttt ggt aag       988
Leu Pro Leu Ala Ala Leu Ala Tyr Asn Phe Tyr Asp Ser Phe Gly Lys
    185                 190                 195 aag ggt gaa ccg atg act tac act atc ggt gat aac cca act caa gtt      1036
Lys Gly Glu Pro Met Thr Tyr Thr Ile Gly Asp Asn Pro Thr Gln Val
200                 205                 210                 215 tac tat gat ccg gcg aat cca gat tgg caa aaa tac atc gca ggt gtc      1084
Tyr Tyr Asp Pro Ala Asn Pro Asp Trp Gln Lys Tyr Ile Ala Gly Val
                220                 225                 230 atg aaa tca gct atg gat cgt atg gga ttc gat ggt tgg caa ggt gat      1132
Met Lys Ser Ala Met Asp Arg Met Gly Phe Asp Gly Trp Gln Gly Asp
            235                 240                 245 aca att ggt gac aac cgt gtg act gat tat gag cac cgt aac agc aca      1180
Thr Ile Gly Asp Asn Arg Val Thr Asp Tyr Glu His Arg Asn Ser Thr
        250                 255                 260 gac gag gct gac tca cac atg atg tct gat tca tat gcg tca ttt att      1228
Asp Glu Ala Asp Ser His Met Met Ser Asp Ser Tyr Ala Ser Phe Ile
    265                 270                 275 aat gcc atg aag gac ctc atc ggt gaa aag tac tac atc aca atc aat      1276
Asn Ala Met Lys Asp Leu Ile Gly Glu Lys Tyr Tyr Ile Thr Ile Asn
280                 285                 290                 295 gat gtt aat ggt ggt aat gat gat aaa cta gcc aag gca cgt caa gat      1324
Asp Val Asn Gly Gly Asn Asp Asp Lys Leu Ala Lys Ala Arg Gln Asp
                300                 305                 310
```

| | |
|---|---|
| gtt gtt tat aat gag ctt tgg aca aac ggt ggt tca gtt att cca gga<br>Val Val Tyr Asn Glu Leu Trp Thr Asn Gly Gly Ser Val Ile Pro Gly<br>             315                      320                   325 | 1372 |
| cgt atg cag gtt gcc tat ggt gat ttg aaa gca cgt atc gat atg gta<br>Arg Met Gln Val Ala Tyr Gly Asp Leu Lys Ala Arg Ile Asp Met Val<br>330                      335                      340 | 1420 |
| cgc aat aaa act ggt aaa tca ctt atc gtt ggt gcc tac atg gaa gaa<br>Arg Asn Lys Thr Gly Lys Ser Leu Ile Val Gly Ala Tyr Met Glu Glu<br>             345                      350                   355 | 1468 |
| cca ggg att gat tat act gtt cct ggc gga aaa gca act aac ggt gct<br>Pro Gly Ile Asp Tyr Thr Val Pro Gly Gly Lys Ala Thr Asn Gly Ala<br>360                      365                      370                  375 | 1516 |
| ggt aaa gat gcc ctt gct ggt aaa cca ttg caa gct gat gcg act ctt<br>Gly Lys Asp Ala Leu Ala Gly Lys Pro Leu Gln Ala Asp Ala Thr Leu<br>                   380                      385                      390 | 1564 |
| ctc gta gat gcg aca gta gct gca gca ggt ggt tat cac atg tcc att<br>Leu Val Asp Ala Thr Val Ala Ala Ala Gly Gly Tyr His Met Ser Ile<br>             395                      400                   405 | 1612 |
| gca gcc ctt gca aat gct aat gcg gcc ctt aac gtc ctt caa agt gcc<br>Ala Ala Leu Ala Asn Ala Asn Ala Ala Leu Asn Val Leu Gln Ser Ala<br>410                      415                      420 | 1660 |
| tat tac cca acg caa tac ctc agt gtg gct aaa gac act att cgt aag<br>Tyr Tyr Pro Thr Gln Tyr Leu Ser Val Ala Lys Asp Thr Ile Arg Lys<br>         425                      430                      435 | 1708 |
| ctt tac aat tac caa cag ttt atc act gct tat gaa aat ctc ctc cgc<br>Leu Tyr Asn Tyr Gln Gln Phe Ile Thr Ala Tyr Glu Asn Leu Leu Arg<br>440                      445                      450                   455 | 1756 |
| ggt gag ggt gtg aca aac agc act cag gct gta tct aca aag aat gct<br>Gly Glu Gly Val Thr Asn Ser Thr Gln Ala Val Ser Thr Lys Asn Ala<br>                   460                      465                   470 | 1804 |
| tct ggt gaa atc ctt tct aaa gat gct ctt ggt gtg aca gga gat caa<br>Ser Gly Glu Ile Leu Ser Lys Asp Ala Leu Gly Val Thr Gly Asp Gln<br>             475                      480                   485 | 1852 |
| gtt tgg aca ttt gct aaa tca gga aaa ggt ttc tca act gtt caa atg<br>Val Trp Thr Phe Ala Lys Ser Gly Lys Gly Phe Ser Thr Val Gln Met<br>                   490                      495                   500 | 1900 |
| att aat atg atg ggc atc aat gcg ggc tgg cat aat gaa gag ggt tat<br>Ile Asn Met Met Gly Ile Asn Ala Gly Trp His Asn Glu Glu Gly Tyr<br>505                      510                      515 | 1948 |
| gcg gac aat aaa aca ccg gac gca caa gaa aat ctc aca gtt cgt ctt<br>Ala Asp Asn Lys Thr Pro Asp Ala Gln Glu Asn Leu Thr Val Arg Leu<br>520                      525                      530                   535 | 1996 |
| agc cta gca ggt aaa aca gcc caa gaa gca gct aaa att gct gat caa<br>Ser Leu Ala Gly Lys Thr Ala Gln Glu Ala Ala Lys Ile Ala Asp Gln<br>                   540                      545                   550 | 2044 |
| gtc tat gtg acg tca ccg gat gat tgg gca act tca agc atg aag aag<br>Val Tyr Val Thr Ser Pro Asp Asp Trp Ala Thr Ser Ser Met Lys Lys<br>             555                      560                   565 | 2092 |
| gca caa gca agc ctt gaa aca gat gaa aat ggt caa cca gtg ctt gtc<br>Ala Gln Ala Ser Leu Glu Thr Asp Glu Asn Gly Gln Pro Val Leu Val<br>                 570                      575                   580 | 2140 |
| att tca gtt cct aaa cta act ctt tgg aac atg ctt tat atc aag gaa<br>Ile Ser Val Pro Lys Leu Thr Leu Trp Asn Met Leu Tyr Ile Lys Glu<br>585                      590                      595 | 2188 |
| gac aca aca gca aca ccg gta gaa cca gtt act aac caa gct ggt aag<br>Asp Thr Thr Ala Thr Pro Val Glu Pro Val Thr Asn Gln Ala Gly Lys<br>600                      605                      610                   615 | 2236 |
| aaa gta gat aat acc gta aca tct gaa gca agc tca gaa aca gct aaa<br>Lys Val Asp Asn Thr Val Thr Ser Glu Ala Ser Ser Glu Thr Ala Lys<br>                   620                      625                   630 | 2284 |

```
tca gaa aat aca aca gta aat aaa ggt tca gag gct cca act gat acg    2332
Ser Glu Asn Thr Thr Val Asn Lys Gly Ser Glu Ala Pro Thr Asp Thr
            635                 640                 645 aaa cca tct gtt gaa gct cct aaa cta gat gaa aca act aaa cca gca    2380
Lys Pro Ser Val Glu Ala Pro Lys Leu Asp Glu Thr Thr Lys Pro Ala
    650                 655                 660 cca tca gtt gac gag tta gta aac tca gca gct gtt cca gtg gcg ata    2428
Pro Ser Val Asp Glu Leu Val Asn Ser Ala Ala Val Pro Val Ala Ile
665                 670                 675 gct gtg tca gag acc gca cat gat aag aaa gat gac aac tca gta tct    2476
Ala Val Ser Glu Thr Ala His Asp Lys Lys Asp Asp Asn Ser Val Ser
680                 685                 690                 695 aat acg gat caa ggt aca gta gca tca gat tca atc act aca cca gct    2524
Asn Thr Asp Gln Gly Thr Val Ala Ser Asp Ser Ile Thr Thr Pro Ala
            700                 705                 710 tca gag gct gca agc aca gct gcc tca aca gtc tca tca gaa gta tca    2572
Ser Glu Ala Ala Ser Thr Ala Ala Ser Thr Val Ser Ser Glu Val Ser
    715                 720                 725 gaa agt gta aca gta tca tcg gaa cca tca gaa act gaa aat agt tca    2620
Glu Ser Val Thr Val Ser Ser Glu Pro Ser Glu Thr Glu Asn Ser Ser
730                 735                 740 gaa gca tca act tca gag tca gca act cca acg acg aca gca att tca    2668
Glu Ala Ser Thr Ser Glu Ser Ala Thr Pro Thr Thr Thr Ala Ile Ser
745                 750                 755 gaa tca cat gca gta gtt gaa cca gtg gct tct ttg aca gaa tca gag    2716
Glu Ser His Ala Val Val Glu Pro Val Ala Ser Leu Thr Glu Ser Glu
760                 765                 770                 775 agt cag gca agc act agc ctt gtt tca gaa act aca agc aca att gtc    2764
Ser Gln Ala Ser Thr Ser Leu Val Ser Glu Thr Thr Ser Thr Ile Val
            780                 785                 790 tca gtt gct ccg tca gaa gta tca gaa agc aca tca gag gaa gtc atc    2812
Ser Val Ala Pro Ser Glu Val Ser Glu Ser Thr Ser Glu Glu Val Ile
    795                 800                 805 ctt atg gac tat cag aaa aca tca ata gtt gga ata gac tct ctg tag    2860
Leu Met Asp Tyr Gln Lys Thr Ser Ile Val Gly Ile Asp Ser Leu
810                 815                 820 ctcctcgcgt ctcagaaacc ttaccaagta cttctgaaac gattacagaa gcagcatcac    2920
tctttagcaa ctatgcaaga tattcagaaa cagcaagctc agaatctcac tctatggtag    2980
cagcttcttc agaagtttct attgaaaaat tagcagtatc tatcttgaaa gatactgagg    3040
gaggcttgta tgatgcaaca acaatcagaa at                                  3072

<210> SEQ ID NO 9
<211> LENGTH: 822
<212> TYPE: PRT
<213> ORGANISM: Streptococcus salivarius

<400> SEQUENCE: 9

Met Thr Val Asn Leu Thr Leu Gln His Ala Ser Glu Ile Ile Gly Gln
1               5                   10                  15

Asp Asn Val Asp Leu Thr Leu Ala Ala Gly Ala Ser Ala Lys Val Ser
            20                  25                  30

Asn Leu Thr Val Ala Ser Glu Trp Leu Thr Asn Asn Thr Gly Tyr Leu
        35                  40                  45

Val Thr Ile Ser Val Asn Asp Lys Ser Gly Asn Val Leu Ser Ser Lys
    50                  55                  60

Arg Ala Gly Leu Ser Val Glu Asp Asp Trp Thr Val Phe Pro Arg Tyr
65                  70                  75                  80
```

```
Gly Ile Val Ala Gly Ser Pro Thr Asp Gln Asn Ser Ile Leu Val Lys
                85                  90                  95
Asn Leu Glu Ala Tyr Arg Lys Glu Leu Glu Leu Met Lys Ser Met Asn
            100                 105                 110
Ile Asn Ser Tyr Phe Phe Tyr Asp Ala Tyr Asn Glu Ala Thr Asp Pro
        115                 120                 125
Phe Pro Glu Gly Val Asp Ser Phe Val Gln Lys Trp Asn Thr Trp Ser
    130                 135                 140
His Thr Gln Val Asp Thr Lys Ala Val Lys Glu Leu Val Asp Gln Val
145                 150                 155                 160
His Lys Ser Gly Ala Val Ala Met Leu Tyr Asn Met Ile Ser Ala Asp
                165                 170                 175
Ser Asn Pro Lys Asn Pro Ala Leu Pro Leu Ala Ala Leu Ala Tyr Asn
            180                 185                 190
Phe Tyr Asp Ser Phe Gly Lys Lys Gly Glu Pro Met Thr Tyr Thr Ile
        195                 200                 205
Gly Asp Asn Pro Thr Gln Val Tyr Tyr Asp Pro Ala Asn Pro Asp Trp
    210                 215                 220
Gln Lys Tyr Ile Ala Gly Val Met Lys Ser Ala Met Asp Arg Met Gly
225                 230                 235                 240
Phe Asp Gly Trp Gln Gly Asp Thr Ile Gly Asp Asn Arg Val Thr Asp
                245                 250                 255
Tyr Glu His Arg Asn Ser Thr Asp Glu Ala Asp Ser His Met Met Ser
            260                 265                 270
Asp Ser Tyr Ala Ser Phe Ile Asn Ala Met Lys Asp Leu Ile Gly Glu
        275                 280                 285
Lys Tyr Tyr Ile Thr Ile Asn Asp Val Asn Gly Gly Asn Asp Asp Lys
    290                 295                 300
Leu Ala Lys Ala Arg Gln Asp Val Val Tyr Asn Glu Leu Trp Thr Asn
305                 310                 315                 320
Gly Gly Ser Val Ile Pro Gly Arg Met Gln Val Ala Tyr Gly Asp Leu
                325                 330                 335
Lys Ala Arg Ile Asp Met Val Arg Asn Lys Thr Gly Lys Ser Leu Ile
            340                 345                 350
Val Gly Ala Tyr Met Glu Glu Pro Gly Ile Asp Tyr Thr Val Pro Gly
        355                 360                 365
Gly Lys Ala Thr Asn Gly Ala Gly Lys Asp Ala Leu Ala Gly Lys Pro
    370                 375                 380
Leu Gln Ala Asp Ala Thr Leu Leu Val Asp Ala Thr Val Ala Ala Ala
385                 390                 395                 400
Gly Gly Tyr His Met Ser Ile Ala Ala Leu Ala Asn Ala Asn Ala Ala
                405                 410                 415
Leu Asn Val Leu Gln Ser Ala Tyr Tyr Pro Thr Gln Tyr Leu Ser Val
            420                 425                 430
Ala Lys Asp Thr Ile Arg Lys Leu Tyr Asn Tyr Gln Gln Phe Ile Thr
        435                 440                 445
Ala Tyr Glu Asn Leu Leu Arg Gly Glu Gly Val Thr Asn Ser Thr Gln
    450                 455                 460
Ala Val Ser Thr Lys Asn Ala Ser Gly Glu Ile Leu Ser Lys Asp Ala
465                 470                 475                 480
Leu Gly Val Thr Gly Asp Gln Val Trp Thr Phe Ala Lys Ser Gly Lys
                485                 490                 495
Gly Phe Ser Thr Val Gln Met Ile Asn Met Met Gly Ile Asn Ala Gly
            500                 505                 510
```

```
Trp His Asn Glu Glu Gly Tyr Ala Asp Asn Lys Thr Pro Asp Ala Gln
            515                 520                 525

Glu Asn Leu Thr Val Arg Leu Ser Leu Ala Gly Lys Thr Ala Gln Glu
        530                 535                 540

Ala Ala Lys Ile Ala Asp Gln Val Tyr Val Thr Ser Pro Asp Asp Trp
545                 550                 555                 560

Ala Thr Ser Ser Met Lys Lys Ala Gln Ala Ser Leu Glu Thr Asp Glu
                565                 570                 575

Asn Gly Gln Pro Val Leu Val Ile Ser Val Pro Lys Leu Thr Leu Trp
            580                 585                 590

Asn Met Leu Tyr Ile Lys Glu Asp Thr Thr Ala Thr Pro Val Glu Pro
        595                 600                 605

Val Thr Asn Gln Ala Gly Lys Lys Val Asp Asn Thr Val Thr Ser Glu
    610                 615                 620

Ala Ser Ser Glu Thr Ala Lys Ser Glu Asn Thr Thr Val Asn Lys Gly
625                 630                 635                 640

Ser Glu Ala Pro Thr Asp Thr Lys Pro Ser Val Glu Ala Pro Lys Leu
                645                 650                 655

Asp Glu Thr Thr Lys Pro Ala Pro Ser Val Asp Glu Leu Val Asn Ser
            660                 665                 670

Ala Ala Val Pro Val Ala Ile Ala Val Ser Glu Thr Ala His Asp Lys
        675                 680                 685

Lys Asp Asp Asn Ser Val Ser Asn Thr Asp Gln Gly Thr Val Ala Ser
    690                 695                 700

Asp Ser Ile Thr Thr Pro Ala Ser Glu Ala Ala Ser Thr Ala Ala Ser
705                 710                 715                 720

Thr Val Ser Ser Glu Val Ser Glu Ser Val Thr Val Ser Ser Glu Pro
                725                 730                 735

Ser Glu Thr Glu Asn Ser Ser Glu Ala Ser Thr Ser Glu Ser Ala Thr
            740                 745                 750

Pro Thr Thr Thr Ala Ile Ser Glu Ser His Ala Val Val Glu Pro Val
        755                 760                 765

Ala Ser Leu Thr Glu Ser Glu Ser Gln Ala Ser Thr Ser Leu Val Ser
    770                 775                 780

Glu Thr Thr Ser Thr Ile Val Ser Val Ala Pro Ser Glu Val Ser Glu
785                 790                 795                 800

Ser Thr Ser Glu Glu Val Ile Leu Met Asp Tyr Gln Lys Thr Ser Ile
                805                 810                 815

Val Gly Ile Asp Ser Leu
            820

<210> SEQ ID NO 10
<211> LENGTH: 2220
<212> TYPE: DNA
<213> ORGANISM: Trichoderma longibrachiatum

<400> SEQUENCE: 10
aaggttagcc aagaacaata gccgataaag atagcctcat taaacggaat gagctagtag      60
gcaaagtcag cgaatgtgta tatataaagg ttcgaggtcc gtgcctccct catgctctcc     120
ccatctactc atcaactcag atcctccagg agacttgtac accatctttt gaggcacaga     180
aacccaatag tcaaccgcgg actggcatca tgtatcggaa gttggccgtc atcacggcct     240
tcttggccac agtcgtgct cagtcggcct gcactctcca atcggagact cacccgcctc     300
tgacatggca gaaatgctcg tctggtggca cttgcactca acagacaggc tccgtggtca     360
```

```
tcgacgccaa ctggcgctgg actcacgcta cgaacagcag cacgaactgc tacgatggca      420
acacttggag ctcgacccta tgtcctgaca acgagacctg cgcgaagaac tgctgtctgg      480
acggtgccgc ctacgcgtcc acgtacggag ttaccacgag cggtaacagc ctctccattg      540
gctttgtcac ccagtctgcg cagaagaacg ttggcgctcg cctttacctt atggcgagcg      600
acacgaccta ccaggaattc accctgcttg caacgagtt ctctttcgat gttgatgttt       660
cgcagctgcc gtaagtgact taccatgaac ccctgacgta tcttcttgtg ggctcccagc      720
tgactggcca atttaaggtg cggcttgaac ggagctctct acttcgtgtc catggacgcg      780
gatggtggcg tgagcaagta tcccaccaac aacgctggcg ccaagtacgg cacggggtac      840
tgtgacagcc agtgtccccg cgatctgaag ttcatcaatg ccaggccaa cgttgagggc       900 tgggagccgt catccaacaa cgcaaacacg ggcattggag acacggaag ctgctgctct       960 gagatggata tctgggaggc caactccatc tccgaggctc ttaccccca cccttgcacg      1020 actgtcggcc aggagatctg cgagggtgat gggtgcggcg gaacttactc cgataacaga     1080
tatggcggca cttgcgatcc cgatggctgc gactggaacc cataccgcct gggcaacacc     1140
agcttctacg ccctggctc aagctttacc ctcgatacca ccaagaaatt gaccgttgtc      1200
acccagttcg agacgtcggg tgccatcaac cgatactatg tccagaatgg cgtcactttc     1260
cagcagccca acgccgagct tggtagttac tctggcaacg agctcaacga tgattactgc     1320
acagctgagg agacagaatt cggcggatct ctttctcaga caagggcggc ctgactcagt     1380
tcaagaaggc tacctctggc ggcatggttc tggtcatgag tctgtgggat gatgtgagtt     1440
tgatggacaa acatgcgcgt tgacaaagag tcaagcagct gactgagatg ttacagtact     1500
acgccaacat gctgtggctg gactccacct acccgacaaa cgagacctcc tccacacccg     1560
gtgccgtgcg cggaagctgc tccaccagct ccggtgtccc tgctcaggtc gaatctcagt     1620
ctcccaacgc caaggtcacc ttctccaaca tcaagttcgg acccattggc agcaccggca     1680
accctagcgg cggcaacct cccggcggaa accgtggcac caccaccacc cgccgcccag      1740
ccactaccac tggaagctct cccggaccta cccagtctca ctacggccag tgcggcggta     1800
ttggctacag cggcccacg gtctgcgcca gcggcacaac ttgccaggtc ctgaaccctt      1860
actactctca gtgcctgtaa agctccgtgc gaaagcctga cgcaccggta gattcttggt     1920
gagcccgtat catgacggcg gcgggagcta catggccccg ggtgatttat tttttttgta     1980
tctacttctg acccttttca aatatacggt caactcatct ttcactggag atgcggcctg     2040
cttggtattg cgatgttgtc agcttggcaa attgtggctt tcgaaaacac aaaacgattc     2100
cttagtagcc atgcattta agataacgga ataagaaaa gaggaaatta aaaaaaaaaa       2160 aaaacaaac atcccgttca taacccgtag aatcgccgct cttcgtgtat cccagtacca     2220
```

<210> SEQ ID NO 11
<211> LENGTH: 1263
<212> TYPE: DNA
<213> ORGANISM: Phanerochaete chrysosporium
<220> FEATURE:
<221> NAME/KEY: CDS
<222> LOCATION: (34)..(1152)
<223> OTHER INFORMATION: ckg4 ligninase precursor

<400> SEQUENCE: 11

```
gctacagctc accgtccggt ctcagcagca gca atg gcg ttc aag cag ctc ctc       54
                                    Met Ala Phe Lys Gln Leu Leu
                                     1               5 gca gcc ctc tcc gtc gcc ctg acc ctc cag gtc acc caa gct gcc ccg       102
```

```
        Ala Ala Leu Ser Val Ala Leu Thr Leu Gln Val Thr Gln Ala Ala Pro
                    10                  15                  20 aac ctc gac aag cgc gtc gct tgc ccc gac ggc gtg cac acc gcc tcc        150
Asn Leu Asp Lys Arg Val Ala Cys Pro Asp Gly Val His Thr Ala Ser
 25                  30                  35 aac gcg gcg tgc tgt gca tgg ttc ccg gtc ctc gat gat atc cag cag        198
Asn Ala Ala Cys Cys Ala Trp Phe Pro Val Leu Asp Asp Ile Gln Gln
 40                  45                  50                  55 aac ctc ttc cac ggt ggc cag tgc ggt gcc gag gcc cac gag gcc ctt        246
Asn Leu Phe His Gly Gly Gln Cys Gly Ala Glu Ala His Glu Ala Leu
                     60                  65                  70 cgt atg gtc ttc cac gac tcc atc gct atc tcg ccc aag ctt cag tcg        294
Arg Met Val Phe His Asp Ser Ile Ala Ile Ser Pro Lys Leu Gln Ser
             75                  80                  85 cag ggc aag ttt ggc ggc ggc gcg gac ggc tcg atc att acc ttc            342
Gln Gly Lys Phe Gly Gly Gly Ala Asp Gly Ser Ile Ile Thr Phe
         90                  95                 100 tcg tcg atc gag acc acg tac cac ccg aac atc ggc ctc gac gag gtc        390
Ser Ser Ile Glu Thr Thr Tyr His Pro Asn Ile Gly Leu Asp Glu Val
105                 110                 115 gtc gcc atc cag aag ccg ttc atc gcg aag cac ggc gtc acc cgt ggc        438
Val Ala Ile Gln Lys Pro Phe Ile Ala Lys His Gly Val Thr Arg Gly
120                 125                 130                 135 gac ttc atc gca ttc gct ggt gcc gtc ggc gtg agc aac tgc ccg ggc        486
Asp Phe Ile Ala Phe Ala Gly Ala Val Gly Val Ser Asn Cys Pro Gly
                140                 145                 150 gcg ccg cag atg cag ttc ttc ctt ggc cgc ccc gag gca acg cag gcc        534
Ala Pro Gln Met Gln Phe Phe Leu Gly Arg Pro Glu Ala Thr Gln Ala
            155                 160                 165 gcc ccc gac ggt ctc gtg ccc gag ccc ttc cac acc atc gat cag gtt        582
Ala Pro Asp Gly Leu Val Pro Glu Pro Phe His Thr Ile Asp Gln Val
        170                 175                 180 ctc gct cgc atg ctt gac gct ggt ggc ttc gac gag atc gag act gtc        630
Leu Ala Arg Met Leu Asp Ala Gly Gly Phe Asp Glu Ile Glu Thr Val
    185                 190                 195 tgg ctg ctc tct gcc cac tcc atc gcg gct gcg aac gac gtc gac ccg        678
Trp Leu Leu Ser Ala His Ser Ile Ala Ala Ala Asn Asp Val Asp Pro
200                 205                 210                 215 acc atc tcc ggc ctg ccg ttc gac tcc act ccc ggc cag ttc gac tcc        726
Thr Ile Ser Gly Leu Pro Phe Asp Ser Thr Pro Gly Gln Phe Asp Ser
                220                 225                 230 cag ttc ttc gtc gag acg cag ctc cgc ggt acc gca ttc cct ggc aag        774
Gln Phe Phe Val Glu Thr Gln Leu Arg Gly Thr Ala Phe Pro Gly Lys
            235                 240                 245 act ggt atc cag ggc acc gtc atg tcc ccg ctc aag ggc gag atg cgt        822
Thr Gly Ile Gln Gly Thr Val Met Ser Pro Leu Lys Gly Glu Met Arg
        250                 255                 260 ctg cag acg gac cac ttg ttc gcg cgt gac tcg cgc acg gca tgc gag        870
Leu Gln Thr Asp His Leu Phe Ala Arg Asp Ser Arg Thr Ala Cys Glu
    265                 270                 275 tgg cag tcc ttc gtc aac aac cag acg aag ctg cag gag gac ttc cag        918
Trp Gln Ser Phe Val Asn Asn Gln Thr Lys Leu Gln Glu Asp Phe Gln
280                 285                 290                 295 ttc atc ttc acg gcg ctc tcg acg ctc ggc cac gac atg aac gcc atg        966
Phe Ile Phe Thr Ala Leu Ser Thr Leu Gly His Asp Met Asn Ala Met
                300                 305                 310 atc gac tgc tcc gag gtc atc ccc gcg ccc aag ccc gtc aac ttc ggc       1014
Ile Asp Cys Ser Glu Val Ile Pro Ala Pro Lys Pro Val Asn Phe Gly
            315                 320                 325 ccg tcg ttc ttc ccc gcc ggt aag acg cac gcc gac atc gag cag gcc       1062
```

```
                Pro Ser Phe Phe Pro Ala Gly Lys Thr His Ala Asp Ile Glu Gln Ala
                        330                 335                 340 tgc gca tcc acg ccg ttc ccg acg ctc atc acc gcc ccc ggt ccc tct      1110
Cys Ala Ser Thr Pro Phe Pro Thr Leu Ile Thr Ala Pro Gly Pro Ser
        345                 350                 355 gcg tcc gtc gct cgc atc ccc ccg ccg tcc ccc aac taa                  1152
Ala Ser Val Ala Arg Ile Pro Pro Pro Ser Pro Asn
360                 365                 370 gctatgtcta tgctggacat gctctcggtt ctacctcgtc ggtatcgtcg cacggttatc    1212
tcgcgtttgc atcatgtata cctgctcgtg aatatacaa agtggtctat c              1263

<210> SEQ ID NO 12
<211> LENGTH: 372
<212> TYPE: PRT
<213> ORGANISM: Phanerochaete chrysosporium

<400> SEQUENCE: 12

Met Ala Phe Lys Gln Leu Leu Ala Ala Leu Ser Val Ala Leu Thr Leu
1               5                   10                  15

Gln Val Thr Gln Ala Ala Pro Asn Leu Asp Lys Arg Val Ala Cys Pro
            20                  25                  30

Asp Gly Val His Thr Ala Ser Asn Ala Ala Cys Cys Ala Trp Phe Pro
        35                  40                  45

Val Leu Asp Asp Ile Gln Gln Asn Leu Phe His Gly Gly Gln Cys Gly
    50                  55                  60

Ala Glu Ala His Glu Ala Leu Arg Met Val Phe His Asp Ser Ile Ala
65                  70                  75                  80

Ile Ser Pro Lys Leu Gln Ser Gln Gly Lys Phe Gly Gly Gly Gly Ala
                85                  90                  95

Asp Gly Ser Ile Ile Thr Phe Ser Ser Ile Glu Thr Thr Tyr His Pro
            100                 105                 110

Asn Ile Gly Leu Asp Glu Val Val Ala Ile Gln Lys Pro Phe Ile Ala
        115                 120                 125

Lys His Gly Val Thr Arg Gly Asp Phe Ile Ala Phe Ala Gly Ala Val
    130                 135                 140

Gly Val Ser Asn Cys Pro Gly Ala Pro Gln Met Gln Phe Phe Leu Gly
145                 150                 155                 160

Arg Pro Glu Ala Thr Gln Ala Pro Asp Gly Leu Val Pro Glu Pro
                165                 170                 175

Phe His Thr Ile Asp Gln Val Leu Ala Arg Met Leu Asp Ala Gly Gly
            180                 185                 190

Phe Asp Glu Ile Glu Thr Val Trp Leu Leu Ser Ala His Ser Ile Ala
        195                 200                 205

Ala Ala Asn Asp Val Asp Pro Thr Ile Ser Gly Leu Pro Phe Asp Ser
    210                 215                 220

Thr Pro Gly Gln Phe Asp Ser Gln Phe Phe Val Glu Thr Gln Leu Arg
225                 230                 235                 240

Gly Thr Ala Phe Pro Gly Lys Thr Gly Ile Gln Gly Thr Val Met Ser
                245                 250                 255

Pro Leu Lys Gly Glu Met Arg Leu Gln Thr Asp His Leu Phe Ala Arg
            260                 265                 270

Asp Ser Arg Thr Ala Cys Glu Trp Gln Ser Phe Val Asn Asn Gln Thr
        275                 280                 285

Lys Leu Gln Glu Asp Phe Gln Phe Ile Phe Thr Ala Leu Ser Thr Leu
    290                 295                 300
```

```
Gly His Asp Met Asn Ala Met Ile Asp Cys Ser Glu Val Ile Pro Ala
305                 310                 315                 320

Pro Lys Pro Val Asn Phe Gly Pro Ser Phe Pro Ala Gly Lys Thr
            325                 330                 335

His Ala Asp Ile Glu Gln Ala Cys Ala Ser Thr Pro Phe Pro Thr Leu
            340                 345                 350

Ile Thr Ala Pro Gly Pro Ser Ala Ser Val Ala Arg Ile Pro Pro Pro
            355                 360                 365

Pro Ser Pro Asn
    370

<210> SEQ ID NO 13
<211> LENGTH: 1285
<212> TYPE: DNA
<213> ORGANISM: Phanerochaete chrysosporium
<220> FEATURE:
<221> NAME/KEY: CDS
<222> LOCATION: (34)..(1149)
<223> OTHER INFORMATION: CKG5 ligninase precursor

<400> SEQUENCE: 13
gtcagactct ccaacggttg cctttggaca gac atg gcc ttc aag aag ctc ctt        54
                                    Met Ala Phe Lys Lys Leu Leu
                                      1               5 gct gtt ctt acc gcc gct ctc tcc ctc cgc gct gcg cag ggt gcg gcc       102
Ala Val Leu Thr Ala Ala Leu Ser Leu Arg Ala Ala Gln Gly Ala Ala
         10                  15                  20 gtc gag aag cgc gcg acc tgc tcg aac ggc aag gtc gtc ccc gcg gcg       150
Val Glu Lys Arg Ala Thr Cys Ser Asn Gly Lys Val Val Pro Ala Ala
 25                  30                  35 tct tgc tgc acc tgg ttc aac gtt ctg tcc gat atc cag gag aac ctc       198
Ser Cys Cys Thr Trp Phe Asn Val Leu Ser Asp Ile Gln Glu Asn Leu
40                  45                  50                  55 ttc aat ggc ggc cag tgt ggc gcc gag gct cat gag tcg atc cgt ctc       246
Phe Asn Gly Gly Gln Cys Gly Ala Glu Ala His Glu Ser Ile Arg Leu
                 60                  65                  70 gtc ttc cac gac gcc atc gct atc tct ccc gct atg gag ccg cag gcc       294
Val Phe His Asp Ala Ile Ala Ile Ser Pro Ala Met Glu Pro Gln Ala
             75                  80                  85 agt tcg gtg cga ggc gcc gat ggt tct atc atg atc ttc gac gag atc       342
Ser Ser Val Arg Gly Ala Asp Gly Ser Ile Met Ile Phe Asp Glu Ile
         90                  95                 100 gag acc aac ttc cat ccc aac atc ggt ctc gac gag atc gtc cgc ctg       390
Glu Thr Asn Phe His Pro Asn Ile Gly Leu Asp Glu Ile Val Arg Leu
    105                 110                 115 cag aag ccg ttc gtc cag aag cac ggt gtc act ccc ggt gac ttc atc       438
Gln Lys Pro Phe Val Gln Lys His Gly Val Thr Pro Gly Asp Phe Ile
120                 125                 130                 135 gcc ttc gct ggc gcg gtg gcg ctc agt aac tgc ccc ggt gct ccg cag       486
Ala Phe Ala Gly Ala Val Ala Leu Ser Asn Cys Pro Gly Ala Pro Gln
                140                 145                 150 atg aac ttc ttc act ggt cgt gct ccg gca act cag cca gcc cct gac       534
Met Asn Phe Phe Thr Gly Arg Ala Pro Ala Thr Gln Pro Ala Pro Asp
            155                 160                 165 ggc ctc gtc cca gag ccc ttc cac tct gtt gac caa atc atc gac cgt       582
Gly Leu Val Pro Glu Pro Phe His Ser Val Asp Gln Ile Ile Asp Arg
        170                 175                 180 gtc ttc gat gcc ggt gaa ttc gat gag ctc gag ctc gtc tgg atg ctc       630
Val Phe Asp Ala Gly Glu Phe Asp Glu Leu Glu Leu Val Trp Met Leu
    185                 190                 195 tct gca cac tcc gtc gcg gct gcc aac gat atc gac ccg aac atc cag       678
```

```
Ser Ala His Ser Val Ala Ala Asn Asp Ile Asp Pro Asn Ile Gln
200                 205                 210                 215 ggc ttg ccc ttc gac tcg acc ccc ggt att ttc gat tcc cag ttc ttc        726
Gly Leu Pro Phe Asp Ser Thr Pro Gly Ile Phe Asp Ser Gln Phe Phe
                220                 225                 230 gtc gag act cag ctt gct ggc acc ggc ttc act ggc ggt tct aac aac        774
Val Glu Thr Gln Leu Ala Gly Thr Gly Phe Thr Gly Gly Ser Asn Asn
            235                 240                 245 cag ggc gag gtt tcc tcc ccg ctt cca ggc gag atg cgt ctc cag tct        822
Gln Gly Glu Val Ser Ser Pro Leu Pro Gly Glu Met Arg Leu Gln Ser
        250                 255                 260 gac ttc ctg atc gct cgt gac gcg cgc acc gcc tgc gag tgg cag tcg        870
Asp Phe Leu Ile Ala Arg Asp Ala Arg Thr Ala Cys Glu Trp Gln Ser
265                 270                 275 ttc gtc aac aac cag tcc aag ctc gtc tcc gac ttc caa ttc atc ttc        918
Phe Val Asn Asn Gln Ser Lys Leu Val Ser Asp Phe Gln Phe Ile Phe
280                 285                 290                 295 ctc gcc ctc act cag ctc ggc cag gac ccg gat gcg atg acc gac tgc        966
Leu Ala Leu Thr Gln Leu Gly Gln Asp Pro Asp Ala Met Thr Asp Cys
                300                 305                 310 tct gct gtc atc ccc atc tcc aag ccc gcc ccg aac aac acc ccc gga       1014
Ser Ala Val Ile Pro Ile Ser Lys Pro Ala Pro Asn Asn Thr Pro Gly
            315                 320                 325 ttc tcc ttc ttc ccg ccc ggc atg acg atg gac gat gtc gag cag gct       1062
Phe Ser Phe Phe Pro Pro Gly Met Thr Met Asp Asp Val Glu Gln Ala
        330                 335                 340 tgc gcc gag acg ccc ttc ccg act ctc tcg act ctc cct ggc ccc gcg       1110
Cys Ala Glu Thr Pro Phe Pro Thr Leu Ser Thr Leu Pro Gly Pro Ala
345                 350                 355 acc tcc gtc gct cgc atc cct cct cct cct ggt gct taa gcagccatca        1159
Thr Ser Val Ala Arg Ile Pro Pro Pro Pro Gly Ala
360                 365                 370 gacttcggat cacaccccgg tattggcaac ggaaatttag aacgaagatc gtccagtgtt     1219
ttgaagtaga aatgtgcttg tactgtgtaa acagctcttt tgacgaaata cactctgatt     1279
tcgtcg                                                                1285

<210> SEQ ID NO 14
<211> LENGTH: 371
<212> TYPE: PRT
<213> ORGANISM: Phanerochaete chrysosporium

<400> SEQUENCE: 14

Met Ala Phe Lys Lys Leu Leu Ala Val Leu Thr Ala Ala Leu Ser Leu
1               5                   10                  15

Arg Ala Ala Gln Gly Ala Ala Val Glu Lys Arg Ala Thr Cys Ser Asn
            20                  25                  30

Gly Lys Val Val Pro Ala Ala Ser Cys Cys Thr Trp Phe Asn Val Leu
        35                  40                  45

Ser Asp Ile Gln Glu Asn Leu Phe Asn Gly Gly Gln Cys Gly Ala Glu
    50                  55                  60

Ala His Glu Ser Ile Arg Leu Val Phe His Asp Ala Ile Ala Ile Ser
65                  70                  75                  80

Pro Ala Met Glu Pro Gln Ala Ser Ser Val Arg Gly Ala Asp Gly Ser
                85                  90                  95

Ile Met Ile Phe Asp Glu Ile Glu Thr Asn Phe His Pro Asn Ile Gly
            100                 105                 110

Leu Asp Glu Ile Val Arg Leu Gln Lys Pro Phe Val Gln Lys His Gly
        115                 120                 125
```

Val Thr Pro Gly Asp Phe Ile Ala Phe Ala Gly Ala Val Ala Leu Ser
    130                 135                 140

Asn Cys Pro Gly Ala Pro Gln Met Asn Phe Phe Thr Gly Arg Ala Pro
145                 150                 155                 160

Ala Thr Gln Pro Ala Pro Asp Gly Leu Val Pro Glu Pro Phe His Ser
                165                 170                 175

Val Asp Gln Ile Ile Asp Arg Val Phe Asp Ala Gly Glu Phe Asp Glu
            180                 185                 190

Leu Glu Leu Val Trp Met Leu Ser Ala His Ser Val Ala Ala Ala Asn
        195                 200                 205

Asp Ile Asp Pro Asn Ile Gln Gly Leu Pro Phe Asp Ser Thr Pro Gly
    210                 215                 220

Ile Phe Asp Ser Gln Phe Phe Val Glu Thr Gln Leu Ala Gly Thr Gly
225                 230                 235                 240

Phe Thr Gly Gly Ser Asn Asn Gln Gly Glu Val Ser Ser Pro Leu Pro
                245                 250                 255

Gly Glu Met Arg Leu Gln Ser Asp Phe Leu Ile Ala Arg Asp Ala Arg
            260                 265                 270

Thr Ala Cys Glu Trp Gln Ser Phe Val Asn Asn Gln Ser Lys Leu Val
        275                 280                 285

Ser Asp Phe Gln Phe Ile Phe Leu Ala Leu Thr Gln Leu Gly Gln Asp
    290                 295                 300

Pro Asp Ala Met Thr Asp Cys Ser Ala Val Ile Pro Ile Ser Lys Pro
305                 310                 315                 320

Ala Pro Asn Asn Thr Pro Gly Phe Ser Phe Phe Pro Gly Met Thr
                325                 330                 335

Met Asp Asp Val Glu Gln Ala Cys Ala Glu Thr Pro Phe Pro Thr Leu
            340                 345                 350

Ser Thr Leu Pro Gly Pro Ala Thr Ser Val Ala Arg Ile Pro Pro Pro
        355                 360                 365

Pro Gly Ala
    370

<210> SEQ ID NO 15
<211> LENGTH: 360
<212> TYPE: DNA
<213> ORGANISM: Solanum tuberosum

<400> SEQUENCE: 15
tgaccctaga cttgtccatc ttctggattg gccaagttaa ttaatgtatg aaataaaagg     60
atgcacacat agtgacatgc taatcactat aatgtgggca tcaaagttgt gtgttatgtg    120
taataactaa ttatctgaat aagagaaaga gagatcatcc atatttctta tcctaaatga    180
atgacagtgt ctttataatt ctttgatgaa cagatgcatt ttattaacca attccatata    240
catataaata ttaatcatat ataattaata tcaattggtt agcaaaaccc aaatctagtc    300
taggtgtgtt ttgctaatta tgggggatag agcaaaaaag aaactaacgt ctcaagaatc    360

<210> SEQ ID NO 16
<211> LENGTH: 2521
<212> TYPE: DNA
<213> ORGANISM: Agrobacterium tumefaciens
<220> FEATURE:
<221> NAME/KEY: CDS
<222> LOCATION: (585)..(1826)
<223> OTHER INFORMATION: nopaline synthetase

<400> SEQUENCE: 16

-continued

```
tagccgaccc agacgagcca agggatcttt ttggaatgct gctccgtcgt caggctttcc      60
gacgtttggg tggttgaaca gaagtcatta tcgtacggaa tgccaagcac tcccgagggg     120
aaccctgtgg ttggcatgca catacaaatg gacgaacgga taaacctttt cacgcccttt     180
taaatatccg ttattctaat aaacgctctt ttctcttagg tttacccgcc aatatatcct     240
gtcaaacact gatagtttaa actgaaggcg ggaaacgaca atctgatcat gagcggagaa     300
ttaagggagt cacgttatga cccccgccga tgacgcggga caagccgttt acgtttgga      360 actgacagaa ccgcaacgat tgaaggagcc actcagccgc gggtttctgg agtttaatga     420
gctaagcaca tacgtcagaa accattattg cgcgttcaaa agtcgcctaa ggtcactatc     480
agctagcaaa tatttcttgt caaaaatgct ccactgacgt tccataaatt cccctcggta     540
tccaattaga gtctcatatt cactctcaat ccaaataatc tgca atg gca att acc      596
                                                 Met Ala Ile Thr
                                                   1 tta tcc gca act tct tta cct att tcc gcc gca gat cac cat ccg ctt      644
Leu Ser Ala Thr Ser Leu Pro Ile Ser Ala Ala Asp His His Pro Leu
  5                  10                  15                  20 ccc ttg acc gta ggt gtc ctc ggt tct ggt cac gcg ggg act gca tta      692
Pro Leu Thr Val Gly Val Leu Gly Ser Gly His Ala Gly Thr Ala Leu
                 25                  30                  35 gcg gct tgg ttc gcc tcc cgg cat gtt ccc acg gcg ctg tgg gca cca      740
Ala Ala Trp Phe Ala Ser Arg His Val Pro Thr Ala Leu Trp Ala Pro
             40                  45                  50 gca gat cat cca gga tcg atc tca gca atc aag gcc aat gaa gga gtt      788
Ala Asp His Pro Gly Ser Ile Ser Ala Ile Lys Ala Asn Glu Gly Val
         55                  60                  65 atc acc acc gag gga atg att aac ggt cca ttt agg gtc tca gcc tgt      836
Ile Thr Thr Glu Gly Met Ile Asn Gly Pro Phe Arg Val Ser Ala Cys
 70                  75                  80 gat gac ctt gcc gca gtt att cgc tcc agc cgt gta ctg att att gta      884
Asp Asp Leu Ala Ala Val Ile Arg Ser Ser Arg Val Leu Ile Ile Val
 85                  90                  95                 100 acc cgt gcg gac gtt cac gac agc ttc gtc aac gaa ctc gcc aac ttc      932
Thr Arg Ala Asp Val His Asp Ser Phe Val Asn Glu Leu Ala Asn Phe
                105                 110                 115 aac ggc gaa ctc gca aca aag gat att gtc gtc gtg tgc ggc cat ggc      980
Asn Gly Glu Leu Ala Thr Lys Asp Ile Val Val Val Cys Gly His Gly
            120                 125                 130 ttc tcc atc aag tac gag aga cag ctg cga ttc aag cga ata ttc gag     1028
Phe Ser Ile Lys Tyr Glu Arg Gln Leu Arg Phe Lys Arg Ile Phe Glu
        135                 140                 145 acg gat aat tcg ccc ata acg tct aag cta tcg gat caa aaa aaa tgt     1076
Thr Asp Asn Ser Pro Ile Thr Ser Lys Leu Ser Asp Gln Lys Lys Cys
    150                 155                 160 aac gtc aac atc aag gaa atg aaa gcg tct ttc gga ctg tca tgt ttc     1124
Asn Val Asn Ile Lys Glu Met Lys Ala Ser Phe Gly Leu Ser Cys Phe
165                 170                 175                 180 cca att cat cgc gat gat gct ggc gtg att gat cta ccc gaa gat acc     1172
Pro Ile His Arg Asp Asp Ala Gly Val Ile Asp Leu Pro Glu Asp Thr
                185                 190                 195 aag aac atc ttt gcc cag cta ttt tcc gct aga atc atc tgc atc ccg     1220
Lys Asn Ile Phe Ala Gln Leu Phe Ser Ala Arg Ile Ile Cys Ile Pro
            200                 205                 210 ccg ttg caa gtg cta ttc ttt tcc aac tgt atc act cat gcg gtt ccg     1268
Pro Leu Gln Val Leu Phe Phe Ser Asn Cys Ile Thr His Ala Val Pro
        215                 220                 225 gca gtc atg aac atc gga aga ctc cgc gac cca gcc aat tct ctt act     1316
```

```
                              -continued
Ala Val Met Asn Ile Gly Arg Leu Arg Asp Pro Ala Asn Ser Leu Thr
    230                 235                 240 aaa aga gct gag aag tgg ctt ctt gaa cta gac gag cga acc cca cga    1364
Lys Arg Ala Glu Lys Trp Leu Leu Glu Leu Asp Glu Arg Thr Pro Arg
245                 250                 255                 260 gcc gag aag ggc ttt ttc ttt tat ggt gaa gga tcc aac act tac gtt    1412
Ala Glu Lys Gly Phe Phe Phe Tyr Gly Glu Gly Ser Asn Thr Tyr Val
                265                 270                 275 tgc aac gtc caa gag caa ata gac cac gaa cgc gg aag gtt gcc gca    1460
Cys Asn Val Gln Glu Gln Ile Asp His Glu Arg Arg Lys Val Ala Ala
                280                 285                 290 gcg tgt gga ttg cgt ctc aat tct ctc ttg cag gaa tgc aat gat gaa    1508
Ala Cys Gly Leu Arg Leu Asn Ser Leu Leu Gln Glu Cys Asn Asp Glu
                295                 300                 305 tat gat act gac tat gaa act ttg agg gaa tac tgc cta gca ccg tca    1556
Tyr Asp Thr Asp Tyr Glu Thr Leu Arg Glu Tyr Cys Leu Ala Pro Ser
310                 315                 320 cct cat aac gtg cat cat gca tgc cct gac aac atg gaa cat cgc tat    1604
Pro His Asn Val His His Ala Cys Pro Asp Asn Met Glu His Arg Tyr
325                 330                 335                 340 ttt tct gaa gaa tta tgc tcg ttg gag gat gtc gcg gca att gca gct    1652
Phe Ser Glu Glu Leu Cys Ser Leu Glu Asp Val Ala Ala Ile Ala Ala
                345                 350                 355 att gcc aac atc gaa cta ccc ctc acg cat gca ttc atc aat att att    1700
Ile Ala Asn Ile Glu Leu Pro Leu Thr His Ala Phe Ile Asn Ile Ile
                360                 365                 370 cat gcg ggg aaa ggc aag att aat cca act ggc aaa tca tcc agc gtg    1748
His Ala Gly Lys Gly Lys Ile Asn Pro Thr Gly Lys Ser Ser Ser Val
                375                 380                 385 att ggt aac ttc agt tcc agc gac ttg att cgt ttt ggt gct acc cac    1796
Ile Gly Asn Phe Ser Ser Ser Asp Leu Ile Arg Phe Gly Ala Thr His
390                 395                 400 gtt ttc aat aag gac gag atg gtg gag taa agaaggagtg cgtcgaagca      1846
Val Phe Asn Lys Asp Glu Met Val Glu
405                 410 gatcgttcaa acatttggca ataaagtttc ttaagattga atcctgttgc cggtcttgcg  1906
atgattatca tataatttct gttgaattac gttaagcatg taataattaa catgtaatgc  1966
atgacgttat ttatgagatg ggttttatg attagagtcc cgcaattata catttaatac   2026
gcgatagaaa acaaaatata gcgcgcaaac taggataaat tatcgcgcgc ggtgtcatct  2086
atgttactag atcgatcaaa cttcggtact gtgtaatgac gatgagcaat cgagaggctg  2146
actaacaaaa ggtatgccca aaaacaacct ctccaaactg tttcgaattg aagtttctg   2206 ctcatgccga caggcataac ttagatattc gcgggctatt cccactaatt cgtcctgctg  2266
gtttgcgcca agataaatca gtgcatctcc ttacaagttc ctctgtcttg tgaaatgaac  2326
tgctgactgc cccccaagaa agcctcctca tctcccagtt ggcggcggct gatacaccat  2386
cgaaaaccca cgtccgaaca cttgatacat gtgcctgaga aataggccta cgtccaagag  2446
caagtccttt ctgtgctcgt cggaaattcc tctcctgtca acggtcgtg cgcatgtctt    2506 gcgttgatga agctt                                                   2521

<210> SEQ ID NO 17
<211> LENGTH: 413
<212> TYPE: PRT
<213> ORGANISM: Agrobacterium tumefaciens

<400> SEQUENCE: 17

Met Ala Ile Thr Leu Ser Ala Thr Ser Leu Pro Ile Ser Ala Ala Asp
```

```
          1               5              10              15
His His Pro Leu Pro Leu Thr Val Gly Val Leu Gly Ser Gly His Ala
             20                  25                  30

Gly Thr Ala Leu Ala Ala Trp Phe Ala Ser Arg His Val Pro Thr Ala
             35                  40                  45

Leu Trp Ala Pro Ala Asp His Pro Gly Ser Ile Ser Ala Ile Lys Ala
 50                  55                  60

Asn Glu Gly Val Ile Thr Thr Glu Gly Met Ile Asn Gly Pro Phe Arg
 65                  70                  75                  80

Val Ser Ala Cys Asp Asp Leu Ala Ala Val Ile Arg Ser Ser Arg Val
                 85                  90                  95

Leu Ile Ile Val Thr Arg Ala Asp Val His Asp Ser Phe Val Asn Glu
            100                 105                 110

Leu Ala Asn Phe Asn Gly Glu Leu Ala Thr Lys Asp Ile Val Val Val
            115                 120                 125

Cys Gly His Gly Phe Ser Ile Lys Tyr Glu Arg Gln Leu Arg Phe Lys
        130                 135                 140

Arg Ile Phe Glu Thr Asp Asn Ser Pro Ile Thr Ser Lys Leu Ser Asp
145                 150                 155                 160

Gln Lys Lys Cys Asn Val Asn Ile Lys Glu Met Lys Ala Ser Phe Gly
                165                 170                 175

Leu Ser Cys Phe Pro Ile His Arg Asp Asp Ala Gly Val Ile Asp Leu
            180                 185                 190

Pro Glu Asp Thr Lys Asn Ile Phe Ala Gln Leu Phe Ser Ala Arg Ile
            195                 200                 205

Ile Cys Ile Pro Pro Leu Gln Val Leu Phe Phe Ser Asn Cys Ile Thr
        210                 215                 220

His Ala Val Pro Ala Val Met Asn Ile Gly Arg Leu Arg Asp Pro Ala
225                 230                 235                 240

Asn Ser Leu Thr Lys Arg Ala Glu Lys Trp Leu Leu Glu Leu Asp Glu
                245                 250                 255

Arg Thr Pro Arg Ala Glu Lys Gly Phe Phe Phe Tyr Gly Glu Gly Ser
            260                 265                 270

Asn Thr Tyr Val Cys Asn Val Gln Glu Gln Ile Asp His Glu Arg Arg
            275                 280                 285

Lys Val Ala Ala Ala Cys Gly Leu Arg Leu Asn Ser Leu Leu Gln Glu
        290                 295                 300

Cys Asn Asp Glu Tyr Asp Thr Asp Tyr Glu Thr Leu Arg Glu Tyr Cys
305                 310                 315                 320

Leu Ala Pro Ser Pro His Asn Val His His Ala Cys Pro Asp Asn Met
                325                 330                 335

Glu His Arg Tyr Phe Ser Glu Glu Leu Cys Ser Leu Glu Asp Val Ala
            340                 345                 350

Ala Ile Ala Ala Ile Ala Asn Ile Glu Leu Pro Leu Thr His Ala Phe
        355                 360                 365

Ile Asn Ile Ile His Ala Gly Lys Gly Lys Ile Asn Pro Thr Gly Lys
370                 375                 380

Ser Ser Ser Val Ile Gly Asn Phe Ser Ser Asp Leu Ile Arg Phe
385                 390                 395                 400

Gly Ala Thr His Val Phe Asn Lys Asp Glu Met Val Glu
                405                 410

<210> SEQ ID NO 18
<211> LENGTH: 835
```

<212> TYPE: DNA
<213> ORGANISM: Streptomyces hygroscopicus

<400> SEQUENCE: 18

```
gctcgctgtc attttcgaga cgccatcttt ggaagcggtg gccgaatccg tactgcgcgg    60
actcgacgac gcgtaaaacg atcgaccacg tacacgagtc cggacacggg gcgaggaggc   120
ccggttccgg caccgaggaa gaccgaagga agaccacacg tgagcccaga acgacgcccg   180
gccgacatcc gccgtgccac cgaggcggac atgccggcgg tctgcaccat cgtcaaccac   240
tacatcgaga caagcacggt caacttccgt accgagccgc aggaaccgca ggagtggacg   300
gacgacctcg tccgtctgcg ggagcgctat ccctggctcg tcgccgaggt ggacggcgag   360
gtcgccggca tcgcctacgc gggccccgtgg aaggcacgca acgcctacga ctggacggcc   420
gagtcgaccg tgtacgtctc cccccgccac cagcggacgg gactgggctc cacgctctac   480
acccacctgc tgaagtccct ggaggcacag ggcttcaaga gcgtggtcgc tgtcatcggg   540
ctgcccaacg acccgagcgt gcgcatgcac gaggcgctcg gatatgcccc ccgcggcatg   600
ctgcgggcgg ccggcttcaa gcacgggaac tggcatgacg tgggtttctg gcagctggac   660
ttcagcctgc cggtaccgcc ccgtccggtc ctgcccgtca ccgagatctg aacgagtgc    720
gcgtgggcat cgcccgagtt ggagctggta cgggaactca tcgaactcaa ctggcatacc   780
cgcaatggtg aggtggaacc gcggcggatc gcgtacgacc gtgcccagga ggcct         835
```

<210> SEQ ID NO 19
<211> LENGTH: 623
<212> TYPE: DNA
<213> ORGANISM: Oryza sativa

<400> SEQUENCE: 19

```
tatatacata ccccccccctc tcctcccatc ccccaaccc taccaccacc accaccacca    60
cctcctcccc cctcgctgcc ggacgacgag ctcctccccc ctcccctcc gccgccgccg   120
gtaaccaccc cgcgtccctc tcctctttct ttctccgttt ttttttttccg tctcgtctcg   180
atctttggcc ttggtagttt gggggcgaga ggcggcttcg tcgcccagat cggtgcgcgg   240
gaggggcggg atctcgcggc tgggtctcgg cgtgcggccg gatcctcgcg gggaatgggg   300
ctctcggatg tagatctgat ccgccgttgt tgggggagat gatggggcgt ttaaaatttc   360
gccatgctaa acaagatcag gaagagggga aaagggcact atggtttata tttttatata   420
tttctgctgc tgctcgtcag gcttagatgt gctagatctt tctttcttct ttttgtgggt   480
agaatttgaa tccctcagca ttgttcatcg gtagtttttc ttttcatgat ttgtgacaaa   540
tgcagcctcg tgcggagctt ttttgtaggt agaagatggc tgacgccgag gatggggat    600
ccccgggtgg tcagtcccttt atg                                          623
```

<210> SEQ ID NO 20
<211> LENGTH: 1506
<212> TYPE: DNA
<213> ORGANISM: Trichoderma longibrachiatum

<400> SEQUENCE: 20

```
accatggctc aatctgcttg tactcttcaa tctgagactc atcctccact tacttggcag    60
aagtgttcat ctggtggtac ttgtactcaa cagactggat ctgttgttat tgatgctaac   120
tggagatgga ctcatgctac taactcttct actaactgct atgatggtaa cacttggtca   180
tctactcttt gtcctgataa cgagacttgt gctaagaact gctgtcttga tggtgctgct   240
tacgcttcta cttacggagt tactacttct ggaaactctc tttctattgg attcgttact   300
```

-continued

```
cagtctgctc agaagaacgt tggtgctagg ttgtacttga tggcttctga tactacttac      360
caagagttca ctcttcttgg taacgagttc tctttcgatg ttgatgtttc tcaacttcca      420
tgtggtttga acggagcttt gtacttcgtt tctatggatg ctgatggtgg agtttctaag      480
tatccaacta acactgctgg agctaagtat ggtactggtt actgtgattc tcagtgtcca     540
agagatctta agttcattaa cggacaagct aatgttgagg gatgggagcc atcttctaac     600
aatgctaaca ctggtattgg aggtcatgga tcttgttgct ctgagatgga tatttgggag     660
gctaactcta tctctgaggc tcttactcca catccatgca ctactgttgg acaagagatt     720
tgcgagggag atggttgtgg tggaacttac tctgataaca gatacggagg tacttgcgat     780
ccagatggat gtgattggaa tccatacaga cttggtaaca cttctttcta cggtccagga    840
tcttcattca ctcttgatac tactaagaag ttgactgttg ttactcagtt cgagacttct    900
ggtgctatca acagatacta cgttcagaat ggagttactt ccaacaacc taacgctgag     960 cttggttctt actctggtaa cgagttgaac gatgattact gtactgctga ggaagctgag    1020
tttggtggat catctttctc tgataagggt ggacttactc agttcaagaa ggctacttct    1080
ggtggtatgg ttcttgttat gtctctttgg gatgattact acgctaacat gttgtggctt    1140
gattctactt acccaactaa cgagacttct tctactccag gtgctgttag aggatcttgc    1200
tctacttctt ctggtgttcc tgctcaagtt gaatctcaat ctcctaatgc taaggttact    1260
ttctctaaca tcaagttcgg accaattgga tctactggta acccttctgg aggtaatcca    1320
cctggaggta atccacctgg aactactaca actaggagac cagctactac aactggatca    1380
tctccaggac ctactcaatc tcattacggt caatgtggag gtattggtta ctctggtcca    1440
actgtttgtg cttctggaac tacttgtcaa gttcttaacc cttactattc tcaatgcctt    1500
taatga                                                              1506

<210> SEQ ID NO 21
<211> LENGTH: 26
<212> TYPE: DNA
<213> ORGANISM: Artificial Sequence
<220> FEATURE:
<223> OTHER INFORMATION: PCR primer SP1F

<400> SEQUENCE: 21
ccgcctaggc gcatggcccc ctccgt                                            26

<210> SEQ ID NO 22
<211> LENGTH: 25
<212> TYPE: DNA
<213> ORGANISM: Artificial Sequence
<220> FEATURE:
<223> OTHER INFORMATION: PCR primer SP3R

<400> SEQUENCE: 22
cgctgtacac gcacctgatc ctgcc                                             25
```

TRANSGENIC COVER PLANTS CONTAINING HEMICELLULASE AND CELLULASE WHICH DEGRADE LIGNIN AND CELLULOSE TO FERMENTABLE SUGARS

CROSS-REFERENCE TO RELATED APPLICATIONS

This application is a continuation of U.S. patent application Ser. No. 11/999,197, filed Dec. 4, 2007, now U.S. Pat. No. 8,093,456, issued Jan. 10, 2012, which is a continuation-in-part of U.S. patent application Ser. No. 11/399,675, filed Apr. 6, 2006 now U.S. Pat. No. 7,371,926, which is a continuation of Ser. No. 09/981,900 filed Oct. 18, 2001, now U.S. Pat. No. 7,049,485, issued May 23, 2006, which claims benefit of 60/242,408, filed Oct. 20, 2000, each of which are incorporated herein by reference in their entirety.

STATEMENT REGARDING FEDERALLY SPONSORED RESEARCH OR DEVELOPMENT

None.

REFERENCE TO A NUCLEOTIDE/AMINO ACID SEQUENCE LISTING APPENDIX SUBMITTED ON A COMPACT DISC

The application contains nucleotide and amino acid sequences which are identified with SEQ ID NOs. A compact disc is provided which contains the Sequence Listings for the sequences. The Sequence Listing on the compact disc is identical to the paper copy of the Sequence Listing provided with the application.

BACKGROUND OF THE INVENTION (1) Field of the Invention

The present invention relates to transgenic monocot plants which are cover crops which after harvest degrade cellulose and hemicellulase therein to fermentable sugars which can further be fermented to ethanol or other products. In particular, the transgenic plants comprise cellulase and hemicellulase and optionally ligninase genes from microbes operably linked to a DNA encoding a signal peptide which targets the fusion polypeptide produced therefrom to sub-cellular compartments of the plant, in particular the chloroplasts, apoplast (cell wall areas), endoplasmic reticulum, mitochondria and vacule. When the cover crop transgenic monocot plants are harvested, the plants are ground to release the ligninase, cellulase and hemicellulase which then degrade the lignin, cellulose and hemicellulose of the transgenic plants for production of fermentable sugars. The ligninase will degrade lignin into aromatic (non-sugar) compounds to reduce the needs for expensive pretreatment processes and cellulase will convert polysaccharides into fermentable sugars.

(2) Description of Related Art

If human economies are to become more sustainable, then it is imperative that humans learn how to use the solar energy that is carbon-fixed in plant biomass to meet a larger fraction of energy and raw material needs. About 180 billion tons of new plant matter (biomass) is produced annually worldwide. Thus, about 30 tons of plant matter per person is produced every year. In North America, about three tons of plant matter is used per person every year. That means that the energy value of naturally produced biomass is equivalent to ten times the total human use of all types of energy. However, because of the difficulty in extracting the energy from plant biomass, most of the energy potential of the biomass goes unused.

At present, the United States produces ethanol from starch produced in corn grain using amylase enzymes to degrade the starch to fermentable sugars. Much of the ethanol that is produced from corn grain is exported to Brazil where it is efficiently used to power transportation vehicles. In general, while the corn grain is used in the production of ethanol, the remainder of the corn biomass, i.e., the leaves and stalks, is seldom unused because of the cost in degrading the leaves and stalks comprising lignins and cellulose, generally in the form of lignocellulose, to fermentable sugars. The lignocellulose in the stalks and leaves of corn biomass represents a tremendous source of untapped energy that goes unused because of the difficulty and cost of converting it to fermentable sugars.

Major expenses associated with crop biomass conversion include the costs of pretreatment processes to remove lignin and make the lignocellulosic matter accessible to cellulase, plus the costs of production of hydrolysis enzymes such as cellulases in microbial bioreactors. Production of hydrolysis enzymes within the biomass of cereal cover crops especially will reduce or eliminate the needs for the expensive enzymes produced in microbes. Cereal cover crops are naturally very low in lignin, meaning that they require very little needs for pretreatment processes. The ligninase produced within these plants will degrade the lignin content of these crops before or during processing. In Great Lakes areas, many acres of cereal cover crops are annually planted shortly after the crop (soybean, corn, etc) harvest, and then killed in spring by herbicides before planting of the next crop. In Michigan, cereal rye and winter wheat produce 1.7 to 2 tons of dry biomass, when they are harvested in late May just before planting soybean. These cereal cover crops are planted to reduce soil erosion and nutrient leaching from soil and water sediment, and provide weed suppression. In addition, inclusion of these cover crops before planting soybean breaks soybean cyst nematode and white mold cycle and therefore minimizes yield reductions due to these factors. Considering that 1.8 million acres of soybean are planted only in Michigan, and much more in the U.S. and around the globe, farmers can greatly increase their farm income should they plant these cover crops after harvesting of their corn crop, and then harvesting and selling them as crop biomass before planting of soybean.

Currently, there are four technologies available to convert cellulose to fermentable sugars. These are concentrated acid hydrolysis, dilute acid hydrolysis, biomass gasification and fermentation, and enzymatic hydrolysis.

Concentrated acid hydrolysis is based on concentrated acid de-crystallization of cellulose followed by dilute acid hydrolysis to sugars at near theoretical yields. Separation of acid from sugars, acid recovery, and acid re-concentration are critical unit operations. The concentrated sulfuric acid process has been commercialized in the past, particularly in the former Soviet Union, Germany, and Japan. However, these processes were only successful during times of national crisis, when economic competitiveness of ethanol production could be ignored.

Dilute acid hydrolysis occurs in two stages to maximize sugar yields from the hemicellulose and cellulose fractions of biomass. The first stage is operated under milder conditions to hydrolyze hemicellulose, while the second stage is optimized to hydrolyze the more resistant cellulose fraction. Liquid hydrolyzates are recovered from each stage, neutralized, and fermented to ethanol. As indicated earlier, Germany, Japan, and Russia have operated dilute acid hydrolysis percolation plants off and on over the past 50 years. However, the technology remains non-competitive for the conversion of cellulose to fermentable sugars for production of ethanol.

In biomass gasification and fermentation, biomass is converted to a synthesis gas, which consists primarily of carbon monoxide, carbon dioxide, and hydrogen) via a high temperature gasification process. Anaerobic bacteria are then used to convert the synthesis gas into ethanol.

In early processes embracing enzymatic hydrolysis of biomass to ethanol, the acid hydrolysis step was replaced with an enzyme hydrolysis step. This process scheme was often referred to as separate hydrolysis and fermentation (SHF) ([1]Wilke et al., Biotechnol. Bioengin. 6: 155-175 (1976)). In SHF, pretreatment of the biomass is required to remove disrupt lignocellulosic matter, remove lignin so making the cellulose more accessible to the cellulase enzymes. Many pretreatment options have been considered, including both thermal and chemical steps. The most important process improvement made for the enzymatic hydrolysis of biomass was the introduction of simultaneous saccharification and fermentation (SSF) U.S. Pat. No. 3,990,944 to Gauss et al. and U.S. Pat. No. 3,990,945 to Huff et al.). This process scheme reduced the number of reactors involved by eliminating the separate hydrolysis reactor and, more importantly, avoiding the problem of product inhibition associated with enzymes.

In the presence of glucose, β-glucosidase stops hydrolyzing cellobiose. The build up of cellobiose, in turn, shuts down cellulose degradation. In the SSF process scheme, cellulase enzyme and fermenting microbes are combined. As sugars are produced by the enzymes, the fermentative organisms convert them to ethanol. The SSF process has, more recently, been improved to include the co-fermentation of multiple sugar substrates in a process known as simultaneous saccharification and co-fermentation (SSCF).

While cellulase enzymes are already commercially available for a variety of applications. Most of these applications do not involve extensive hydrolysis of cellulose. For example, the textile industry applications for cellulases require less than 1% hydrolysis. Ethanol production, by contrast, requires nearly complete hydrolysis. In addition, most of the commercial applications for cellulase enzymes represent higher value markets than the fuel market. For these reasons, enzymatic hydrolysis of biomass to ethanol remains non-competitive.

However, while the above processes have focused on converting cellulose to fermentable sugars or other products, much of the cellulose in plant biomass is in the form of lignocellulose. Lignin is a complex macromolecule consisting of aromatic units with several types of inter-unit linkages. In the plant, the lignin physically protects the cellulose polysaccharides in complexes called lignocellulose. To degrade the cellulose in the lignocellulose complexes, the lignin must first be degraded. While lignin can be removed in chemi-mechanical processes that free the cellulose for subsequent conversion to fermentable sugars, the chemi-mechanical processes are inefficient. Ligninase and cellulase enzymes, which are produced by various microorganisms, have been used to convert the lignins and cellulose, respectively, in plant biomass for production of fermentable sugars. However, the cost for these enzymes is expensive. As long as the cost to degrade plant biomass remains expensive, the energy locked up in the plant biomass will largely remain unused.

An attractive means for reducing the cost of degrading plant biomass is to make transgenic plants that contain cellulases and hemicellulases. For example, WO 98/11235 to Lebel et al. discloses transgenic plants that express cellulases in the chloroplasts of the transgenic plants or transgenic plants wherein the cellulases are targeted to the chloroplasts. Preferably, the cellulases are operably linked to a chemically-inducible promoter to restrict expression of the cellulase to an appropriate time. However, because a substantial portion of the cellulose in plants is in the form of lignocellulose, extracts from the transgenic plants are inefficient at degrading the cellulose in the lignocellulose.

U.S. Pat. No. 5,981,835 to Austin-Phillips et al. discloses transgenic tobacco and alfalfa which express the cellulases E2, or E3 from *Thermomononospora furca*. The genes encoding the E2 or E3, which were modified to remove their leader sequence, were placed under the control of a constitutive promoter and stably integrated into the plant genome. Because the leader sequence had been removed, the E2 or E3 product preferentially accumulated in the cytoplasm of the transgenic plants. However, because the cellulase can interfere with metabolic activities in plant cytoplasm, the growth of the transgenic plants can be impaired.

U.S. Pat. No. 6,013,860 to Himmel et al. discloses transgenic plants which express the cellulase E1 from *Acidothermus cellulolyticus*. The gene encoding E1, which was modified to remove the leader region, was placed under the control of a plastid specific promoter and the enzymes preferably produced in plastid.

While the above transgenic plants are an improvement, accumulation of cellulytic enzymes in the cytoplasm of a plant is undesirable since there is the risk that the cellulase will interact with metabolic activities in cytoplasm, and injure the plant. For example, research has shown that plants such as the avocado, bean, pepper, peach, poplar, and orange also contain cellulase genes, which are activated by ethylene during ripening and leaf and fruit abscission. Therefore, transgenic plants which contain large quantities of cellulase in the cytoplasm are particularly prone to damage. Furthermore, the cellulases accumulate in all tissues of the plant which can be undesirable. Restriction of cellulase expression to plastids and/or other sub-cellular compartments is desirable because it reduces the risk of plant damage due the accumulation of cellulases in the cytoplasm of the cells. However, for most crop plants, it has been difficult to develop a satisfactory method for introducing heterologous genes into the genome of plastids. Furthermore, cellulase is expressed in all tissues which contain plastids which can be undesirable.

For production of ligninases to use in degrading lignins, the ligninases of choice are from the white-rot fungus *Phanerochaete chrysosporium*. One of the major lignin-degrading, extracellular enzymes produced by *P. chrysosporium* is lignin peroxidase (LIP). Potential applications of LIP include not only lignin degradation but also biopulping of wood and biodegradation of toxic environmental pollutants. To produce large quantities of LIP, the fungus can be grown in large reactors and the enzyme isolated from the extracellular fluids. However, the yields have been low and the process has not been cost-effective. Production of recombinant LIP in *E. coli*, in the fungus *Trichoderma reesei*, and baculovirus have been largely unsuccessful. Heterologous expression of lignin-degrading manganese peroxidase in alfalfa plants has been reported; however, the transgenic plants had reduced growth and expression of the enzyme was poor ([2]Austin et al., Euphytica 85: 381-393 (1995)).

Although difficult to sufficiently and cheaply produce ligninases in non-plant systems, ligninases have evoked worldwide interest because of their potential in degrading a variety of toxic xenobiotic compounds such as PCBs and benzo(a)pyrenes in the environment ([3]Yadav et al., Appl. Environ. Microbiol. 61: 2560-2565 (1995); [4]Reddy, Curr.

Opin. Biotechnol. 6: 320-328 (1995); [5]Yadav at al., Appl. Environ. Microbiol. 61: 677-680 (1994)).

Therefore, a need remains for an economical method for making transgenic crop plants wherein the ligninase and cellulase genes are incorporated into the plant genome but wherein the ligninase and cellulase expression are restricted to particular plant tissues, e.g., the leaves, and the ligninase and cellulase products are directed to a plant organelle wherein it accumulates without damaging the transgenic plant.

SUMMARY OF THE INVENTION

Cereal cover crops such as oat, barley, early and late winter wheat, triticale and rye are used to extend the season of active nutrient uptake and living soil cover. Therefore, they reduce nutrient losses in water and sediment. They are also used to reduce soil erosion, reduce nitrogen leaching, and provide weed and pest suppression and increase soil organic matter.

Winter cereal cover crops are planted shortly before or soon after the cash crop harvest. Then these cover crops are killed before or soon after planting of the next cash crops in spring. Cereal grains such s those listed above, are excellent cover crops because they grow rapidly in cool weather, withstanding moderate frost, and their seed is relatively inexpensive. The total costs for production of cereal cover crops, including seeding, purchasing seeds, fertilizer and herbicide without tillage is only about $40-$50 per acre.

The present invention provides a method for converting lignocellulose of plant material to fermentable sugars comprising: (a) providing a transgenic monocot plant includes at least one DNA encoding a cellulase and hemicellulase which is operably linked to a nucleotide sequence encoding a signal peptide wherein the signal peptide directs the cellulase to an organelle of the transgenic plant and optionally at least one DNA encoding a ligninase which is operably linked to a nucleotide sequence encoding a signal peptide wherein the signal peptide directs the ligninase to the organelle of the transgenic plant; (b) growing the transgenic plant for a time sufficient for the transgenic plant to accumulate a sufficient amount of the cellulase and hemicellulase and the ligninase if present in the sub-cellular compartments of the transgenic plant; (c) harvesting the transgenic plant which has accumulated the cellulase, hemicellulase and ligninase if present in the sub-cellular compartments of the transgenic plant; (d) grinding the transgenic plant for a time sufficient to produce the plant material wherein the cellulase, hemicellulase and ligninase if present produced by the transgenic plant are released from organelle and cell wall areas of the transgenic plant; (e) incubating the plant material for a time sufficient for the cellulase, hemicellulase and ligninase if present in the plant material to produce the fermentable sugars and lignin deconstructed by the ligninase from the lignocellulose in the plant material; and (f) extracting the fermentable sugars produced from the cellulose and hemicelluloses by the cellulase and hemicellulase from the plant material.

The present invention further provides a method for converting lignocellulose of plant material from a cover crop with low amounts of lignin to fermentable sugars comprising: providing a transgenic monocot plant which is the cover crop which includes at least one DNA encoding a cellulase and hemicellulase which is operably linked to a nucleotide sequence encoding a signal peptide wherein the signal peptide directs the cellulase to an organelle of the transgenic plant and optionally at least one DNA encoding a ligninase which is operably linked to a nucleotide sequence encoding a signal peptide wherein the signal peptide directs the ligninase to the organelle of the transgenic plant; growing the transgenic plant for a time sufficient for the transgenic plant to accumulate a sufficient amount of the cellulase and hemicellulase and limited amounts of the ligninase if present in the sub-cellular compartments of the transgenic plant; harvesting the transgenic plant which has accumulated the cellulase, hemicellulase and ligninase if present in the sub-cellular compartments of the transgenic plant; grinding the transgenic plant for a time sufficient to produce the plant material wherein the cellulase, hemicellulase and ligninase if present produced by the transgenic plant are released from the organelle and cell wall areas of the transgenic plant; incubating the plant material for a time sufficient for the cellulase, hemicellulase and ligninase if present in the plant material to produce the fermentable sugars and lignin deconstructed by the ligninase from the lignocellulose in the plant material; and extracting the fermentable sugars produced from the cellulose and hemicelluloses by the cellulase and hemicellulase from the plant material. In further embodiments, the DNA encoding the cellulase is from an organism selected from the group consisting of *Trichoderma reesei*, *Acidothermus ceilulyticus*, *Streptococcus salivarius*, *Actinomyces naeslundi*, and *Thermomonospora fusca*. In further still embodiments, the DNA encoding the cellulase is selected from the group consisting of an e1 gene from *Acidothermus cellulyticus*, a cbh1 gene from *Trichoderma reesei*, a dextranase gene from *Streptococcus salivarius*, and a beta-glucosidase gene from *Actinomyces naeslundi*. In still further embodiments, the e1 gene comprises the nucleotide sequence set forth in SEQ ID NO:4, the cbh1 gene comprises the nucleotide sequence set forth in SEQ ID NO:10, the dextranase gene comprises the nucleotide sequence set forth in SEQ ID NO:8, and the beta-glucosidase gene comprises the nucleotide sequence set forth in SEQ ID NO:6. In still further embodiments, the DNA encoding the ligninase is from *Phanerochaete chrysosporium*. In further still embodiments, the hemicellulase or xylanase is Xyl1 from *Cochliobolus carbonum*. In further embodiments, the ligninase is ckg4 comprising the nucleotide sequence set forth in SEQ ID NO:11 or ckg5 comprising the nucleotide sequence set forth in SEQ ID NO:13. In still further embodiments, DNA encoding the cellulase and the DNA encoding the ligninase are each operably linked to a leaf-specific promoter. In further still embodiments, the leaf-specific promoter is a promoter for rbcS. In still further embodiments, the nucleotide sequence encoding the signal peptide encodes a signal peptide of rbcS. In further still embodiments, the rbcS comprises the nucleotide sequence set forth in SEQ ID NO:1. In a further still embodiment for any one of the aforementioned transgenic plants of the present invention, the transgenic plant is selected from the group consisting of rice, wheat, barley and rye. In still further embodiments, the first and second DNAs are stably integrated into nuclear or plastid DNA of the transgenic plant. In further still embodiments, the transgenic plants further include a DNA encoding a selectable marker operably linked to a constitutive promoter. In still further embodiments, the DNA encoding the selectable marker provides the transgenic plant with resistance to an antibiotic, an herbicide, or to environmental stress. In further still embodiments, the DNA encoding resistance to the herbicide is a DNA encoding phosphinothricin acetyl transferase which confers resistance to the herbicide phosphinothricin. In still further embodiments, the sub-cellular compartment of the transgenic plant is selected from the group consisting of nucleus, microbody, endoplasmic reticulum, endosome, vacuole, mitochondria, chloroplast, or plastid. In further still embodiments, the sub-cellular compartments of the transgenic plant are the chloroplast, apoplast (cell wall areas), endoplasmic reticulum, mitochondria or vacuole. In still further embodiments, the plant material further includes a plant material made from a non-transgenic plant. In further still embodiments, the hemicellulase is from *Cochliobolus carbonum*. In still further embodiments, the hemicellulase is Xyl1 gene encoding a xylanase.

OBJECTS

It is an object of the present invention to provide cover crop transgenic plants which degrade lignin of lignocellulose and deconstruct cellulose and hemicellulase to hexos (6 carbon) and pentose (5 carbon) fermentable sugars, methods for making the transgenic plants which degrade lignocellulose, and methods for using the transgenic plants to degrade cellulose and hemicellulose to fermentable sugars.

These and other objects of the present invention will become increasingly apparent with reference to the following drawings and preferred embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The abbreviations are:
CaMV 35S: Cauliflower Mosaic Virus 35S Promoter
Ω: Tobacco Mosaic Virus translational enhancer
Pr1a SP: the sequence encoding the tobacco

The abbreviations are:
Act1-5': Rice acting 1 promoter
Hva1: Barley Leah Protein coding sequences
PinII-3': Potato proteinase inhibitor terminator

FIGS. 20 to 24 are diagrams of various gene constructs used for genetic transformation of E1, CBH1, xylanase or ligninase genes targeted into different sub-cellulase compartments of cover crops.

Figure 1:
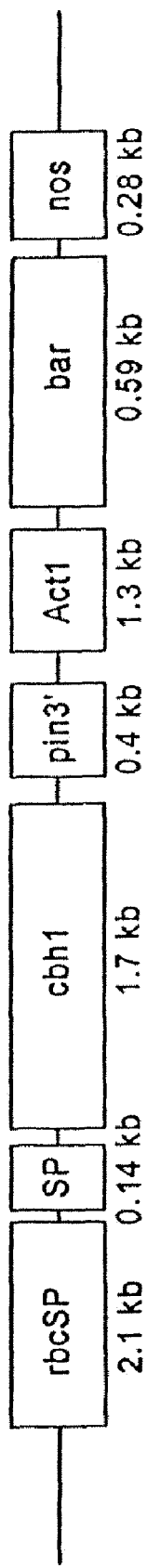
FIG. 1 is a diagram of a plasmid containing a heterologous gene expression cassette containing cbh1 operably linked to the rbcS promoter and DNA encoding the rbcS signal peptide and a heterologous gene expression cassette containing the bar gene operably linked to the Act1 promoter. rbcSP is the rbcS gene promoter, SP is DNA encoding the rbcS signal peptide, pin3' is the 3' untranslated region of the potato inhibitor II-chloramphenicol acetyltransferase gene, Act1 is the promoter for the act1 gene, and nos is the 3' untranslated region of the *Agrobacterium* nopaline synthase gene.

The abbreviations are:
RbcS1-P: Chrysanthemum Ribulose bisphosphate carboxylase (Rubisco) promoter
E1: Endoglucanase
CBH1: Exoglucanase
CKG4: Ligninase
RbcS1-T: Chrysanthemum Ribulose bisphosphate carboxylase (Rubisco) terminator
SPS: signal peptide for secretion derived from sea anemone equistatin
SPC: chloroplast signal peptide from Chrysanthemum morifolium small subunit protein
SPM: yeast CoxIV secretion (mitochondrial) signal

DESCRIPTION OF THE PREFERRED EMBODIMENTS

All patents, patent applications, government publications, government regulations, and literature references cited in this specification are hereby incorporated herein by reference in their entirety. In case of conflict, the present description, including definitions, will control.

The term "cellulase" is used herein as a generic term that includes endoglucanases such as the E1 beta-1,4-endoglucanase precursor gene (e1) of *Acidothermus cellulolyticus* and exoglucanases such as the cellobiohydrolase gene (cbh1) of *Trichoderma reesei* (also classified by some as *Trichoderma longibrachiatum*), the dextranase gene of *Streptococcus* salivarius encoding the 1,6-alpha-glucanhydrolase gene, and the beta-glucosidase gene from *Actinomyces* naeslundi. Endoglucanases randomly cleave cellulose chains into smaller units. Exoglucanases include cellobiohydrolases, which liberate glucose dimers (cellobiose) from the ends of cellulose chains; glucanhydrolases, which liberate glucose monomers from the ends of cellulose chains; and, beta-glucosidases, which liberate D-glucose from cellobiose dimers and soluble cellodextrins. When all of the above enzymes are combined, they work synergistically to rapidly decrystallize and hydrolyze cellulose to hexose fermentable sugars. Similarly, hemicellulases will deconstruct the hemicellulases (endo-xylanase, exoxylase) into pentose fermentable sugars.

The term "lignin" is used herein as a generic term that includes both lignins and lignocelluloses.

The term "ligninase" is used herein as a generic term that includes all varieties of enzymes which degrade lignins such as the lignin peroxidase gene of *Phanerochaete* chrysosporium.

A variety of fungi and bacteria produce ligninase and cellulase enzymes, and based on evolutionary pressures, these fungi are able to degrade lignin or cellulose and hemicellulose of plant residues in the soil. In the laboratory, cellulases have been used to hydrolyze or convert cellulose and hemicellulose into mixtures of simple sugars that can be used in fermentation to produce a wide variety of useful chemical and fuel products, including but not limited to, ethanol, lactic acid, and 1,3-propanediol, which is an important molecular building block in the production of environmentally-friendly plastics.

The biodegradation of lignin on cereals that are not cover crops, which comprises 20-30% of the dry mass of woody plants, is of great economic importance because these pre-treatment processes are at costs of $1.20 to $2.20 per gallon of ethanol and therefore an important rate-limiting step in production of alcohol fuels. Furthermore, there is considerable potential for the transformation of lignin into aromatic chemical feedstock. Also, delignification of lignocellulosic feeds has been shown to increase their digestibility by cattle by about 30%, therefore, contributing to enhanced cost effectiveness for producing milk and meat. Moreover, research on lignin biodegradation has important implications in biopulping and biobleaching in the paper industry.

The present invention provides transgenic monocot cover crop plants which produce cellulases, and optionally ligninases, in the leaves and straw/stalks of the plant. While the transgenic plant can be any plant which is practical for commercial production, it is preferable that the transgenic plants be constructed from plants which are produced in large quantities and which after processing produce a substantial amount of leaves and stalks as a byproduct. Therefore, it is desirable that the cover crop transgenic plant be constructed from plants including, but not limited to rice, wheat, barley and rye.

Thus, the transgenic cover crop plants of the present invention provide a plentiful, inexpensive source of fungal or bacterial cellulases, hemicellulases, which can be used to degrade cellulose and hemicellulose in plants to fermentable sugars for production of ethanol or for other uses. Also fungal and bacterial ligninases that convert lignin residues into aromatic compounds such as pre-treating silage to increase the energy value of lignocellulosic feeds for cows and other ruminant animals, pre-treating lignocellulosic biomass for fermentative conversion to fuels and industrial chemicals, and biodegradation of chloroaromatic environmental pollutants. Because the transgenic plants of the present invention produce the ligninases, cellulases, or both therein, the external addition of ligninases and cellulases for degradation of the plant material is no longer necessary. Therefore, the present invention enables the plant biomass, which is destined to become ethanol or other products, to serve as the source of ligninase and cellulase. Furthermore, the plant material from the transgenic plants of the present invention can be mixed with non-transgenic plant material. The cellulases and ligninases, or both produced by the transgenic plants will degrade the lignin and cellulose of all the plant material, including the non-transgenic plant material. Thus, ligninase and cellulase degradation of plant material can be carried out more economically.

The transgenic plants of the present invention comprise one or more heterologous gene expression cassettes containing DNA encoding at least one fungal or bacterial ligninase, cellulase, or both inserted into the plant's nuclear genome. The preferred cellulase is encoded by a DNA from the microorganism *Acidothermus cellulolyticus, Thermomonospora fusca,* and *Trichoderma reesei (Trichoderma longibrachiatum)*. Other microorganisms which produce cellulases suitable for the present invention include *Zymomonas mobilis, Acidothermus cellulolyticus, Cloostridium thermocellum, Eiwinia chrysanthemi, Xanthomonas campestris,* Alkalophilic *Bacillus* sp., *Ceilulomonas fimi*, wheat straw mushroom (*Agaricus bisporus*), *Ruminococcus flavefaciens, Ruminococcus albus, Fibrobacter succinogenes,* and *Butyrivibrio fibrisolvens.* Also the transgenic plants of the present invention comprise of cellulases, hemicellulases and ligninases that exist in guts of carpenter ant, termite, and in microbes that exist in the guts of rumen animals.

The preferred ligninase is lignin peroxidase (LIP) encoded in DNA from *Phanerochaete chrysosporium* or *Phlebia radiata.* One of the major lignin-degrading, extracellular enzymes produced by *P. chrysosporium* is LIP. The LIPs are glycosylated heme proteins (MW 38 to 46 kDa) which are dependent on hydrogen peroxide for activity and catalyze the oxidative cleavage of lignin polymer. At least six heme proteins (H1, H2, H6, H7, H8, and H10) with LIP activity have been identified in *P. chrysosporium* strain BKMF-1767 of which isozymes H2, H6, H8, and H10 are the major LIPs in both static and agitated cultures of *P. chrysosporium*. However, other fungi which produce ligninases suitable for use in the present invention include *Bjerkandera adusta, Trametes hirsuta, Plebia radiata, Pleurotus* spp., *Stropharia aurantiaca, Hypholoma fasciculare, Trametes versicolor, Gymnopilus penetrnas, Stereum hirsutum, Mycena haematopus,* and *Armillaria mellea.*

In the present invention, the transgenic plant comprises a DNA encoding one or more cellulase fusion proteins wherein the DNA encoding the cellulases are operably linked to a DNA encoding a signal peptide which directs the cellulase fusion protein to a plant organelle such as the nucleus, a microbody (e.g., a peroxisome, or specialized version thereof, such as a glyoxysome), an endoplasmic reticulum, an endosome, a vacuole, a mitochondria, a chloroplast, or a plastid. By sequestering the cellulase fusion proteins in the plant organelle, the cellulase fusion protein is targeted for storage into sub-cellular compartments including chloroplast, apoplast, endoplasmic reticulum, mitochondria, vacuole to avoid their interactions with cytoplasmic activities and harming of transgenic plants. In particular embodiments of the present invention, the gene encoding the cellulase is modified by replacing the amino acid codons that encode the leader region of the cellulase with amino acid codons that encode the signal peptide.

In a preferred embodiment of the invention, the amino acid codons that encode the signal peptide that directs the protein to which it is attached to the plant organelle, the chloroplasts, are the nucleotide codons that encode the rice rubisco synthase gene (rbcS) small subunit signal peptide (rbcSSP). The nucleotide sequence of the rbcS is set forth in SEQ ID NO:1 (GenBank Accession No. X07515). The 47 amino acid signal peptide of the rbcS protein has the amino acid sequence MAPPS VMASS ATIVA PFQGS SPPPA CRRPP SELQL RQRQH GGRIR CM (SEQ ID NO:2). The rbcS SP directs proteins to which it is operably linked to the chloroplasts of the transgenic plant. Therefore, in the preferred embodiment of the present invention, the transgenic plant comprises a DNA encoding the cellulase operably linked with a DNA encoding the rbcS SP to produce the cellulase fusion protein. The rbcS SP directs the cellulase fusion protein to the chloroplasts. Thus, the cellulase fusion protein produced by the transgenic plant accumulates in the chloroplasts of the transgenic plant which protects the transgenic plant from degradation by the cellulase fusion protein while it is being cultivated. Alternatively, the DNA encoding the cellulase is modified at its 3' end to encode a transit peptide such as the peptide RAVARL (SEQ ID NO:3), which targets the ligninase fusion protein to the peroxisomes (U.S. Pat. No. 6,103,956 to Srienc et al.). Preferably, the leader region of the cellulase is also removed. In any one of the above embodiments, the cellulase can be further modified to include a GC content that approximates the GC content of the genomic DNA of the plant by methods well known in the art.

In a preferred embodiment, the cellulase comprising the cellulase fusion protein is encoded by the E1 beta-1,4-endoglucanase precursor gene (e1) of *Acidothermus cellulolyticus*, the cellobiohydrolase gene (cbh1) of *Trichoderma reesei* (*Trichoderma longibrachiatum*), the beta-glucosidase gene from *Actinomyces naeslundi*, or the glucanhydrolase (dextranase) gene from *Streptococcus salivarius*. The nucleotide sequence of the e1 DNA is set forth in SEQ ID NO:4 (GenBank Accession No. U33212), which encodes the cellulase with the amino acid sequence set forth in SEQ ID NO:5. SEQ ID NO:6 provides the nucleotide sequence of the beta-glucosidase gene from *Actinomyces naeslundi* (GenBank Accession No. AY029505), which encodes the beta-glucosidase with the amino acid sequence set forth in SEQ ID NO:7. SEQ ID NO:8 provides the nucleotide sequence of the dextranase gene from *Streptococcus salivarius* (GenBank Accession No. D29644), which encodes a glucanhydrolase with the amino acid sequence set forth in SEQ ID NO:9. The nucleotide sequence of cbh1 is set forth in SEQ ID NO:10 (GenBank Accession No. E00389), which encodes the cellulase that includes the joined exons from positions 210 to 261, 738 to 1434, and 1498-1881.

In the present invention, the transgenic plant comprises a DNA encoding one or more ligninase fusion proteins wherein a DNA encoding the ligninase is operably linked to a DNA encoding a signal peptide which directs the ligninase fusion protein to a plant organelle. By sequestering the ligninase fusion proteins in the plant sub-cellular compartments, the modified ligninase is prevented from damaging the cytoplasm of transgenic plants while the plant is being cultivated. In particular embodiments of the present invention, the leader sequence of the gene encoding the ligninase is modified by replacing the amino acid codons that encode the leader region of the ligninase with amino acid codons that encode the signal peptide.

In a preferred embodiment of the invention, the amino acid codons that encode the signal peptide are the amino acid codons which encode the rice rubisco synthase gene (rbcS) small subunit signal peptide (rbcSSP). The nucleotide sequence of the rbcS is set forth in SEQ ID NO:1 (GenBank Accession No. X07515). The 47 amino acid signal peptide of the rbcS protein has the amino acid sequence MAPPS VMASS ATIVA PFQGS SPPPA CRRPP SELQL RQRQH GGRIR CM (SEQ ID NO:2). Therefore, in the preferred embodiment of the present invention, the transgenic plant comprises a DNA encoding the ligninase operably linked to a DNA encoding the rbcS SP. The rbcS SP directs the ligninase fusion protein to the chloroplasts. Thus, the ligninase fusion protein produced by the transgenic plant accumulates in the chloroplasts of the transgenic plant which protects the transgenic plant from degradation by the ligninase fusion protein while it is being cultivated. Alternatively, the DNA encoding the ligninase is modified at its 3' end to encode a transit peptide such as the peptide RAVARL (SEQ ID NO:3). Optionally, the leader region of the ligninase is also removed. In any one of the above embodiments, the ligninase can be further modified to include a GC content that approximates the GC content of the genomic DNA of the plant by methods well known in the art.

In a preferred embodiment of the invention, the ligninase comprising the ligninase fusion protein is encoded by the lignin peroxidase gene (LIP) genes ckg4 (H2) and ckg5 (H10) of *Phanerochaete crysosporium* ([3]de Boer et al., Gene 6: 93-102 (1987), [7]Corrigendum in Gene 69: 369 (1988)). The nucleotide sequence of the ckg4 gene is set forth in SEQ ID NO:11 (GenBank Accession No. M18743), which encodes the amino acid with the sequence set forth in SEQ ID NO:12. The nucleotide sequence of the ckg5 gene is set forth in SEQ ID NO:13 (GenBank Accession No. M18794), which encodes the amino acid with the sequence set forth in SEQ ID NO:14.

In the present invention, transcription and, therefore, expression of the ligninase and cellulase fusion proteins are effected by a promoter that is active in a particular tissue of the plant, e.g., a promoter that is active primarily in the leaves of a plant. A leaf-specific promoter that is preferred for transcription (expression at the RNA level) is the rice rubisco synthase gene promoter (rbcSP), which has the nucleotide sequence prior to the rbcS gene coding region included in SEQ ID NO:1. In some embodiments of the present invention, it is desirable to relegate transcription of the heterologous gene expression cassette to the seeds using a seed-specific promoter. Seed-specific promoters that are suitable include, but are not limited to, the seed-specific promoters such as the maize 19 kDa zein (cZ19B1) promoter, the maize cytokinin-induced message (Cim1) promoter, and the maize myo-inositol-1-phosphate synthase (mi1ps) promoter, which are disclosed in U.S. Pat. No. 6,225,529 to Lappegard et al. Therefore, in the heterologous gene expression cassettes, the nucleotide sequence comprising rbcS promoters are operably linked to the nucleotide sequences encoding the ligninase and cellulase fusion proteins. Thus, in a transgenic plant of the present invention, transcription of the ligninase and cellulase fusion proteins occurs primarily in the leaves of the plant, and because the ligninase and cellulase fusion proteins each has a signal peptide that directs its transport to plastids, the ligninase and cellulase fusion proteins accumulate in the plastids.

In the preferred embodiment of the present invention, the 3' ends of the nucleotide sequence encoding the above ligninase and cellulase fusion proteins are operably linked to a 3' non-coding sequence wherein the noncoding sequence contains a poly(A) cleavage/addition site and other regulatory sequences which enables the RNA transcribed therefrom to be properly processed and polyadenylated which in turn affects stability, transport and translation of the RNA transcribed therefrom in the plant cell. Examples of 3' noncoding sequences include the 3' noncoding sequence from the potato protease inhibitor II gene, which includes nucleotides 871 to 1241 of SEQ ID NO: 15 (GenBank Accession No. M15186) and the 3' noncoding sequence from the Agrobacterium nopaline synthase gene, which includes nucleotides 2001 to 2521 of SEQ ID NO:16 (GenBank Accession No. V00087 J01541).

The above heterologous gene expression cassettes can be constructed using conventional molecular biology cloning methods. In a particularly convenient method, PCR is used to produce the nucleotide fragments for constructing the gene expression cassettes. By using the appropriate PCR primers, the precise nucleotide regions of the above DNAs can be amplified to produce nucleotide fragments for cloning. By further including in the PCR primers restriction enzyme cleavage sites which are most convenient for assembling the heterogenous gene expression cassettes (e.g., restriction enzyme sites that are not in the nucleotide fragments to be cloned), the amplified nucleotide fragments are flanked with the convenient restriction enzyme cleavage sites for assembling the nucleotide fragments into heterogenous gene expression cassettes. The amplified nucleotide fragments are assembled into the heterogeneous gene expression cassettes using conventional molecular biology methods. Based upon the nucleotide sequences provided herein, how to construct the heterogenous gene expression cassettes using conventional molecular biology methods with or without PCR would be readily apparent to one skilled in the art.

In a further embodiment of the present invention, the transgenic plant comprises more than one heterogeneous gene expression cassette. For example, the transgenic plant comprises a first cassette which contains a DNA encoding a ligninase fusion protein, and one or more cassettes each containing a DNA encoding a particular cellulase fusion protein. Preferably, both the ligninase and cellulase fusion proteins comprise amino acids of a signal peptide which directs the fusion proteins to plant organelles. In a preferred embodiment, the signal peptide for each is the rbcS SP or the SKL motif.

In a further still embodiment, the transgenic plant comprises DNA encoding the ligninase fusion protein such as the ckg4 or ckg5 LIP, an endoglucanase fusion protein such as the e1 fusion protein, and a cellobiohydrolase fusion protein such as the cbh1 fusion protein. In a further still embodiment, the transgenic plant comprises DNA encoding the ligninase fusion protein such as the ckg4 or ckg5 LIP, an endoglucanase fusion protein such as the e1 fusion protein, a cellobiohydrolase fusion protein such as the cbh1 fusion protein, a beta-glucosidase, and a glucanhydrolase. Preferably, both the ligninase and cellulase fusion proteins comprise amino acids of a signal peptide which directs the fusion proteins to plant organelles. In a preferred embodiment, the signal peptide for each is the rbcS SP or the SKL motif.

To make the transgenic plants of the present invention, plant material such as meristem primordia tissue (or immature embryo-derived cell and callus line) is transformed with plasmids, each containing a particular heterogenous gene expression cassette using the Biolistic bombardment method as described in Example 5 and in U.S. Pat. No. 5,767,368 to Zhong et al. Further examples of the Biolistic bombardment method are disclosed in U.S. application Ser. No. 08/036,056 and U.S. Pat. No. 5,736,369 to Bowen at al. Each heterogenous gene expression cassette is separately introduced into a plant tissue and the transformed tissue propagated to produce a transgenic plant that contains the particular heterogenous gene expression cassette. Thus, the result is a transgenic plant containing the heterogenous gene expression cassette expressing a ligninase such as ckg4 or ckg5, a transgenic plant containing a heterogenous gene expression cassette expressing endoglucanase such as e1, a transgenic plant containing a heterogenous gene expression cassette expressing a cellobiohydrolase such as cbh1, a transgenic plant containing a heterogenous gene expression cassette expressing an exoglucanase such as beta-glucosidase, and a transgenic plant containing a heterogenous gene expression cassette expressing an exoglucanase such as glucanhydrolase.

Alternatively, transformation of corn plants can be achieved using electroporation or bacterial mediated transformation using a bacterium such as Agrobacterium tumefaciens to mediate the transformation of corn root tissues (see [8]Valvekens et al. Proc. Nat'l. Acad. Sci. USA. 85: 5536-5540 (1988)) or meristem primordia.

In a preferred embodiment of the present invention, the transgenic plant comprises one or more ligninase fusion proteins and one or more cellulase fusion proteins. Construction of the preferred transgenic plant comprises making first generation transgenic plants as above, each comprising a ligninase fusion protein, and transgenic plants as above, each comprising a cellulase fusion protein. After each first generation transgenic plant has been constructed, progeny from each of the first generation transgenic plants are cross-bred by sexual fertilization to produce second generation transgenic plants comprising various combinations of both the ligninase fusion protein and the cellulase fusion protein.

For example, various combinations of progeny from the first generation transgenic plants are cross-bred to produce second generation transgenic plants that contain ckg4 and cbh1, e1, beta-glucosidase, or ckg5; second generation transgenic plants that contain ckg5 and cbh1, e1, or beta-glucosidase; second generation transgenic plants that contain e1 or beta glucosidase, and a second generation transgenic plant that contains e1 and beta-glucosidase.

Progeny of the second generation transgenic plants are cross-bred by sexual fertilization among themselves or with first generation transgenic plants to produce third generation transgenic plants that contain one or more ligninases, one or more cellulases, or combinations thereof.

For example, cross-breeding a second generation transgenic plant containing ckg4 and cbh1 with a second generation transgenic plant containing e1 and beta-glucosidase produces a third generation transgenic plant containing ckg4, cbh1, e1, and beta-glucosidase. The third generation transgenic plant can be cross-bred with a first generation transgenic plant containing ckg5 to produce a fourth generation transgenic plant containing ckg4, ckg5, cbh1, e1, and beta-glucosidase.

It will be readily apparent to one skilled in the art that other transgenic plants with various combinations of ligninases and cellulases can be made by cross-breeding progeny from particular transgenic plants. [9]Zhang et al, Theor. Appl. Genet. 92: 752-761, (1996), [10]Zhong et al, Plant Physiol. 110: 1097-1107, (1996); and [11]Zhong et al, Planta, 187: 483-489, (1992) provide methods for making transgenic plants by sexual fertilization.

Alternatively, plant material is transformed as above with a plasmid containing a heterologous gene expression cassette encoding the ligninase fusion protein. The transgenic plant is recovered from the progeny of the transformed plant material. Next, plant material from the transgenic plant is transformed with a second plasmid containing a heterologous gene expression cassette encoding the cellulase fusion protein and a second selectable marker. The transgenic plant is recovered from the progeny of the transformed plant material. It will be readily apparent to one skilled in the art that transgenic plants containing any combination of ligninases and cellulases can be made by the above method.

In a preferred embodiment, the above heterologous gene expression cassettes further include therein nucleotide sequences that encode one or more selectable markers which enable selection and identification of transgenic plants that express the modified cellulase of the present invention. Preferably, the selectable markers confers additional benefits to the transgenic plant such as herbicide resistance, insect resistance, and/or resistance to environmental stress.

Alternatively, the above transformations are performed by co-transforming the plant material with a first plasmid containing a heterologous gene expression cassette encoding a selectable marker and a second plasmid containing a heterologous gene expression cassette encoding a ligninase or cellulase fusion protein. The advantage of using a separate plasmid is that after transformation, the selectable marker can be removed from the transgenic plant by segregation, which enables the selection method for recovering the transgenic plant to be used for recovering transgenic plants in subsequent transformations with the first transgenic plant.

Examples of preferred markers that provide resistance to herbicides include, but are not limited to, the bar gene from *Streptomyces hygroscopicus* encoding phosphinothricin acetylase (PAT), which confers resistance to the herbicide glufosinate; mutant genes which encode resistance to imidazalinone or sulfonylurea such as genes encoding mutant form of the ALS and AHAS enzyme as described by [12]Lee at al. EMBO J. 7: 1241 (1988) and [13]Miki et al., Theor. Appl. Genet. 80: 449 (1990), respectively, and in U.S. Pat. No. 5,773,702 to Penner et al.; genes which confer resistance to glycophosphate such as mutant forms of EPSP synthase and aroA; resistance to L-phosphinothricin such as the glutamine synthetase genes; resistance to glufosinate such as the phosphinothricin acetyl transferase (PAT and bar) gene; and resistance to phenoxy proprionic acids and cycloshexones such as the ACCAse inhibitor-encoding genes ([14]Marshall et al. Theor. Appl. Genet. 83: 435 (1992)). The above list of genes which can import resistance to an herbicide is not inclusive and other genes not enumerated herein but which have the same effect as those above are within the scope of the present invention.

Examples of preferred genes which confer resistance to pests or disease include, but are not limited to, genes encoding a *Bacillus thuringiensis* protein such as the delta-endotoxin, which is disclosed in U.S. Pat. No. 6,100,456 to Sticklen et al.; genes encoding lectins, ([15]Van Damme et al., Plant Mol. Biol. 24: 825 (1994)); genes encoding vitamin-binding proteins such as avidin and avidin homologs which can be used as larvicides against insect pests; genes encoding protease or amylase inhibitors, such as the rice cysteine proteinase inhibitor ([16]Abe et al., J. Biol. Chem. 262: 16793 (1987)) and the tobacco proteinase inhibitor I ([17]Hubb et al., Plant Mol. Biol. 21: 985 (1993)); genes encoding insect-specific hormones or pheromones such as ecdysteroid and juvenile hormone, and variants thereof, mimetics based thereon, or an antagonists or agonists thereof; genes encoding insect-specific peptides or neuropeptides which, upon expression, disrupts the physiology of the pest; genes encoding insect-specific venom such as that produced by a wasp, snake, etc.; genes encoding enzymes responsible for the accumulation of monoterpenes, sesquiterpenes, asteroid, hydroxaminc acid, phenylpropanoid derivative or other non-protein molecule with insecticidal activity; genes encoding enzymes involved in the modification of a biologically active molecule (see U.S. Pat. No. 5,539,095 to Sticklen et al., which discloses a chitinase that functions as an anti-fungal); genes encoding peptides which stimulate signal transduction; genes encoding hydrophobic moment peptides such as derivatives of Tachyplesin which inhibit fungal pathogens; genes encoding a membrane permease, a channel former or channel blocker (for example cecropin-beta lytic peptide analog renders transgenic tobacco resistant to *Pseudomonas solanacerum*) ([18]Jaynes et al. Plant Sci. 89: 43 (1993)); genes encoding a viral invasive protein or complex toxin derived therefrom (viral accumulation of viral coat proteins in transformed cells of some transgenic plants impart resistance to infection by the virus the coat protein was derived as shown by [19]Beachy at al. Ann. Rev. Phytopathol. 28: 451 (1990); genes encoding an insect-specific antibody or antitoxin or a virus-specific antibody ([20]Tavladoraki et al. Nature 366: 469 (1993)); and genes encoding a developmental-arrestive protein produced by a plant, pathogen or parasite which prevents disease. The above list of genes which can import resistance to disease or pests is not inclusive and other genes not enumerated herein but which have the same effect as those above are within the scope of the present invention.

Examples of genes which confer resistance to environmental stress include, but are not limited to, mt1d and HVA1, which are genes that confer resistance to environmental stress factors; rd29A and rd19B, which are genes of *Arabidopsis thaliana* that encode hydrophilic proteins which are induced in response to dehydration, low temperature, salt stress, or exposure to abscisic acid and enable the plant to tolerate the stress ([21]Yamaguchi-Shinozaki et al., Plant Cell 6: 251-264 (1994)). Other genes contemplated can be found in U.S. Pat. Nos. 5,296,462 and 5,356,816 to Thomashow. The above list of genes, which can import resistance to environmental stress, is not inclusive and other genes not enumerated herein but which have the same effect as those above are within the scope of the present invention.

Thus, it is within the scope of the present invention to provide transgenic plants which express one or more ligninase fusion proteins, one or more cellulase fusion proteins, and one or more of any combination of genes which confer resistance to an herbicide, pest, or environmental stress.

In particular embodiments of the present invention, the heterologous gene expression cassettes can further be flanked with DNA containing the matrix attachment region (MAR) sequence. While use of MAR in the present invention is optional, it can used to increase the expression level of transgenes, to get more reproducible results, and to lower the average copy number of the transgene ([22]Allen et al., The Plant Cell 5: 603-613 (1993); [23]Allen et al., The Plant Cell 8: 899-913 (1996); [24]Mlynarova et al., The Plant Cell 8: 1589-1599 (1996)).

To degrade the lignocellulose in the leaves and stalks of the transgenic plants of the present invention, the transgenic plant is ground up to produce a plant material using methods currently available in the art to disrupt a sufficient number of the plant organelles containing the ligninase and cellulase therein. The ligninase and cellulase degrade the lignocellulose of the transgenic plant into fermentable sugars, primarily glucose, and residual solids. The fermentable sugars are used to produce ethanol or other products.

The transgenic plants can be processed to ethanol in an improvement on the separate saccharification and fermentation (SHF) method ([1]Wilke et al., Biotechnol. Bioengin. 6: 155-175 (1976)) or the simultaneous saccharification and fermentation (SSF) method disclosed in U.S. Pat. No. 3,990,944 to Gauss et al. and U.S. Pat. No. 3,990,945 to Huff et al. The SHF and SSF methods require pre-treatment of the plant material feedstock with dilute acid to make the cellulose more accessible followed by enzymatic hydrolysis using exogenous cellulases to produce glucose from the cellulose, which is then fermented by yeast to ethanol. In some variations of the SHF or SSF methods, the plant material is pre-treated with heat or with both heat and dilute acid to make the cellulose more accessible.

An SHF or SSF method that uses the transgenic plant material of the present invention as the feedstock is an improvement over the SHF or SSF method because the transgenic plant material contains its own cellulases and ligninases or cellulases. Therefore, exogenous ligninases and/or cellulases do not need to be added to the feedstock. Furthermore, because particular embodiments of the transgenic plant material produce ligninase, the need for pre-treatment of the plant material in those embodiments before enzymatic degradation is not necessary. In a further improvement over the SHF method, the transgenic plant material is mixed with non-transgenic plant material and the mixture processed to ethanol.

The following examples are intended to promote a further understanding of the present invention.

EXAMPLE 1

This example shows the construction of plasmids comprising a heterologous gene expression cassette comprising a DNA encoding a cellulase fusion protein and a heterologous gene expression cassette comprising a DNA encoding the bar gene (Table 1).

TABLE 1

| | Construct | Plasmid features |
|---|---|---|
| 1 | rbcSP/e1/pin 3'//Act1 P/bar/nos 3' | rbcSP leaf-specific promoter driving cellulase cDNA of A. cellulolyticus |
| 2 | rbcSP/cbh1/pin 3'//Act1 P/bar/nos 3' | rbcSP leaf-specific promoter driving cellulase cDNA of T. reesi |

TABLE 1-continued

| | Construct | Plasmid features |
|---|---|---|
| 3 | rbcSP/rbcS SP/e1/pin 3'//Act1 P/bar/nos 3' | The rbcS SP targets cellulase of A. cellulolyticus into maize chloroplasts |
| 4 | rbcSP/rbcS SP/cbh1/pin 3'// Act1 P/bar/nos 3' | The rbcS SP targets cellulase of T. reesi into maize chloroplasts |

Abbreviations:

The term "rbcSP" means the rice rubisco rbcS promoter region. The rbcSP is a leaf-specific promoter that limits transcription of rbcS to the leaves ([25]Schaeffer and Sheen, Plant Cell 3: 997-1012 (1991)). The nucleotide sequence for the rbcS promoter region is set forth in SEG ID NO:1.

The term "e1" means the cDNA isolated from *Acidothermus cellulolyticus* which encodes the cellulase E1 beta-1,4-endoglucanase precursor. The nucleotide sequence for the gene encoding e1 is set forth in SEQ ID NO:4. In this example, the codons for the 41 amino acid leader sequence (nucleotides 824 to 946 of SEQ ID NO:4) are removed.

The term "cbh1" means the cDNA isolated from *Trichoderma reesi* that encodes the cellulase cellobiohydrolase. The nucleotide sequence for the gene encoding cbh1 is set forth in SEQ ID NO:10. In this example, the codons for the 54 amino acid leader sequence (nucleotides 210 to 671 of SEQ ID NO:10) are removed.

The term "pin3'" means the potato protease inhibitor II-chloramphenicol acetyltransferase gene's 3' untranslated sequence which contains transcription termination signals ([26]Thornburg et al., Proc. Natl. Acad. Sci. USA 84: 744-748 (1987)). The pin3' untranslated sequence includes nucleotides 882 to 1241 of the nucleotide sequence set forth in SEQ ID NO: 15.

The term "bar" means the phosphinothricin acetyl transferase gene ([27]Thompson et al., EMBO J. 6: 2519-2523 (1987)). The bar gene is a selectable marker for herbicide resistance. The 5' end of bar is operably linked to the rice actin 1 gene promoter which has been shown to operable in maize ([10]Zhong et al., Plant Physiology 110: 1097-1107 (1996); [9]Zhang et al., Theor. Appl. Genet. 92: 752-761 (1996); [28]Zhang et al., Plant Science 116: 73-84 (1996)). The 3' end of bar is operably linked to the nos 3' untranslated sequences. The nucleotide sequence of the bar gene is set forth in SEQ ID NO:18 (GenBank Accession No. X05822), which encodes the bar having the amino acid sequence from nucleotides 160 to 711.

The term "Act1 P" means the rice Act1 gene promoter which further includes the 5' intron region ([29]McElroy et al., Mol. Gen. Genet. 231: 150-160 (1991)). The sequence of the Act1 gene and its promoter is set forth in SEQ ID NO:19 (GenBank Accession No. X63830).

The term "nos3'" means the 3' untranslated sequence from the *Agrobacterium* nopaline synthase gene encoding nopaline synthase of the amino acid sequence as set forth in SEQ ID NO:17 which includes nucleotides 2002 to 2521 of SEQ ID NO:16 (GenBank Accession No. V00087 J01541). The Nos3' sequence contains transcription termination signals.

The term "rbcS SP" means the rice rubisco small subunit signal peptide which consists of 47 codons encoding the peptide with the amino acid sequence set forth in SEQ ID NO:2. The rbcS SP directs the translocation of the rbcS small subunit or any polypeptide to which it is attached to the chloroplasts ([30]Loza-Tavera et al., Plant Physiol. 93: 541-548 (1990)).

Construct 1 contains the rice rubisco rbcS leaf-specific promoter which limits expression of the cellulase encoded by e1 to the cells of the leaves of the maize plant.

Construct 2 contains the rice rubisco rbcS leaf-specific promoter which limits expression of the cellulase encoded by cbh1 to the cells of the leaves of the maize plant.

Figure 2:
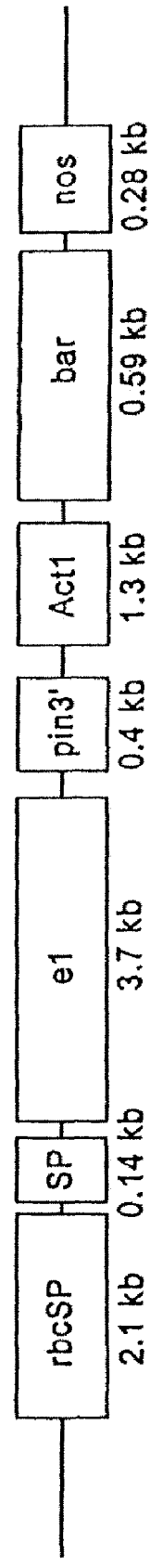
FIG. 2 is a diagram of a plasmid containing a heterologous gene expression cassette containing e1 operably linked to the rbcS promoter and DNA encoding the rbcS signal peptide and a heterologous gene expression cassette containing the bar gene operably linked to the Act1 promoter. The terms in the diagram are as in FIG. 1.

Construct 3, which is shown in FIG. 1, is like construct 1 except that DNA encoding the rbcS SP signal peptide is operably linked to the 5' end of the e1, and construct 4, which is shown in FIG. 2, is like construct 2 except that DNA encoding the rbcS SP signal peptide is operably linked to the 5' end of cbh1. Therefore, expression of cellulase from construct 3 or 4, which is limited to the cells of the leaves, directed to the chloroplasts in the cells. All of the above constructs are adjacent to a heterologous gene expression cassette containing the bar gene operably linked to the Act1 promoter.

Construction of plasmid rbcSP/rbcS SP/cbh1//pin3'//Act1 P/bar/nos3'. The starting plasmid was pBR10-11 which contained the cry1A(b) gene upstream of the pin3'. Between the cry1A(b) and the pin3' is a DNA polylinker containing in the following order a SmaI, BamHI, SpeI, XbaI, NotI, and EagI restriction enzyme recognition site. The plasmid pBR10-11 (available from Silan Dai and Ray Wu, Department of Molecular Biology and Genetics, Biotechnology Building, Cornell University, Ithaca, N.Y. 14853-2703) was digested with restriction enzymes SpeI and XbaI to produce a 9.2 kb DNA fragment. The 9.2 kb DNA fragment (pBR10-11/SpeI/XbaI/9.2 kb fragment) was purified by agarose gel electrophoresis.

The plasmid pB210-5a (available from William S. Adney, Mike Himmel, and Steve Thomas, National Renewable Energy Laboratory, 1670 Cole Boulevard, Golden Colo. 80401) containing the cbh1 gene from Trichoderma reesei (Trichoderma longibrachiatum) was digested with SpeI and XbaI. The digested plasmid was electrophoresed on an agarose gel and a 1.8 kb fragment (pB210-5a/SpeI/XbaI/1.8 kb fragment containing cbh1) was purified from the gel.

The above 9.2 kb and the 1.8 kb DNA fragments were ligated together using T4 DNA ligase to make plasmid "pBR10-11-cbh1" which was used to transform E. coli XL1 Blue. Transformed bacteria containing plasmid pBR10-11-cbh1 were identified by plating on LB agar gels containing ampicillin.

The plasmid pBR10-11-cbh1 was digested with SmaI and PstI. The PstI end was made blunt with mung bean exonuclease. The digested plasmid was electrophoresed on an agarose gel and the 2.8 kb DNA fragment containing cbh1 and pin3' was purified from the gel. The purified DNA fragment was designated "cbh1-pin3'/blunt-ended."

Figure 3:
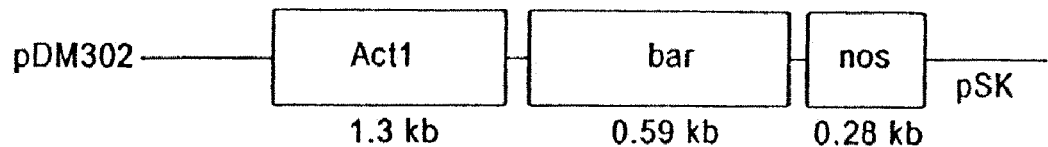
FIG. 3 is a diagram of a heterologous gene expression cassette containing the bar gene in plasmid pDM302. Act1 is the promoter for the act1 gene and nos is the 3' untranslated region of the *Agrobacterium* nopaline synthase gene.

The plasmid pDM302 ($^{31}$Cao at al., Plant Cell Reports 11: 586-591 (1992)), shown in FIG. 3, containing upstream of a ClaI site, a gene cassette consisting of the bar gene flanked by an upstream Act1 promoter and a downstream nos3', was digested with ClaI. The ClaI ends of the digested plasmid were made blunt with Taq DNA polymerase and the digested plasmid electrophoresed on an agarose gel. The digested plasmid was designated "pDM302/ClaI/blunt-ended."

The pDM302/ClaI/blunt-ended plasmid and the cbh1-pin3'/blunt-ended DNA fragment were ligated together using T4 DNA ligase to make plasmid "pDM302-cbh1-pin3'" which was used to transform E. coli XL1Blue. Transformed bacteria containing plasmid pDM302-cbh1-pin3' were identified by plating on LB agar gels containing ampicillin.

Plasmid pDM302-cbh1-pin3' was digested with SpeI, the ends made blunt with Taq DNA polymerase, and purified by agarose gel electrophoresis. The purified DNA fragment was designated "pDM302-cbh1-pin3'/SpeI/blunt-ended."

Plasmid pRR1 (available from Silan Dai and Ray Wu, Department of Molecular Biology and Genetics, Biotechnology Building, Cornell University, Ithaca, N.Y. 14853-2703), which contains the rice rbcS small subunit gene, was digested with PstI. The rbcS promoter is flanked by PstI sites. The PstI ends were made blunt with mung bean nuclease and the 2 kb DNA fragment (rice rbcS/PstI/blunt-ended) containing the promoter was purified by agarose gel electrophoresis.

Rice rbcSP/PstI/blunt-ended and plasmid pDM-cbh1-pin3'/SpeI/blunt-ended were ligated using T4 DNA ligase to make rbcSP/cbh1/pin3'//Act1P/bar/nos3' which was then used to transform E. coli XL Blue. Transformed bacteria containing plasmid rbcSP/cbh1/pin3'//Act1P/bar/nos3' were identified by plating on LB agar gels containing ampicillin.

PCR was used to insert NotI sites into rbcSP/cbh1/pin3'//Act1P/bar/nos3'. These sites were used to insert the rice rubisco signal peptide in place of the cbh1 signal peptide. The pRRI plasmid was the source of the rice rubisco signal peptide. It was also the used as a PCR template to produce the PCR product containing the rice rubisco signal peptide flanked by NotI cohesive termini. The rice rubisco signal peptide and the rbcSP/cbh1/pin3'//Act1P/bar/nos3' plasmid were ligated together using T4 DNA ligase to make rbcSP/rbcS SP/cbh1/pin3'//Act1P/bar/nos3' which was then used to transform E. coli XL Blue. Transformed bacteria containing plasmid rbcSP/rbcS SP/cbh1/pin3'//Act1P/bar/nos3' were identified by plating on LB agar gels containing ampicillin.

Construction of plasmid rbcSP/rbcS SP/e1/pin3'//Act1P/bar/nos3'. Plasmid pMPT4-5 (available from William S. Adney, Mike Himmel, and Steve Thomas, national Renewable Energy laboratory, 1670 Colorado Boulevard, Golden, Colo. 80401) contains the e1 gene encoding endoglucanase I from Acidothermus cellulolyticus as a 3.7 kb PvuI DNA fragment cloned into pGEM7 (Promega Corporation, Madison, Wis.). PCR was used to produce a DNA fragment containing the e1 gene flanked by AscI recognition sites. Plasmid rbcSP/cbh1/pin3Y/Act1P/bar/nos3' was also mutagenized by PCR to introduce AscI sites flanking the cbh1 gene. Next, the plasmid rbcSP/cbh1/pin3'//Act1P/bar/nos3' was digested with AscI and the plasmid free of the cbh1 gene was purified by agarose gel electrophoresis. The AscI flanked e1 gene was ligated using T4 DNA ligase into the rbcSP/cbh1/pin3'//Act1P/bar/nos3' free of the cbh1 gene to produce plasmid rbcSP/e1/pin37/Act1P/bar/nos3', which then used to transform E. coli. XL Blue. Transformed bacteria containing plasmid rbcSP/e1/pin3'//Act1P/bar/nos3' were identified by plating on LB agar gels containing ampicillin.

PCR was used to insert NotI sites into rbcSP/e1/pin3'//Act1P/bar/nos3'. These sites were used to insert the rice rubisco signal peptide in place of the cbh1 signal peptide. The pRRi plasmid was the source of the rice rubisco signal peptide. It was also the used as a PCR template to produce the PCR product containing the rice rubisco signal peptide flanked by NotI cohesive termini. The rice rubisco signal peptide and the rbcSP/e1/pin3'//Act1P/bar/nos3' plasmid were ligated together using T4 DNA ligase to make rbcSP/rbcS SP/e1/pin3'//Act1P/bar/nos3' which was then used to transform E. coli XL Blue. Transformed bacteria containing plasmid rbcSP/rbcS SP/e1/pin3'//Act1P/bar/nos3' were identified by plating on LB agar gels containing ampicillin.

Both heterologous gene expression cassettes are contiguous and the contiguous cassettes can be flanked by MAR sequences.

EXAMPLE 2

This example shows the construction of plasmids comprising a heterologous gene expression cassette comprising a DNA encoding a cellulase fusion protein. The plasmid constructs are shown in Table 2.

TABLE 2

| | Construct | Plasmid features |
|---|---|---|
| 1 | rbcSP/cbh1/pin 3' | rbcSP leaf-specific promoter driving cellulase cDNA of *T. reesei* |
| 2 | rbcSP/rbcS SP/cbh1/pin 3' | The rbcS SP targets cellulase of *T. reesi* into maize chloroplasts |
| 3 | rbcSP/rbcS SP/syn-cbh1/pin 3' | The rbcS SP targets modified cellulase of *T. reesei* into maize chloroplasts |
| 4 | CaMv35s/SSU/e1/nos3' | The SSU targets the cellulase of *A. cellulolyticus* into maize chloroplasts |
| 5 | CaMv35s/VSP/e1/nos3' | The VSP targets the cellulase of *A. cellulolyticus* into maize apoplasts |
| 6 | CaMv35s/e1/nos3' | No signal peptide |

Abbreviations:

The term "syn-cbh1" refers to a cbh1 gene that has been codon-modified for use in transformation of tobacco plants.

The term "CaMV3Ss" refers to the cauliflower mosaic virus promoter.

The term "SSU" refers to the *glycine max* rbcS signal peptide. *Glycine max* is a soybean and not a rice variety.

The term "VSP" refers to the soybean vegetative storage protein beta signal peptide.

The remainder of the terms in Table 2 are the same as those for table 1.

Figure 4:
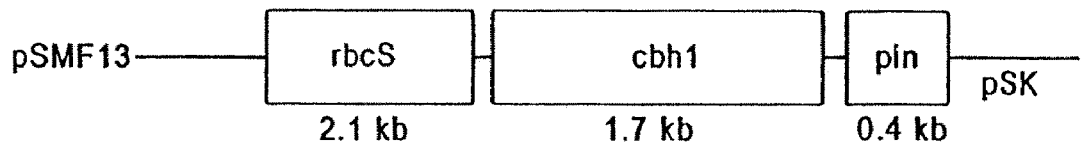
FIG. 4 is a diagram of plasmid pSMF13 which is plasmid pSK containing a heterologous gene expression cassette containing cbh1 operably linked to the rbcS promoter. The terms in the diagram are as in FIG. 1.

Construct 1, which is shown in FIG. 4, is plasmid pSMF13 which is plasmid pSK (Stratagene, La Jolla, Calif.) which contains cbh1 operably linked to the rice rubisco rbcS leaf-specific promoter which limits expression of the cellulase encoded by cbh1 to the cells of the leaves of the maize plant.

Figure 5:
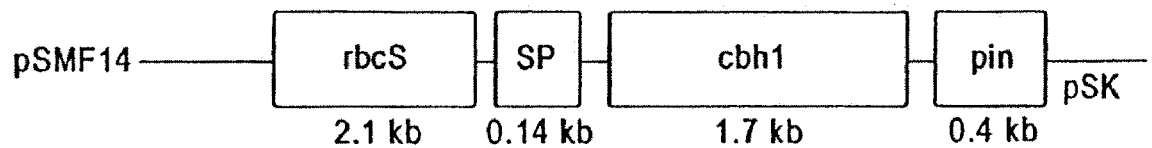
FIG. 5 is a diagram of plasmid pSMF14 which is plasmid pSK containing a heterologous gene expression cassette containing cbh1 operably linked to the rbcS promoter and DNA encoding the rbcS signal peptide. The terms in the diagram are as in FIG. 1.

Construct 2, which is shown in FIG. 5, is plasmid pSF15 which is plasmid pSK which contains cbh1 operably linked to the rice rubisco rbcS leaf-specific promoter which limits expression of the cellulase encoded by cbh1 to the cells of the leaves of the maize plant and a DNA encoding the rbcS SP which targets the cellulase to the chloroplasts.

Figure 6:
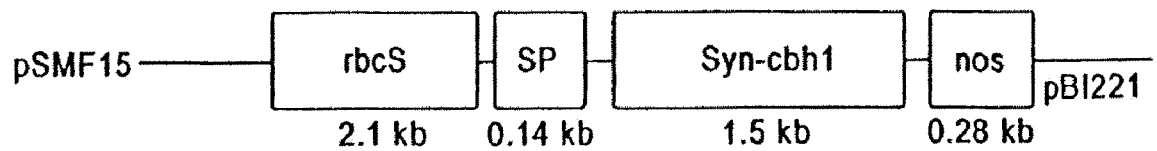
FIG. 6 is a diagram of plasmid pSMF15 which is plasmid pBI221 containing a heterologous gene expression cassette containing syn-cbh1 operably linked to the rbcS promoter and DNA encoding the rbcS signal peptide. The terms in the diagram are as in FIG. 1.

Construct 3, which is shown in FIG. 6, is like construct 2 except that the cbh1 has been modified to decrease the GC content of the cbh1 to an amount similar to the GC content of the tobacco plant genome. The nucleotide sequence of the modified cbh1 (syn-cbh1) in plasmid pBI221 is set forth in SEQ ID NO:20.

Figure 7:
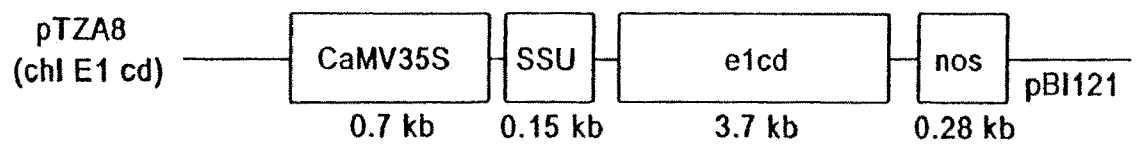
FIG. 7 is a diagram of plasmid pTZA8 which is plasmid pBI121 containing a heterologous gene expression cassette containing e1 operably linked to the CaMV35S promoter and DNA encoding the SSU signal peptide. SSU is the *glycine max* (soybean) rbcS signal peptide. CaMV35S is the cauliflower mosaic virus 35S promoter. The remainder of the terms are as in the diagram are as in FIG. 1.

Construct 4, which is shown in FIG. 7, is plasmid pTZA8 which is plasmid pBI121 which contains the caMV35s promoter, which is a constitutive promoter that is active in most plant tissues, to drive expression of e1 which is operably linked to a DNA encoding the SSU signal peptide which targets the cellulase to the chloroplasts.

Figure 8:
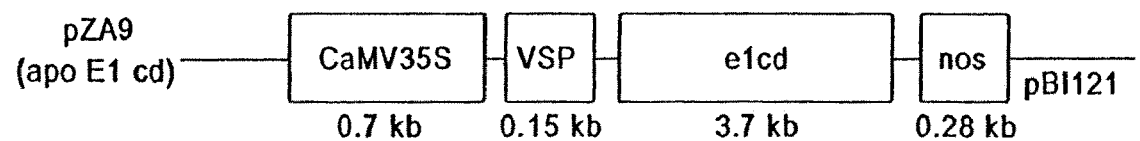
FIG. 8 is a diagram of plasmid pZA9 which is plasmid pBI121 containing a heterologous gene expression cassette containing e1 operably linked to the CaMV35S promoter and DNA encoding the VSP signal peptide. VSP is the soybean vegetative storage protein beta-leader sequences. The remainder of the terms in the diagram are as in FIG. 7.
Figure 9:
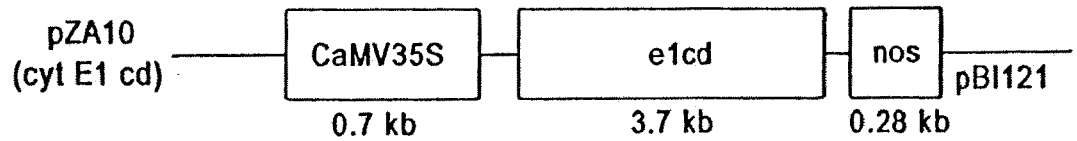
FIG. 9 is a diagram of plasmid pZA10 which is plasmid pBI121 containing a heterologous gene expression cassette containing e1 operably linked to the CaMV35S promoter. The remainder of the terms in the diagram are as in FIG. 7.

Construct 5, which is shown in FIG. 8, is plasmid pZA9 which is similar to construct 4 except the signal peptide is encoded by DNA encoding the VSP signal peptide which targets the cellulase to the apoplasts. Construct 6, which is shown in FIG. 9, is plasmid pZA10 which is similar to construct 4 or 5 except that e1 is not operably linked to a DNA encoding a signal peptide that targets the cellulase to a plant organelle.

The constructs were prepared as follows.

First, the plasmid pRR1, which contains the rice rbcS gene was obtained from Ray Wu and Silan Dai, Cornell University. The rice rubisco (rbcS) small subunit was cleaved from pRR1 using EcoRI and EcoRV restriction sites to release a 2.1 kb DNA fragment containing the rbcS. The 2.1 kb DNA fragment was ligated into the plasmid pSK between the EcoR1 and EcoRV sites to produce plasmid pSMF8. The 2.1 kb DNA fragment provided the promoter for the cbh1 constructs below.

Next, the cbh1 gene was cloned downstream of rbcS promoter in plasmid pSMF8. First, a 1.7 kb DNA fragment containing the cbh1 gene from *Trichoderma reesei* was isolated from plasmid pB210-5A (available from William S. Adney, Mike Himmel, and Steve Thomas, National Renewable Energy Laboratory; described in [32]Shoemaker et al., Bio/Technology 1: 691-696 (1983)) by digesting with SalI and XhoI. The ends of the 1.7 kb DNA fragment were made blunt end using DNA polymerase I (large fragment). The blunt-ended DNA fragment was cloned into plasmid pSMF8, which had been digested with BamHI and the ends made blunt with DNA polymerase I, to make plasmid pSMF9.

Next, to complete the heterologous gene expression cassette, the pin3' transcription termination nucleotide sequence was inserted at the 3' end of the cbh1 gene in plasmid pSMF9. The pin3' transcription termination nucleotide sequence was cleaved from pBR10-11 with PstI. However, to remove the pin3' transcription termination nucleotide sequence from pBR10-11, a PstI site had to be introduced upstream of the pin3' transcription termination nucleotide sequence.

To generate the PstI site upstream of the pin3' transcription termination nucleotide sequence in pBR10-11, the pBR10-11 was digested with NotI and XhoI and a 70 bp multi-cloning site nucleotide sequence, which had been isolated from the pSK vector by digesting with NotI and XhoI, was cloned between the NotI and XhoI sites of the pBR10-11 to produce plasmid pSMF11. The pin3' transcription termination nucleotide sequence was then removed from pSMF11 by digesting with PstI to produce a 1 kb DNA fragment which was then cloned into the PstI site of pSK, which had been digested with PstI, to produce plasmid pSMF12. PSMF12 was then digested with NotI to produce a 1 kb DNA fragment containing the pin3' transcription termination nucleotide sequence. The 1 kb DNA fragment cloned into the NotI site downstream of the cbh1 gene in pSMF9, which had been digested with NotI, to produce plasmid pSMF13 (construct 1 in Table 2).

Next, a DNA encoding a signal peptide which targets proteins to which it is attached to the chloroplasts was inserted upstream of the cbh1 and in the same reading frame as the cbh1. Thus, a fusion protein is produced from translation of RNA transcribed from the cbh1 DNA linked to the DNA encoding the signal peptide. DNA encoding the signal peptide (SP) was isolated from the rbcS in the pRR1 plasmid. Because there were no convenient restriction enzyme sites available which flanked the DNA encoding the SP for cloning, it was planned to PCR amplify that region containing the DNA encoding the SP using PCR primers with PCR primers that contained convenient restriction enzyme sites for cloning. At the end of the rbcS promoter pSMF13 is a unique AvrII site and upstream of the first ATG of the cbh1 gene is a unique BsrGI. A DNA encoding the SP that was flanked with an AvrII site on one end and a BsrGI site on the opposite end would be able to be cloned between the AvrII and BsrGI sites in PSMF13. That would place the DNA encoding the SP between the rbcS promoter and the cbh1 gene and would enable a fusion protein containing the SP fused to the cellulase.

Therefore, PCR primers were synthesized using DNA sequences for the AvrII and BsrGI sites and the SP DNA sequences. The upstream PCR primer (SP1F) had the nucleotide sequence 5'-CCGCCIAGGCGCATGGCCCCCTC-CGT-3' (SEQ ID NO:21) and the downstream PCR primer (SP3R) had the nucleotide sequence 5'-CGCTGTACACG-CACCTGATCCTGCC-3' (SEQ ID NO:22). Plasmid pRR1 encoding the SP was PCR amplified with the PCR primers and the 145 bp amplified product was purified using 2% agarose gel. The purified 145 bp product was sequenced to confirm that the 145 bp amplified product contained the SP nucleotide sequences. The amplified product was digested with AvrII and BsrGI and cloned between the AvrII and BsrGI sites of pSMF13 digested with AvrII and BsrGI to produce plasmid pSMF14.

To produce pSMF15 which contains a cbh1 gene codon-modified to decrease the GC content of the cbh1 gene to an amount similar to the GC content of the tobacco genome, a synthetic cbh1 (syn-cbh1) gene was obtained from plasmid pZD408 (available from Ziyu Dai, Pacific Northwest national Laboratory, 902 Battelle Boulevard, Richland, Wash. 99352). The syn-cbh1 is a cbh1 which had been codon-modified for use in tobacco plant transformations. The nucleotide sequence of syn-cbh1 is set forth in SEQ ID NO:20. Plasmid pZD408 was linearized with NcoI and the ends made blunt. Then, the blunt-ended pZD408 was digested with HindIII to remove the CaMV35S promoter. A 4.5 kb DNA fragment containing the syn-cbh1 was isolated from the CaMV35S promoter by agarose gel electrophoresis. The 4.5 kb DNA fragment was dephosphorylated and the DNA fragment containing a blunt end and a HindIII end was named pZD408B.

Plasmid pSMF14 was digested with BsrGI, the BsrGI ends made blunt, and then pSMF14 was digested with HindIII to produce a DNA fragment containing the rbcS promoter with the DNA encoding the SP flanked by a blunt end and a HindIII end. The DNA fragment was purified by agarose gel electrophoresis and ligated to the pZD408B DNA fragment to produce plasmid pSMF15 (construct 3 of Table 2).

The heterologous gene expression cassettes are contiguous can be flanked by MAR sequences.

EXAMPLE 3

This example shows the construction of plasmids comprising a heterologous gene expression cassette comprising a DNA encoding a ligninase fusion protein and a heterologous gene expression cassette comprising a DNA encoding the bar gene. The constructs are shown in Table 3.

TABLE 3

| | Construct | Plasmid features |
|---|---|---|
| 1 | rbcSP/ckg4/pin 3'//Act1 P/bar/nos 3' | rbcSP leaf-specific promoter driving ckg4 cDNA of *P. chrysosporium* |
| 2 | rbcSP/ckg5/pin 3'//Act1 P/bar/nos 3' | rbcSP leaf-specific promoter driving ckg5 cDNA of *P. chrysosporium* |
| 3 | rbcSP/rbcS SP/ckg4/pin 3'//Act1 P/bar/nos 3' | The rbcS SP targets ckg4 into maize chloroplasts |
| 4 | rbcSP/rbcS SP/ckg5/pin 3'// Act1 P/bar/nos 3' | The rbcS SP targets ckg5 into maize chloroplasts |

Abbreviations:

The terms "ckg4" and "ckg5" mean the ligninase cDNAs isolated from the basidiomycete *Phanerochaete. chrysosporium*, SEQ ID NO:11 and SEQ ID NO:13, respectively. The codons for the 28 amino acid leader are deleted so that the expressed gene product remains inside the cells.

The remainder of the terms in Table 3 are the same as those for Table 1. All plasmid constructs contain the selectable marker gene (bar) driven by the rice actin 1 gene promoter. The rice actin gene and its promoter are disclosed in U.S. Pat. No. 5,641,876 to McElroy et al.

Construct 1 contains the rice rubisco rbcS leaf-specific promoter which limits expression of the ligninase encoded by ckg4 to the cells of the leaves of the maize plant.

Construct 2 contains the rice rubisco rbcS leaf-specific promoter which limits expression of the ligninase encoded by ckg5 to the cells of the leaves of the maize plant.

Figure 10:
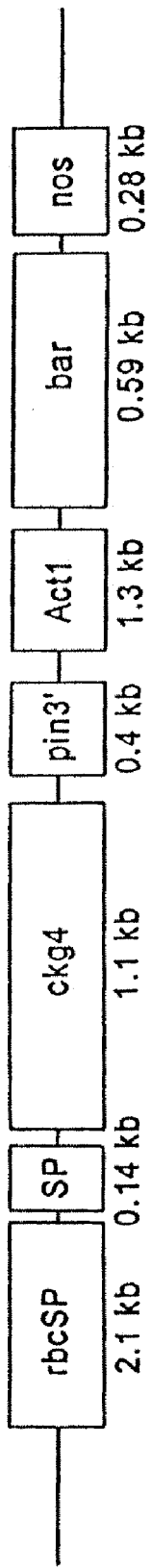
FIG. 10 is a diagram of a plasmid containing a heterologous gene expression cassette containing ckg4 operably linked to the rbcS promoter and DNA encoding the rbcS signal peptide and a gene expression cassette containing the bar gene operably linked to the Act1 promoter. The remainder of the terms in the diagram are as in FIG. 1.

Construct 3, which is shown in FIG. 10, contains the rice rubisco rbcS leaf-specific promoter which limits expression of the ligninase encoded by ckg4 to the cells of the leaves of the maize plant and further contains DNA encoding the rbcS SP which targets the ligninase to the chloroplasts.

Figure 11:
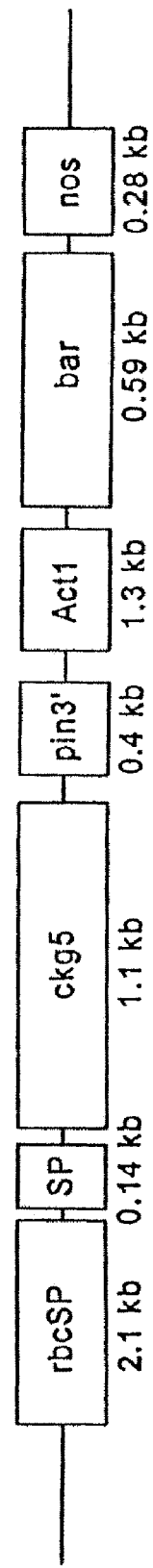
FIG. 11 is a diagram of a plasmid containing a heterologous gene expression cassette containing ckg5 operably linked to the rbcS promoter and DNA encoding the rbcS signal peptide and a gene expression cassette containing the bar gene operably linked to the Act1 promoter. The remainder of the terms in the diagram are as in FIG. 1.

Construct 4, which is shown in FIG. 11, contains the rice rubisco rbcS leaf-specific promoter which limits expression of the ligninase encoded by ckg5 to the cells of the leaves of the maize plant and further contains DNA encoding the rbcS SP which targets the ligninase to the chloroplasts. All of the above constructs are adjacent to a heterologous gene expression cassette containing the bar gene operably linked to the Act1 promoter. Both heterologous gene expression cassettes are contiguous and the contiguous cassettes can be flanked by MAR sequences.

EXAMPLE 4

This example shows the construction of plasmids comprising a heterologous gene expression cassette comprising a DNA encoding a ligninase fusion protein. The constructs are shown in Table 4.

TABLE 4

| | Construct | Plasmid features |
|---|---|---|
| 1 | rbcSP/ckg4/pin 3' | rbcSP leaf-specific promoter driving ckg4 cDNA of *P. chrysosporium* |
| 2 | rbcSP/ckg5/pin 3' | rbcSP leaf-specific promoter driving ckg5 cDNA of *P. chrysosporium* |
| 3 | rbcSP/rbcS SP/ckg4/pin 3' | The rbcS SP targets ckg4 into maize chloroplasts |
| 4 | rbcSP/rbcS SP/ckg5/pin 3' | The rbcS SP targets ckg5 into maize chloroplasts |

The terms in table 4 are the same as those for Tables 1 and 3.

Figure 12:
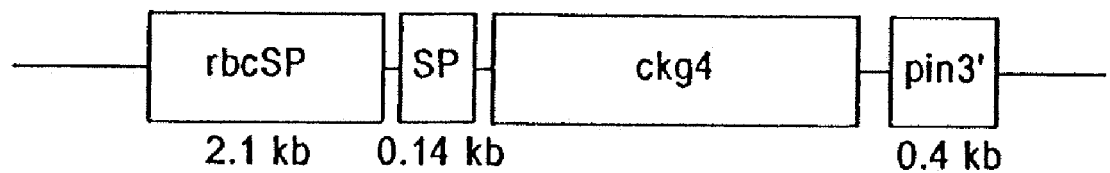
FIG. 12 is a diagram of plasmid pSMF18 containing a heterologous gene expression cassette containing ckg4 operably linked to the rbcS promoter. The remainder of the terms in the diagram are as in FIG. 1.

Construct 1, which is shown in FIG. 12, is plasmid pSMF18 which is plasmid pSK which contains the rice rubisco rbcS leaf-specific promoter which limits expression of the ligninase encoded by ckg4 to the cells of the leaves of the maize plant.

Figure 13:
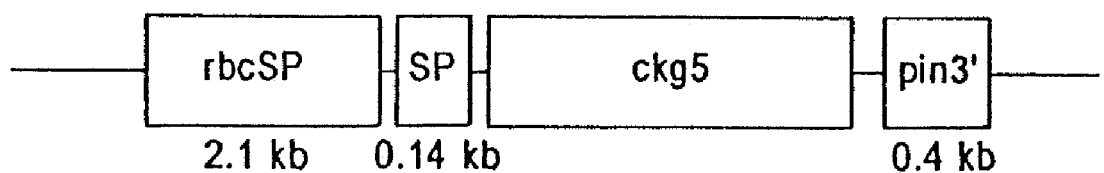
FIG. 13 is a diagram of plasmid pSMF19 containing a heterologous gene expression cassette containing ckg5 operably linked to the rbcS promoter. The remainder of the terms in the diagram are as in FIG. 1.

Construct 2, which is shown in FIG. 13, is plasmid pSMF19 which is plasmid pSK which contains the rice rubisco rbcS leaf-specific promoter which limits expression of the ligninase encoded by ckg5 to the cells of the leaves of the maize plant.

Figure 14:
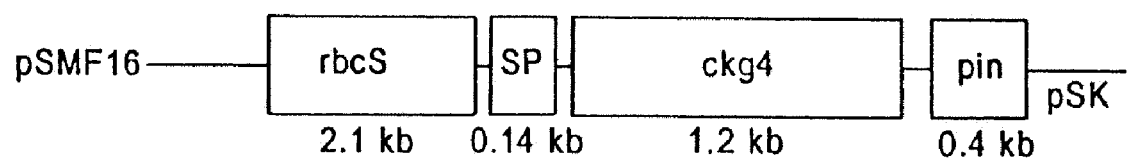
FIG. 14 is a diagram of plasmid pSMF16 containing a heterologous gene expression cassette containing ckg4 operably linked to the rbcS promoter and DNA encoding the rbcS signal peptide. The remainder of the terms in the diagram are as in FIG. 1.

Construct 3, which is shown in FIG. 14, is plasmid pMSF16 which is plasmid pSK which contains the rice rubisco rbcS leaf-specific promoter which limits expression of the ligninase encoded by ckg4 to the cells of the leaves of the maize plant and further contains DNA encoding the rbcS SP which targets the ligninase to the chloroplasts.

Figure 15:
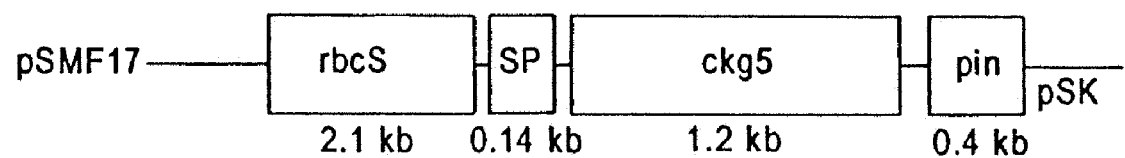
FIG. 15 is a diagram of plasmid pSMF17 containing a heterologous gene expression cassette containing ckg5 operably linked to the rbcS promoter and DNA encoding the rbcS signal peptide. The remainder of the terms in the diagram are as in FIG. 1.

Construct 4, which is shown in FIG. 15, is plasmid pSMF17 which is plasmid pSK which contains the rice rubisco rbcS leaf-specific promoter which limits expression of the ligninase encoded by ckg5 to the cells of the leaves of the maize plant and further contains DNA encoding the rbcS SP which targets the ligninase to the chloroplasts. The above heterologous gene expression cassettes can be flanked by MAR sequences.

The ligninase constructs shown in Table 4 are prepared as described below.

Two plasmids, pCLG4 and pCLG5, the former containing a cDNA clone encoding the ligninase gene ckg4 and the latter containing a cDNA clone encoding the ckg5 were obtained from Dr. C. Adinarayana Reddy, Department of Microbiology and Public Health, Michigan State University and described in [6]de Boer et al., Gene 6: 93-102 (1987), [7]Corrigendum in Gene 69: 369 (1988). These ligninase cDNA clones were prepared from a white-rot filamentous fungus (*Phanerochaete chrysosporium*). The cDNAs for ckg4 and ckg5 had each been cloned into the PstI site of the pUC9 plasmid to make pCLG4 and pCLG5, respectively. The codons for the 28-amino acid leader sequence is deleted from both cDNAs before cloning so that expressed gene product remains inside the cell.

Plasmid pSMF16 is made as follows. The ckg4 gene is removed from pCLG4 by digesting the plasmid with the restriction enzymes XbaI and BstEII to produce a 1.2 kb DNA fragment containing the ckg4 without the nucleotide sequence encoding the transit peptide. The BstEII removes the nucleotide sequences encoding the transit peptide of the ligninase.

The ends of the DNA fragment containing the ckg4 gene are made blunt and the blunt-ended DNA fragment is ligated into pSMF14 in which the cbh1 has been removed by digesting with BsrGI and XhoI and the ends made blunt to produce pSMF16.

Plasmid pSMF18 is made as follows. The nucleotide sequence encoding the rbcS signal peptide and cbh1 are removed from pSMF14 by digesting pSMF14 with AvrII and XhoI instead of BsrGI and XhoI. The ends of the digested pSMF14 are made blunt and the blunt-ended DNA fragment containing the ckg4 gene, prepared as above, is ligated into the digested pSMF14 to make plasmid pSMF18.

Plasmid pSMF17 is made as follows. The ckg5 gene is removed from pCLG5 by digesting the plasmid with the restriction enzymes XbaI and EagI to produce a 1.2 kb DNA fragment containing the ckg5 without the nucleotide sequence encoding the transit peptide. The EagI removes the nucleotide sequences encoding the transit peptide of the ligninase.

The ends of the DNA fragment containing the ckg5 are made blunt and the blunt-ended DNA fragment is ligated into pSMF14 in which the cbh1 has been removed by digesting with BsrGI and XhoI and the ends made blunt to produce pSMF17.

Plasmid pSMF19 is made as follows. The nucleotide sequence encoding the rbcS signal peptide and cbh1 are removed from pSMF14 by digesting pSMF14 with AvrII and XhoI instead of BsrGI and XhoI. The ends of the digested pSMF14 are made blunt and the blunt-ended DNA fragment containing the ckg5 gene, prepared as above, is ligated into the digested pSMF14 to make plasmid pSMF19.

EXAMPLE 5

This example shows the transformation of maize multi-meristem primordia via Biolistic bombardment with the plasmid constructs of Examples 1-4, regeneration of the transgenic plants, confirmation of the integration of the plasmid constructs into the plant genome, and confirmation of the expression of the cellulase or ligninase fusion proteins in the transgenic plant. For transformations with the constructs of Examples 2 and 4, which do not contain a selectable marker, a selectable marker comprising the bar gene in the plasmid pDM302 ([31]Cao et al., Plant Cell Reports 11: 586-591 (1992)) is cotransfected into the cells with the plasmid containing the ligninase or cellulase heterologous gene expression cassette.

Maize seeds have been germinated in Murashige and Skoog (MS) medium ([33]Murashige and Skoog, Physiol. Plant 15: 473-497 (1962)) supplemented with the appropriate growth regulators ([34]Zhong et al., Planta 187: 490-497 (1992)). Shoot meristems have been dissected and cultured for 2-3 weeks until an initial multiplication of meristem have been produced for bombardment.

The multi-meristem primordia explants (or immature embryo-derived cell and callus lines) are bombarded with tungsten particles coated with particular plasmids of Example 1 or 3 or with particular plasmids of Example 2 or 4 along with the plasmid containing the heterogenous gene expression cassette containing the bar gene. The bombarded explants are gently transferred onto meristem multiplication medium for further multiplication, about 6 to 8 more weeks. This step is required to reduce the degree of chimerism in transformed shoots prior to their chemical selection. Shoots are transferred to the above medium containing 5 to 10 mg per liter glufosinate ammonium (PPT) selectable chemical for another 6 to 8 weeks. Chemically selected shoots are rooted in rooting medium containing the same concentration of PPT. Plantlets are transferred to pots, acclimated, and then transferred to a greenhouse.

When the plantlets or shoots are small, the quantity of transgenic plant material is insufficient for providing enough DNA for Southern blot hybridization; therefore, polymerase chain reaction (PCR) is used to confirm the presence of the plasmid constructs the plantlets. The amplified DNA produced by PCR is resolved by agarose or acrylamide gel electrophoresis, transferred to membranes according standard Southern transfer methods, and probed with the appropriate DNA construct or portion thereof according to standard Southern hybridization methods. Those shoots or plantlets which show they contain the construct in its proper form are considered to have been transformed. The transformed shoots or plantlets are grown in the greenhouse to produce sufficient plant material to confirm that the plasmid constructs has been properly integrated into the plant genome. To confirm proper integration of the plasmid constructs into the plant genome, genomic DNA is isolated from the greenhouse grown transgenic plants and untransformed controls and analyzed by standard Southern blotting methods as in [10]Zhong et al., Plant Physiology 110: 1097-1107 (1996); [9]Zhang et al., Theor. Appl. Genet. 92: 752-761 (1996); [28]Zhang et al., Plant Science 116: 73-84 (1996); and, [35]Jenes et al., In *Transgenic Plants*. Vol. 1. Kung, S-D and Wu, R (eds.). Academic Press, San Diego, Calif. pp. 125-146 (1992).

To confirm expression of the ligninase or cellulase fusion protein, total cellular RNA is isolated from the greenhouse grown plant tissues as described in [10]Zhong et al., Plant Physiology 110: 1097-1107 (1996). The mRNA encoding the cellulase or ligninase fusion protein is detected by RNA Northern blot analysis using the same probes used for the Southern blot analyses. Briefly, the RNA is electrophoresed on a denaturing formaldehyde agarose gel, transferred to nitrocellulose or nylon membranes, hybridized to the appropriate ligninase or cellulase probe, and then exposed to X-ray autoradiology film. The hybridization bands are scanned using a densitometer which enables determination of the expression level of the specific mRNA.

Translation of the mRNA is confirmed by Western blot analysis according to the standard methods of [36]Towbin et al., Proc. Natl. Acad. Sci. USA 76: 4350 (1979) and [37]Burnette, Anal. Biochem. 112: 195 (1981) using antibodies specific for ligninase or cellulase.

EXAMPLE 6

Transgenic maize containing both a ligninase and a cellulase fusion protein is made by crossing-breeding the above-mentioned transgenic plants one of which contains cbh1 or e1 stably integrated into the genome and the other of which contains ckg4 or ckg5 stably integrated into the genome using the method provided in ([9]Zhang et al, Theor. Appl. Genet. 92: 752-761, (1996); [10]Zhong et al, Plant Physiol. 110: 1097-1107, (1996); [11]Zhong et al, Planta, 187: 483-489, (1992)). Transgenic plants that carry a low copy number of the DNA encoding the ligninase or cellulase fusion proteins are used for cross-breeding.

Briefly, transgenic maize plants that produce the ligninase fusion protein are made as disclosed in Example 5 to make a first transgenic plant and transgenic maize plants that produce the cellulase fusion protein are made as disclosed in Example 5 to make a second transgenic plant. The first and second transgenic plants are cross-pollinated to create a transgenic plant which produces both a ligninase and a cellulase fusion protein. The progeny are analyzed for homozygosity and transgenic plants that are homozygous for both the ligninase gene cassette and the cellulase gene cassette are selected for further propagation for seeds.

The progeny in the above crosses are used in subsequent crosses to produce transgenic maize with both ligninase gene cassettes and one, two, or three cellulase gene cassettes or transgenic maize with two or three cellulase gene cassettes and one ligninase gene cassette.

EXAMPLE 7

Production levels and activity of the cellulase fusion protein in transgenic maize made as in Example 5 or 6 is determined as follows.

Cellulase activity in transgenic maize is first assayed by standard methods (Ghose. In *Analytical Method* B-304, rev. A, IUPAC Commission on Biotechnology. A short Report (1984)) based on the time course assay for hydrolysis of a pre-weighed sample of filter paper at pH 4.8-5.2 and temperature of 50° C. While the filter paper assay is a standard substrate for cellulase activity, results using the filter paper assay are not particularly representative of the actual activity of the cellulase in plant materials containing cellulose, hemicellulose, and other sugars or sugar polymers. Therefore, a more accurate method for determining cellulase activity is used.

Plant material is ground and the ground material is suspended to a concentration of up to about 5% in 0.05 M citrate buffer at pH 4.8 and incubated with shaking at 50° C. Over a 48 hour time period, samples are removed at intervals of 0, 1, 3, 12, 24, and 48 hours. A minimal amount of sodium azide, about 0.05%, is added to the citrate buffer during incubation to control microbial activity. For analysis by high pressure liquid chromatography (HPLC), the supernatant fraction of each sample is removed, capped, and heated to inactivate the enzymes. The inactivated supernatant fraction is filtered through a syringe filter and analyzed by HPLC to measure the glucose, cellobiose, and xylose content of the samples according to established methods ([39]Dale et al., Biosource Technol. 56: 11-116 (1996)).

Cellulase activity is manifested by an increasing level of glucose, xylose and/or cellobiose levels in the supernatant fractions during the 48 hour period. The control for the above assay is to treat samples from non-transgenic plants with varying amounts of commercially available cellulase enzymes such as CYTOLASE 300 which is a cellulase from Genencor, Inc. and NOVOZYME 188 which is a cellobiose from Novo Laboratories, Inc. to confirm that the ground plant material is susceptible to hydrolysis.

EXAMPLE 8

Comparison of cellulase activity in transgenic maize prepared as in Example 5 or 6 treated to enhance cellulose accessibility.

Generally, cellulose and hemicellulose in plant material are not very accessible to hydrolytic enzymes such as cellulase. Therefore, it is possible that even if the cellulase fusion protein is produced in the transgenic plants of the present invention, its cellulase activity would not be measurable. Therefore, to demonstrate accessibility, samples of the transgenic maize plants of the present invention are treated by the ammonia fiber explosion process to increase cellulose and hemicellulose accessibility ([39]Dale et al., Biosource technol. 56: 11-116 (1996)). Samples treated are analyzed as in Example 3.

In previous experiments with coastal Bermuda grass, the ammonia fiber explosion process disrupted the plant cell walls sufficiently to permit over 80% extraction of plant protein, compared with less than 30% extraction under the same conditions prior to ammonia treatment ([40]de la Rosa et al., Appl. Biochem. Biotechnol. 45/46: 483-497 (1994). The process increased the hydrolytic effectiveness of the added cellulases by at least six-fold ([39]Dale et al., Biosource Technol. 56: 11-116 (1996)). Thus, it is expected that the ammonia fiber explosion process helps release cellulase from the transgenic maize chloroplasts and will also increase the access of the cellulase released to the cellulose in the plant material.

EXAMPLE 9

Production levels and activity of the ligninase fusion protein in transgenic maize made as in Example 5 or 6 can be determined as follows.

Maize leaves from the transgenic maize made as in Examples 5 or 6 are ground using a pestle and mortar. Chloroplasts are isolated from leaves of transgenic plants by Ficoll (Pharmacia) gradient centrifugation and ground as above.

The ground materials (leaves, grains, chloroplasts) are suspended in 50 mM L-tartrate buffer (pH 4.5), mixed well by vortexing, and centrifuged for 10 minutes at 14,000 rpm (16,000×g) at 4° C. and the supernatant fraction tested for lignin peroxidase (LIP) activity as described in [41]Tien et al., Meth. Enzymol. 161: 238-249 (1988). The LIP assay measures the production of veratraldehyde (as an increase in absorbance at 310 nm) from veratryl alcohol (substrate) in the presence of hydrogen peroxide. Control assays are done on non-transgenic maize seeds to measure endogenous peroxidase activity. The assay is sensitive and is able to detect very low levels of lignin peroxidase activity, e.g., conversion of 0.1 mmole substrate per minute per liter of test sample.

Soluble protein content is determined by the Bradford procedure ([42]Bradford, Anal. Biochem. 72: 248-254 (1976))

using bovine serum albumen (BSA) as the standard. LIP enzyme in the extracted fluid is purified by Fast Protein liquid Chromatography (FPLC) analysis using the Mono Q anion exchange system (Pharmacia) and a gradient of 0 to 1 M Na-acetate to elute the various isozymes CYadav et al., Appl. Environ. Microbiol. 61: 2560-2565 (1995); Reddy et al., FEMS Microbiol. Rev. 13: 137-152 (1994)). The relative activity, yield, pH optimum, stability, and other characteristics of the LIP in the transgenic plant are compared to that determined for the LIP isolated from the fungus. Furthermore, ground maize seeds or leaf extracts containing the LIP is used to treat various lignocellulosic feeds in small laboratory reactor systems and the extent of delignification can be analyzed per established procedures ([44]Van Soest et al., Assoc. Off. Anal. Chem. J. 51: 780-785 (1968)).

Detection of ligninase mRNA is by isolating the mRNA from the transgenic plants as above, resolving the mRNA by denaturing RNA gel electrophoresis, transferring the resolved mRNA to membranes, and probing the membranes with ckg4 or ckg5 cDNA probes.

Western blots are performed to determine whether the LIP protein is in an active or inactive form. The total protein from the transgenic plants is resolved by SDS-polyacrylamide gel electrophoresis and transferred to membranes. The membranes are probed with antibodies to LIP H2 (ckg4) or LIP H10 (ckg5).

No one has produced cellulose hydrolysis enzymes and/or ligninases in cereal cover crops. At present, cover crops are planted and destroyed. In the present invention, the transgenic cover crops are used for production of biofuels and biobased industrial material. As indicated above, cover crops are presently used to extend the season of active nutrient uptake and living soil cover. Therefore, they reduce nutrient losses in water and sediment. They are also used to reduce soil erosion, reduce nitrogen leaching, and provide weed and pest suppression and increase soil organic matter. In the present invention, all of the above advantages are achieved. At present, herbicides are used to destroy the cover crops in spring before planting of other crops (cash crops). In this invention, herbicide application costs are unnecessary, thus producing an additional benefit. The transgenic cover crops are harvested for biofuels and other biobased materials known in the art.

Figure 16:
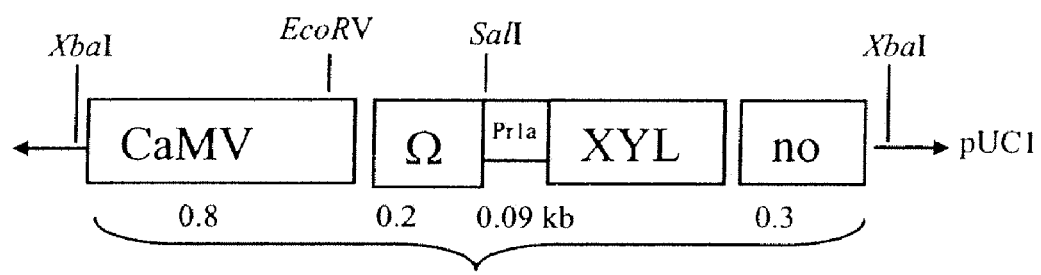
FIG. 16 is a diagram of a construct containing the *Cochliobolus carbonum* endoxylanase/hemicellulase cDNA regulated by the 35S promoter and enhancer. This construct contains the sequences encoding the tobacco pathogenesis-related protein 1a (Pr1a) signal peptide for targeting of XYL1 into plant apoplast.
Figure 17:
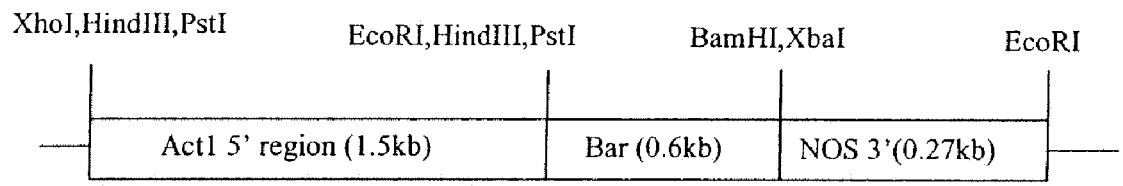
FIG. 17 is a diagram of a construct containing the bar herbicide resistance selectable marker gene controlled by rice actin 1 promoter and Nos terminator.
Figures 18A, 18B, 18C:
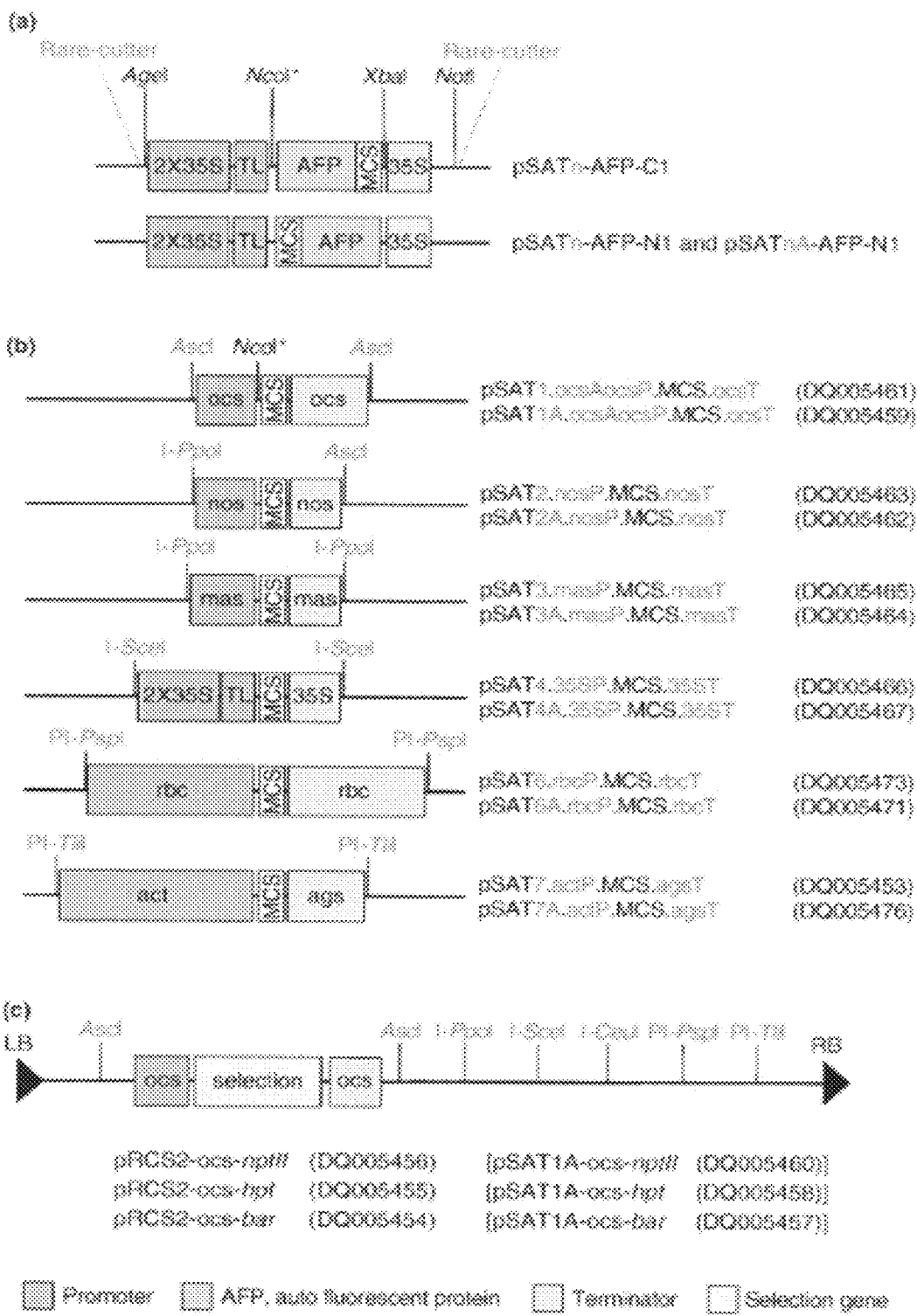
FIGS. 18A, 18B and 18C are diagrams showing commercially available cassettes.
Figure 19:
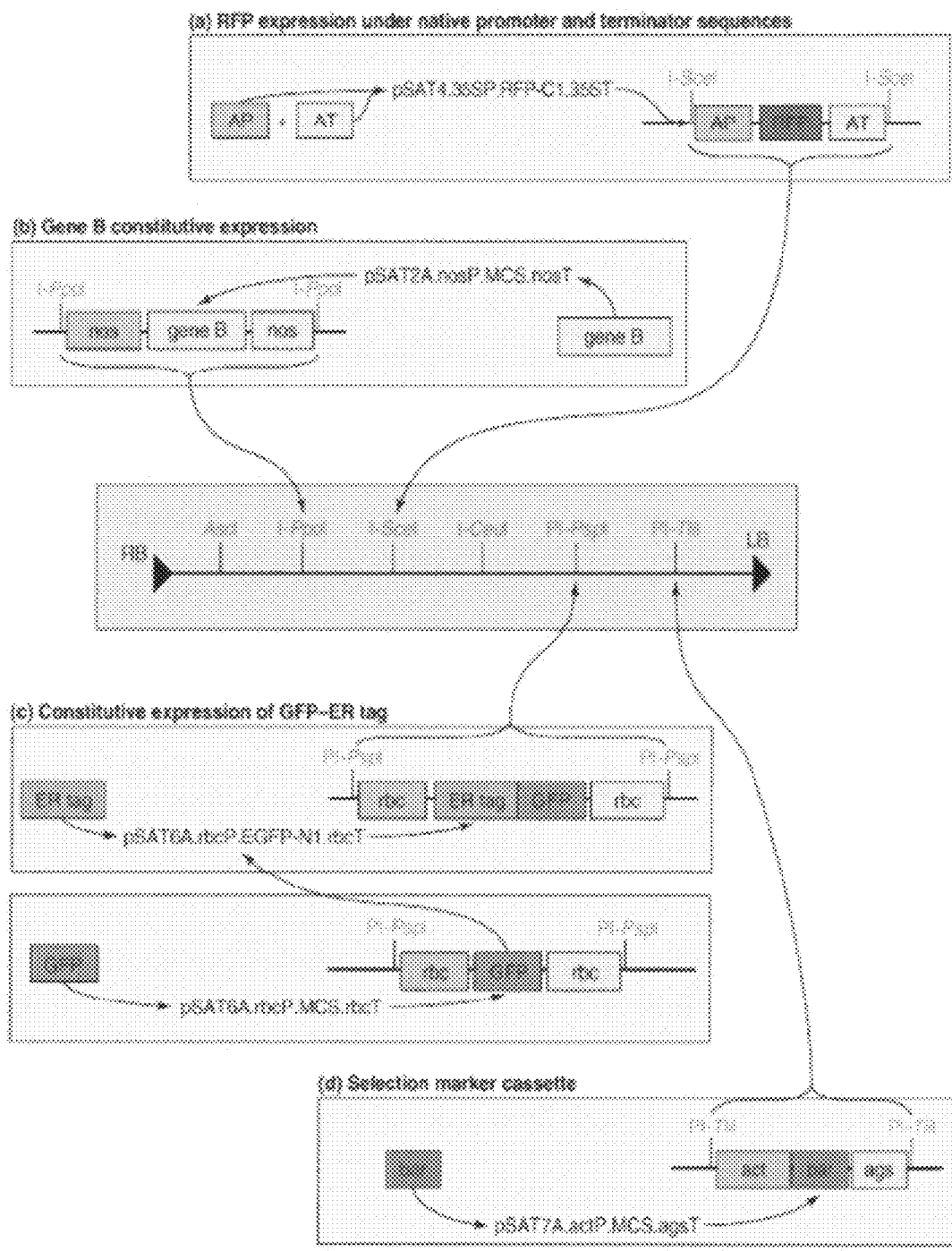
FIG. 19 is a diagram showing the insertion of genes (gene B) encoding a cellulose, hemicellulase, or ligninase into a sequence of DNA, for targeting to a sub-cellular compartment of the plant.

Two constructs were used, one with a hemicellulase (Xylanase or Xyl, such as Xyl1) (FIG. 16) and the other with a selectable maker (bar) gene (FIG. 17). In addition, two sets of ready made vectors were used then genes are inserted for targeting of the enzymes in chloroplast, apoplast (cell wall areas), ER, vacuole or mitochondria. These two sets include (1) a set of vectors from Invitrogen called Gateway (FIGS. 18 and 19), and the other set called Impact Vectors from Europe. FIGS. 20 to 24 are diagrams of the constructs used to target the sub-cellular compartments of the plants.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

The invention claimed is:

1. A method for providing transgenic plant material from a cover crop with low amounts of lignin, the method comprising:
(a) providing a transgenic monocot plant which is the low-lignin cover crop which includes (i) at least one DNA encoding a cellulase and hemicellulase which is operably linked to a nucleotide sequence encoding a signal peptide wherein the signal peptide directs the cellulase to an organelle of the transgenic monocot plant and (ii) at least one DNA encoding a ligninase which is operably linked to a nucleotide sequence encoding a signal peptide wherein the signal peptide directs the ligninase to the organelle of the transgenic monocot plant;
(b) growing the transgenic monocot plant for a time sufficient for the transgenic monocot plant to accumulate a sufficient amount of the cellulase, the hemicellulase, the ligninase in sub-cellular compartments of the transgenic monocot plant; and (c) harvesting the transgenic monocot plant which has accumulated the cellulase, the hemicellulase, the ligninase in the sub-cellular compartments of the transgenic monocot plant.

2. The method of claim 1, wherein the transgenic monocot plant is selected from the group consisting of rice, wheat, barley, oat, triticale, and rye.

3. The method of claim 1, wherein the sub-cellular compartment of the transgenic monocot plant is selected from the group consisting of nucleus, microbody, endoplasmic reticulum, endosome, vacuole, mitochondria, chloroplast, and plastid.

4. The method of claim 1, wherein the sub-cellular compartment of the transgenic monocot plant is selected from the group consisting of chloroplast, apoplast, endoplasmic reticulum, mitochondria, and vacuole.

5. The method of claim 1, wherein the DNA encoding the cellulase and hemicellulase and the DNA encoding the ligninase are each operably linked to a leaf-specific promoter.

6. The method of claim 1, wherein the DNA encoding the cellulase and hemicellulase and the DNA encoding the ligninase are stably integrated into nuclear or plastid DNA of the transgenic monocot plant.

7. The method of claim 1, wherein:
(i) the DNA encoding the cellulase is from an organism selected from the group consisting of *Trichoderma reesei, Acidothermus cellulyticus, Streptococcus salivarius, Actinomyces naeslundi*, and *Thermomonospora fusca*;
(ii) the DNA encoding the hemicellulase is from *Cochliobolus carbonum*; and
(iii) the DNA encoding the ligninase is from *Phanerochaete chrysosporium*.

8. The method of claim 1, wherein:
(i) the DNA encoding the cellulase is selected from the group consisting of an e1 gene comprising the nucleotide sequence set forth in SEQ ID NO:4 from *Acidothermus cellulyticus*, a cbh1 gene comprising the nucleotide sequence set forth in SEQ ID NO:10 from *Trichoderma reesei*, a dextranase gene comprising the nucleotide sequence set forth in SEQ ID NO:8 from *Streptococcus salivarius*, and a beta-glucosidase gene comprising the nucleotide sequence set forth in SEQ ID NO:6 from *Actinomyces naeslundi*;
(ii) the DNA encoding the hemicellulase is a Xyl1 gene encoding a xylanase; and
(iii) the DNA encoding the ligninase is selected from the group consisting of a ckg4 gene comprising the nucleotide sequence set forth in SEQ ID NO:11, and a ckg5 gene comprising the nucleotide sequence set forth in SEQ ID NO:13.

9. A method for providing transgenic plant material from a cover crop with low amounts of lignin, the method comprising:
(a) growing and harvesting a first cash crop on a plot of land;
(b) providing a transgenic monocot plant which is the low-lignin cover crop which includes at (i) least one DNA encoding a cellulase and hemicellulase which is operably linked to a nucleotide sequence encoding a signal peptide wherein the signal peptide directs the cellulase to an organelle of the transgenic monocot plant and (ii) optionally at least one DNA encoding a ligninase which is operably linked to a nucleotide sequence encoding a signal peptide wherein the signal peptide directs the ligninase to the organelle of the transgenic monocot plant;
(c) growing the transgenic monocot plant on the plot (i) during a winter season, (ii) subsequent to the harvesting of the first cash crop from the plot, and (iii) for a time sufficient for the transgenic monocot plant to accumulate a sufficient amount of the cellulase, the hemicellulase, and the ligninase if present in sub-cellular compartments of the transgenic monocot plant; and
(d) harvesting the transgenic monocot plant which has accumulated the cellulase, the hemicellulase, and the ligninase if present in the sub-cellular compartments of the transgenic monocot plant.

10. The method of claim 9, wherein the first cash crop is corn.

11. The method of claim 9, wherein the first cash crop is soybean.

12. The method of claim 9, wherein the transgenic monocot plant is selected from the group consisting of rice, wheat, barley, oat, triticale, and rye.

13. The method of claim 9, wherein the sub-cellular compartment of the transgenic monocot plant is selected from the group consisting of nucleus, microbody, endoplasmic reticulum, endosome, vacuole, mitochondria, chloroplast, and plastid.

14. The method of claim 9, wherein the sub-cellular compartment of the transgenic monocot plant is selected from the group consisting of chloroplast, apoplast, endoplasmic reticulum, mitochondria, and vacuole.

15. The method of claim 9, wherein the DNA encoding the cellulase and hemicellulase is stably integrated into nuclear or plastid DNA of the transgenic monocot plant.

16. The method of claim 9, wherein the transgenic monocot plant includes the at least one DNA encoding the ligninase.

17. The method of claim 9, wherein:
(i) the DNA encoding the cellulase is from an organism selected from the group consisting of *Trichoderma reesei, Acidothermus cellulyticus, Streptococcus salivarius, Actinomyces naeslundi*, and *Thermomonospora fusca*; and
(ii) the DNA encoding the hemicellulase is from *Cochliobolus carbonum*.

18. The method of claim 17, wherein the transgenic monocot plant includes the at least one DNA encoding the ligninase, and the DNA encoding the ligninase is from *Phanerochaete chlysosporium*.

19. The method of claim 9, wherein:
(i) the DNA encoding the cellulase is selected from the group consisting of an e1 gene comprising the nucleotide sequence set forth in SEQ ID NO:4 from *Acidothermus cellulyticus*, a cbh1 gene comprising the nucleotide sequence set forth in SEQ ID NO:10 from *Trichoderma reesei*, a dextranase gene comprising the nucleotide sequence set forth in SEQ ID NO:8 from *Streptococcus salivarius*, and a beta-glucosidase gene comprising the nucleotide sequence set forth in SEQ ID NO:6 from *Actinomyces naeslundi*; and
(ii) the DNA encoding the hemicellulase is a Xyl1 gene encoding a xylanase.

20. The method of claim 19, wherein the transgenic monocot plant includes the at least one DNA encoding the ligninase, and the DNA encoding the ligninase is selected from the group consisting of a ckg4 gene comprising the nucleotide sequence set forth in SEQ ID NO:11, and a ckg5 gene comprising the nucleotide sequence set forth in SEQ ID NO:13.

* * * * *